US012790592B2

(12) United States Patent
Tsai et al.

(10) Patent No.: US 12,790,592 B2
(45) Date of Patent: Nov. 10, 2026

(54) IN VITRO HUMAN BLOOD BRAIN BARRIER

(71) Applicant: Massachusetts Institute of Technology, Cambridge, MA (US)

(72) Inventors: Li-Huei Tsai, Cambridge, MA (US); Joel Blanchard, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 881 days.

(21) Appl. No.: 17/424,529

(22) PCT Filed: Jan. 22, 2020

(86) PCT No.: PCT/US2020/014572
§ 371 (c)(1),
(2) Date: Jul. 21, 2021

(87) PCT Pub. No.: WO2020/154374
PCT Pub. Date: Jul. 30, 2020

(65) Prior Publication Data

US 2022/0090021 A1 Mar. 24, 2022

Related U.S. Application Data

(60) Provisional application No. 62/795,520, filed on Jan. 22, 2019.

(51) Int. Cl.

| | |
|---|---|
| ***C12N 5/071*** | (2010.01) |
| ***C12N 5/00*** | (2006.01) |
| ***C12N 5/079*** | (2010.01) |
| ***G01N 33/50*** | (2006.01) |

(52) U.S. Cl.
CPC ......... *C12N 5/0691* (2013.01); *C12N 5/0062* (2013.01); *C12N 5/0622* (2013.01); *G01N 33/5058* (2013.01); *G01N 33/5064* (2013.01); *G01N 33/5088* (2013.01); *C12N 2502/28* (2013.01); *C12N 2513/00* (2013.01); *C12N 2533/90* (2013.01)

(58) Field of Classification Search
CPC .. C12N 5/0691; C12N 5/0062; C12N 5/0622; C12N 2502/28; C12N 2513/00; C12N 2533/90; C12N 2503/00; G01N 33/5058; G01N 33/5064; G01N 33/5088
See application file for complete search history.

(56) References Cited

U.S. PATENT DOCUMENTS

| | | | |
|---|---|---|---|
| 5,223,409 | A | 6/1993 | Ladner et al. |
| 6,316,405 | B1 | 11/2001 | Rich et al. |
| 6,869,768 | B2 | 3/2005 | Comings et al. |
| 8,552,041 | B2 | 10/2013 | Cohen et al. |
| 8,629,242 | B2 | 1/2014 | Vitek et al. |
| 9,387,206 | B2 | 7/2016 | Cohen et al. |
| 9,943,552 | B2 | 4/2018 | Kihm et al. |
| 9,944,986 | B2 | 4/2018 | Nagy |
| 10,201,558 | B2 | 2/2019 | Power et al. |
| 10,590,393 | B2 | 3/2020 | Shusta et al. |
| 11,230,702 | B2 | 1/2022 | Wicks et al. |
| 12,441,987 | B2 | 10/2025 | Tsai et al. |
| 2014/0142370 | A1 | 5/2014 | Wong et al. |
| 2016/0186146 | A1 | 6/2016 | Thomson et al. |
| 2017/0362584 | A1* | 12/2017 | Bani ..................... C12N 5/069 |
| 2018/0275147 | A1 | 9/2018 | Wellington et al. |
| 2020/0181555 | A1 | 6/2020 | Hinojosa et al. |
| 2020/0339956 | A1* | 10/2020 | Alder .................. C12N 5/0681 |

FOREIGN PATENT DOCUMENTS

| | | |
|---|---|---|
| WO | WO 2018/027112 A1 | 2/2018 |
| WO | WO 2018/048976 A1 | 3/2018 |
| WO | WO 2019/195798 A1 | 10/2019 |
| WO | WO 2021/077064 A1 | 4/2021 |

OTHER PUBLICATIONS

Helms et al (Journal of Cerebral Blood Flow & Metabolism 2016, vol. 36(5) 862-890, DOI: 10.1177/0271678X16630991) (Year: 2016).*
Jamieson et al (Journal of Biological Engineering (2017) 11:37, DOI 10.1186/s13036-017-0076-1) (Year: 2017).*
Urich et al (Scientific Reports | 3 : 1500 | DOI: 10.1038/srep01500) (Year: 2013).*
Gaston et al (Journal of Healthcare Engineering vol. 2017, Article ID 5740975, 10 pages https://doi.org/10.1155/2017/5740975). (Year: 2017).*
Yan et al (Theranostics 2021, vol. 11, Issue 20, 10148-10170. doi: 10.7150/thno.63195) (Year: 2021).*
Gastfriend et al (Curr Opin Biomed Eng. Mar. 2018 ; 5: 6-12. doi:10.1016/j.cobme.2017.11.002.) (Year: 2018).*
Kataoka (Int. J. Mol. Sci. 2016, 17, 1306; doi:10.3390/ijms17081306) (Year: 2016).*
Thomsen et al (J. Neurochem. (2017) 140, 741-754, doi: 10.1111/jnc.13747) (Year: 2017).*
Campisi et al (Biomaterials 180 (2018) 117e129, Doi: 10.1016/j.biomaterials.2018.07.014) (Year: 2018).*
Burkhart et al (Fluids Barriers CNS (2015) 12:19, DOI 10.1186/s12987-015-0015-9 ). (Year: 2015).*
Lippmann et al (Scientific Reports | 4 : 4160 | DOI: 10.1038/srep04160, Published Feb. 24, 2014). (Year: 2014).*
Nakamura et al (J. Cell Biol. 2019 vol. 218 No. 10 3506-3525, doi: 10.1083/jcb.201807178) (Year: 2019).*

(Continued)

*Primary Examiner* — Peter Paras, Jr.
*Assistant Examiner* — Khoa Nhat Tran
(74) *Attorney, Agent, or Firm* — Wolf, Greenfield & Sacks, P.C.

(57) ABSTRACT

The present disclosure provides, in some embodiments, in vitro blood brain barrier (iBBB) having functional properties of in vivo BBB as well as methods of identifying compounds capable of traversing the iBBB. Compounds capable of crossing the iBBB and therapeutic uses of such compounds are also described.

15 Claims, 48 Drawing Sheets

(56) References Cited

OTHER PUBLICATIONS

Wang et al (Mol. Pharmaceutics 2016, 13, 895-906, DOI: 10.1021/acs.molpharmaceut.5b00805) (Year: 2016).*
Destefano et al (Fluids Barriers CNS (2018) 15:32 , Doi:10.1186/s12987-018-0117-2). (Year: 2018).*
International Search Report and Written Opinion for PCT/US2020/014572, mailed Jul. 7, 2020.
International Preliminary Report on Patentability for PCT/US2020/014572, mailed Aug. 5, 2021.
Invitation to Pay Additional Fees for PCT/US2020/014572, mailed May 15, 2020.
Blanchard et al., Unraveling the Paradox of Statins with Human Neurons: New Leads in Alzheimer's Disease. Cell Stem Cell. Mar. 7, 2019;24(3):347-349. doi: 10.1016/j.stem.2019.02.003. PMID: 30849361.
Dewitt et al., "Diversomers": an approach to nonpeptide, nonoligomeric chemical diversity. Proc Natl Acad Sci U S A. Aug. 1, 1993;90(15):6909-13.
Erb et al., Recursive deconvolution of combinatorial chemical libraries. Proc Natl Acad Sci U S A. Nov. 22, 1994;91(24):11422-6. doi: 10.1073/pnas.91.24.11422.
Herland et al., Distinct Contributions of Astrocytes and Pericytes to Neuroinflammation Identified in a 3D Human Blood-Brain Barrier on a Chip. PLoS One. Mar. 1, 2016;11(3):e0150360. doi: 10.1371/journal.pone.0150360. PMID: 26930059; PMCID: PMC4773137.
Lippmann et al., A retinoic acid-enhanced, multicellular human blood-brain barrier model derived from stem cell sources. Sci Rep. Feb. 24, 2014;4:4160. doi: 10.1038/srep04160. PMID: 24561821; PMCID: PMC3932448.
Page et al., Neurological diseases at the blood-brain barrier: Stemming new scientific paradigms using patient-derived induced pluripotent cells. Biochim Biophys Acta Mol Basis Dis. Apr. 1, 2020;1866(4):165358. doi: 10.1016/j.bbadis.2018.12.009. Epub Dec. 26, 2018. PMID: 30593893.
Penney et al., Modeling Alzheimer's disease with iPSC-derived brain cells. Mol Psychiatry. Jan. 2020;25(1):148-167. doi: 10.1038/s41380-019-0468-3. Epub Aug. 7, 2019. PMID: 31391546; PMCID: PMC6906186.
Sivandzade et al., In-vitro blood-brain barrier modeling: A review of modern and fast-advancing technologies. J Cereb Blood Flow Metab. Oct. 2018;38(10):1667-1681. doi: 10.1177/0271678X18788769. Epub Jul. 30, 2018. PMID: 30058456; PMCID: PMC6168917.
Urich et al., Multicellular self-assembled spheroidal model of the blood brain barrier. Sci Rep. 2013;3:1500. doi: 10.1038/srep01500.
Vatine et al., Human iPSC-Derived Blood-Brain Barrier Chips Enable Disease Modeling and Personalized Medicine Applications. Cell Stem Cell. Jun. 6, 2019;24(6):995-1005.e6. doi: 10.1016/j.stem.2019.05.011. PMID: 31173718.
Abud et al., iPSC-Derived Human Microglia-like Cells to Study Neurological Diseases. Neuron. Apr. 19, 2017;94(2):278-293.e9. doi: 10.1016/j.neuron.2017.03.042.
Achyuta et al., A modular approach to create a neurovascular unit-on-a-chip. Lab Chip. Feb. 21, 2013;13(4):542-53. doi: 10.1039/c2lc41033h. PMID: 23108480.
Armulik et al., Pericytes regulate the blood-brain barrier. Nature. Nov. 25, 2010;468(7323):557-61. doi: 10.1038/nature09522. Epub Oct. 13, 2010.
Bang et al., Emerging Brain-Pathophysiology-Mimetic Platforms for Studying Neurodegenerative Diseases: Brain Organoids and Brains-on-a-Chip. Adv Healthc Mater. Jun. 2021;10(12):e2002119. doi: 10.1002/adhm.202002119. Epub May 24, 2021. PMID: 34028201.
Bergmann et al., Blood-brain-barrier organoids for investigating the permeability of CNS therapeutics. Nat Protoc. Dec. 2018;13(12):2827-2843. doi: 10.1038/s41596-018-0066-x. PMID: 30382243; PMCID: PMC6673652.
Blanchard et al., Reconstruction of the human blood-brain barrier in vitro reveals a pathogenic mechanism of APOE4 in pericytes. Nat Med. Jun. 2020;26(6):952-963. doi: 10.1038/s41591-020-0886-4. Epub Jun. 8, 2020. Erratum in: Nat Med. Feb. 2021;27(2):356. doi: 10.1038/s41591-021-01250-8. Author Manuscript, 37 pages.
Brown et al., Recreating blood-brain barrier physiology and structure on chip: A novel neurovascular microfluidic bioreactor. Biomicrofluidics. Oct. 26, 2015;9(5):054124. doi: 10.1063/1.4934713.
Deli et al., Permeability studies on in vitro blood-brain barrier models: physiology, pathology, and pharmacology. Cell Mol Neurobiol. Feb. 2005;25(1):59-127. doi: 10.1007/s10571-004-1377-8.
Feletou M, The Endothelium: Part 1: Multiple Functions of the Endothelial Cells—Focus on Endothelium-Derived Vasoactive Mediators. San Rafael (CA): Morgan & Claypool Life Sciences; 2011.
Ferro et al., Materials for blood brain barrier modeling in vitro. Mater Sci Eng R Rep. Apr. 2020;140:100522. doi: 10.1016/j.mser.2019.100522. Epub Jan. 6, 2020.
Hatherell et al., Development of a three-dimensional, all-human in vitro model of the blood-brain barrier using mono-, co-, and tri-cultivation Transwell models. J Neurosci Methods. Aug. 15, 2011;199(2):223-9. doi: 10.1016/j.jneumeth.2011.05.012. Epub May 14, 2011. PMID: 21609734.
Karow et al., Reprogramming of pericyte-derived cells of the adult human brain into induced neuronal cells. Cell Stem Cell. Oct. 5, 2012;11(4):471-6. doi: 10.1016/j.stem.2012.07.007.
Kazmi et al., Cyclic undecapeptide Cyclosporin A mediated inhibition of amyloid synthesis: Implications in alleviation of amyloid induced neurotoxicity. Sci Rep. Nov. 23, 2018;8(1):17283. doi: 10.1038/s41598-018-35645-4.
Kumar et al., Specification and Diversification of Pericytes and Smooth Muscle Cells from Mesenchymoangioblasts. Cell Rep. May 30, 2017;19(9):1902-1916. doi: 10.1016/j.celrep.2017.05.019. Author Manuscript, 28 pages.
Lee et al., Extracellular matrix protein 1 regulates cell proliferation and trastuzumab resistance through activation of epidermal growth factor signaling. Breast Cancer Res. Dec. 11, 2014;16(6):479. doi: 10.1186/s13058-014-0479-6. Erratum in: Breast Cancer Res. Mar. 26, 2019;21(1):45. doi: 10.1186/s13058-019-1106-3.
Li et al., Toward a neurospheroid niche model: optimizing embedded 3D bioprinting for fabrication of neurospheroid brain-like co-culture constructs. Biofabrication. Nov. 10, 2020;13(1):10.1088/1758-5090/abc1be. doi: 10.1088/1758-5090/abc1be. PMID: 33059333; PMCID: PMC8387028.
Lin et al., APOE4 Causes Widespread Molecular and Cellular Alterations Associated with Alzheimer's Disease Phenotypes in Human iPSC-Derived Brain Cell Types. Neuron. Jun. 27, 2018;98(6):1141-1154.e7. doi: 10.1016/j.neuron.2018.05.008. Epub May 31, 2018. Erratum in: Neuron. Jun. 27, 2018;98(6):1294. doi: 10.1016/j.neuron.2018.06.011.
Lippmann et al., Modeling the blood-brain barrier using stem cell sources. Fluids Barriers CNS. Jan. 10, 2013;10(1):2. doi: 10.1186/2045-8118-10-2.
Logan et al., Studying Human Neurological Disorders Using Induced Pluripotent Stem Cells: From 2D Monolayer to 3D Organoid and Blood Brain Barrier Models. Compr Physiol. Mar. 14, 2019;9(2):565-611. doi: 10.1002/cphy.c180025. PMID: 30873582; PMCID: PMC6705133.
Oberheim et al., Uniquely hominid features of adult human astrocytes. J Neurosci. Mar. 11, 2009;29(10):3276-87. doi: 10.1523/JNEUROSCI.4707-08.2009.
Osaki et al., Engineered 3D vascular and neuronal networks in a microfluidic platform. Sci Rep. Mar. 26, 2018;8(1):5168.
Ozerdem et al., NG2 proteoglycan is expressed exclusively by mural cells during vascular morphogenesis. Dev Dyn. Oct. 2001;222(2):218-27. doi: 10.1002/dvdy.1200.
Patsch et al., Generation of vascular endothelial and smooth muscle cells from human pluripotent stem cells. Nat Cell Biol. Aug. 2015;17(8):994-1003. doi: 10.1038/ncb3205. Epub Jul. 27, 2015. Author Manuscript, 22 pages.
Qian et al., Directed differentiation of human pluripotent stem cells to blood-brain barrier endothelial cells. Sci Adv. Nov. 8, 2017;3(11):e1701679. doi: 10.1126/sciadv.1701679.
Rojanathammanee et al., Attenuation of microglial activation in a mouse model of Alzheimer's disease via NFAT inhibition. J Neuroinflammation. Mar. 4, 2015;12:42. doi: 10.1186/s12974-015-0255-2.

(56) References Cited

OTHER PUBLICATIONS

Seo et al., Oligodendrocyte precursor cells support blood-brain barrier integrity via TGF-β signaling. PLoS One. Jul. 31, 2014;9(7):e103174. doi: 10.1371/journal.pone.0103174.
Sokolova et al., Ultrasmall gold nanoparticles (2 nm) can penetrate and enter cell nuclei in an in vitro 3D brain spheroid model. Acta Biomater. Jul. 15, 2020;111:349-362. doi: 10.1016/j.actbio.2020.04.023. Epub May 13, 2020. PMID: 32413579.
Tan et al., Human mini-brain models. Nat Biomed Eng. Jan. 2021;5(1):11-25. doi: 10.1038/s41551-020-00643-3. Epub Dec. 14, 2020. PMID: 33318650.
Tang-Schomer et al., In vitro 3D regeneration-like growth of human patient brain tissue. J Tissue Eng Regen Med. May 2018;12(5):1247-1260. doi: 10.1002/term.2657. Epub Apr. 6, 2018. PMID: 29509306.
Tate et al., Assessing drug response in engineered brain microenvironments. Brain Res Bull. Aug. 2019;150:21-34. doi: 10.1016/j.brainresbull.2019.04.027. Epub May 1, 2019. PMID: 31054318; PMCID: PMC6754984.
Urich et al., Transcriptional profiling of human brain endothelial cells reveals key properties crucial for predictive in vitro blood-brain barrier models. PLoS One. 2012;7(5):e38149. doi: 10.1371/journal.pone.0038149. Epub May 31, 2012.
Yamazaki et al., ApoE (Apolipoprotein E) in Brain Pericytes Regulates Endothelial Function in an Isoform-Dependent Manner by Modulating Basement Membrane Components. Arterioscler Thromb Vasc Biol. Jan. 2020;40(1):128-144. doi: 10.1161/ATVBAHA.119.313169. Epub Oct. 31, 2019.
Zhang et al., An RNA-sequencing transcriptome and splicing database of glia, neurons, and vascular cells of the cerebral cortex. J Neurosci. Sep. 3, 2014;34(36):11929-47. doi: 10.1523/JNEUROSCI.1860-14.2014. Erratum in: J Neurosci. Jan. 14, 2015;35(2):846-6.

* cited by examiner

CD144/CD31/DAPI

ZO1/GLUT1/DAPI

GFAP/DAPI

GFAP/S100β/DAPI

S100β/AQP4/DAPI

Up regulated Biological processes

| | ID | Name | pValue | FDR B&H | FDR B&Y | Bonferroni | Genes from Input | Genes in Annotation |
|---|---|---|---|---|---|---|---|---|
| 1 | GO:0006614 | SRP-dependent cotranslational protein targeting to membrane | 1.16E-59 | 1.09E-55 | 1.06E-54 | 1.09E-55 | 79 | 94 |
| 2 | GO:0006613 | cotranslational protein targeting to membrane | 5.70E-58 | 2.66E-54 | 2.59E-53 | 5.32E-54 | 81 | 101 |
| 3 | GO:0045047 | protein targeting to ER | 2.07E-54 | 6.46E-51 | 6.28E-50 | 1.94E-50 | 79 | 102 |
| 4 | GO:0072599 | establishment of protein localization to endoplasmic reticulum | 1.54E-53 | 3.61E-50 | 3.51E-49 | 1.44E-49 | 80 | 106 |
| 5 | GO:0070972 | protein localization to endoplasmic reticulum | 1.02E-50 | 1.91E-47 | 1.86E-46 | 9.56E-47 | 85 | 125 |

FIG. 10A

Down regulated Biological processes

| | ID | Name | pValue | FDR B&H | FDR B&Y | Bonferroni | Genes from Input | Genes in Annotation |
|---|---|---|---|---|---|---|---|---|
| 1 | GO:1903047 | mitotic cell cycle process | 4.27E-28 | 2.32E-24 | 2.23E-23 | 3.55E-24 | 200 | 931 |
| 2 | GO:0000278 | mitotic cell cycle | 5.59E-28 | 2.32E-24 | 2.23E-23 | 4.65E-24 | 212 | 1016 |
| 3 | GO:0022402 | cell cycle process | 5.49E-25 | 1.52E-21 | 1.46E-20 | 4.57E-21 | 255 | 1385 |
| 4 | GO:0007049 | cell cycle | 3.37E-24 | 7.00E-21 | 6.72E-20 | 2.80E-20 | 302 | 1766 |
| 5 | GO:0000280 | nuclear division | 5.35E-22 | 8.90E-19 | 8.55E-18 | 4.45E-18 | 137 | 599 |

FIG. 10B 1881 genes

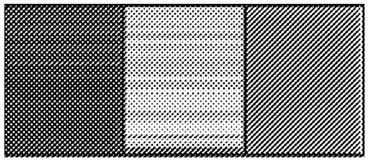

| | | | |
|---|---|---|---|
| 1. | GO:0043087 | regulation of GTPase activity | p = 6.051E-12 |
| 2. | GO:0051056 | regulation of small GTPase mediated signal transduction | p = 1.490E-11 |
| 3. | GO:0043547 | positive regulation of GTPase activity | p = 1.781E-10 |
| 4. | GO:0007264 | small GTPase mediated signal transduction | p = 1.787E-9 |
| 5. | GO:0001843 | neural tube closure | p = 1.820E-9 |

2783 genes

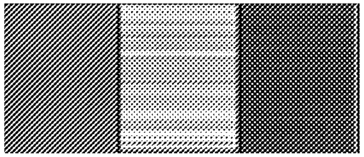

| | | | |
|---|---|---|---|
| 1. | GO:0006886 | intracellular protein transport | p = 1.648E-22 |
| 2. | GO:0015031 | protein transport | p = 3.090E-22 |
| 3. | GO:0034613 | cellular protein localization | p = 2.729E-21 |
| 4. | GO:0044248 | cellular catabolic process | p = 4.278E-21 |
| 5. | GO:0070727 | cellular macromolecule localization | p = 6.733E-21 |

860 genes

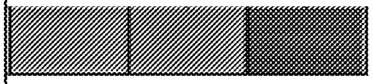

| | | | |
|---|---|---|---|
| 1. | GO:0006396 | RNA processing | p = 7.016E-17 |
| 2. | GO:0034660 | ncRNA metabolic process | p = 8.151E-16 |
| 3. | GO:0043604 | amide biosynthetic process | p = 8.504E-13 |
| 4. | GO:0043043 | peptide biosynthetic process | p = 1.233E-12 |
| 5. | GO:0016071 | mRNA metabolic process | p = 8.155E-12 |

FIG. 12E

$APOE_4$ increases permeability of the iBBB

APOE$_4$ increases permeability of the iBBB

APOE4 appears to increase permeability of iBBB to Ab42

*In vivo* Cyclosporine A reduces APOE in and around cortical pericytes

*In vivo* Cyclosporine A reduces APOE and Vascular Amyloid

Hippocampus Vasculature in APOE4KI X 5xFAD mice

Both FK506 and Cyclosporine A reduces Vascular Amyloid *In Vivo*

IN VITRO HUMAN BLOOD BRAIN BARRIER

RELATED APPLICATIONS

This application is a national stage filing under 35 U.S.C. § 371 of International Patent Application Serial No. PCT/US2020/014572, which claims priority under 35 U.S.C. 119(e) to U.S. provisional patent application, U.S. Ser. No. 62/795,520, filed Jan. 22, 2019, each of which is incorporated herein by reference in its entirety.

GOVERNMENT SUPPORT

This invention was made with Government support under Grant No. U54 HG008097 awarded by the National Institutes of Health (NIH). The Government has certain rights in the invention.

BACKGROUND

Vascular endothelial cells in the brain form a highly selective barrier that regulates the exchange of molecules between the central nervous system and the periphery. This blood-brain barrier (BBB) is critical for proper neuronal function, protecting the brain from pathogens and tightly regulating the composition of extracellular fluid. The BBB is thought to play a prominent role in neurodegeneration and aging. Most Alzheimer's disease (AD) patients and 20-40% of non-demented elderly experience Aβ deposits along their cerebral vasculature a condition known as CAA. Cerebrovascular amyloid deposition impairs BBB function; as a result individuals with CAA are prone to cerebral ischemia, microbleeds, hemorrhagic stroke, infection, which ultimately lead to neurodegeneration and cognitive deficits.

SUMMARY

The present disclosure is based, at least in part, on the development of a 3 dimensional (3D) model of blood brain barrier which effectively mimics a capillary environment. Surprisingly the model provides an accurate system for assessing the development of amyloid plaques and thus, provides a useful system for identifying and screening compounds which are effective in reducing amyloid accumulation.

Accordingly, one aspect of the present disclosure provides an in vitro blood brain barrier (iBBB) comprising a 3 dimensional (3D) matrix of a human brain endothelial cell (BEC) vessel comprised of a large interconnected network of human pluripotent-derived positive endothelial cells encapsulated in the 3D matrix, human pluripotent-derived pericytes proximal to the BEC vessel on an apical surface, and human pluripotent-derived astrocytes dispersed throughout the 3D matrix, wherein a plurality of the astrocytes are proximal to the BEC vessel and have GFAP-positive projections into the perivascular space.

In another aspect, an in vitro blood brain barrier (iBBB) comprising a 3 dimensional (3D) matrix is provided. The iBBB has a human brain endothelial cell (BEC) vessel comprised of a large interconnected network of endothelial cells encapsulated in a 3D matrix, pericytes proximal to the BEC vessel on an apical surface, wherein the pericytes have an E4/E4 genotype, and astrocytes proximal to the BEC vessel, wherein a plurality of the astrocytes have positive projections into the perivascular space.

In some embodiments, the astrocytes express AQP4. In some embodiments, the 3D matrix comprises LAMA4. In some embodiments, the BEC express at least any one of JAMA, PgP, LRP1, and RAGE. In some embodiments, PgP and ABCG2 are expressed on the apical surface. In some embodiments, levels of PgP and ABCG2 expressed on the apical surface are 2-3 times greater than levels of PgP and ABCG2 expressed on BEC cultured alone or co-cultured with astrocytes. In some embodiments, the iBBB has a TEER that exceeds 5,500 Ohm×cm2, exhibits reduced molecular permeability and polarization of efflux pumps relative to BEC cultured alone or co-cultured with astrocytes. In some embodiments, the iBBB is not cultured with retinoic acid.

In some embodiments, the human pluripotent are iPSC-derived CD144 cells. In other embodiments the iBBB is generated using 5 parts endothelial cells to 1 part astrocytes to 1 part pericytes. In yet other embodiments the iBBB is generated using about 1 million endothelial cells per ml, about 200,000 astrocytes per ml and about 200,000 pericytes per ml.

In some embodiments, the iBBB has a size similar to a capillary. In some embodiments, the iBBB is 5 to 50 microns in length. In some embodiments, the iBBB is 5 to 30 microns in length. In some embodiments, the iBBB is 10 to 20 microns in length. In some embodiments, the BEC vessel is a capillary size. In other embodiments, the iBBB is 3-50 microns, 5-45 microns, 5-40 microns, 5-35 microns, 5-30 microns, 5-25 microns, 5-20 microns, 5-15 microns, 5-10 microns, 8-50 microns, 8-45 microns, 8-40 microns, 8-35 microns, 8-30 microns, 8-25 microns, 8-20 microns, 8-15 microns, 8-10 microns, 10-50 microns, 10-45 microns, 10-40 microns, 10-35 microns, 10-30 microns, 10-25 microns, 10-20 microns, 10-15 microns, or 10-12 microns in length.

A method for identifying an effect of a compound on a blood brain barrier, by providing an iBBB, such as that described herein, contacting the BEC vessel of the iBBB with a compound, and detecting the effect of the compound on the iBBB relative to an iBBB which has not been contacted with the compound is provided in other aspects of the invention.

In some embodiments, the effect of the compound on the iBBB is measured as a change in expression of an extracellular matrix factor. In some embodiments, the effect of the compound on the iBBB is measured as a change in expression of a gene. In some embodiments, the effect of the compound on the iBBB is measured as a change in expression of a soluble factor. In some embodiments, the compound alters one or more functional properties of the iBBB. In some embodiments, the functional properties of the iBBB are cell migration, molecular permeability or polarization of efflux pumps. In some embodiments, the effect of the compound on the iBBB is measured as a change in amyloid deposits.

In other aspects a method is provided for identifying an inhibitor of amyloid-β peptide (Aβ) production and/or accumulation, by contacting an Aβ producing cell with an APOE4 positive pericyte factor and at least one candidate inhibitor and detecting an amount of Aβ in the presence and absence of the candidate inhibitor, wherein a reduced quantity of Aβ associated with the cell in the presence of the candidate inhibitor relative an amount of Aβ associated with the cell in the absence of the candidate inhibitor indicates that the candidate inhibitor is an inhibitor of Aβ.

In some embodiments, the APOE4 positive pericyte factor is a soluble factor in APOE4 pericyte conditioned media. In some embodiments, the soluble factor is APOE protein. In some embodiments, the APOE4 positive pericyte factor is APOE protein produced by pericytes. In some embodiments, the Aβ producing cell expressed APOE3. In some embodiments, the Aβ producing cell has an APOE3/3 genotype or an APOE3/4 genotype. In some embodiments, the Aβ producing cell is an APOE4 positive pericyte. In some embodiments, the pericyte has an APOE4/4 genotype. In some embodiments, the pericyte has an APOE3/4 genotype. In some embodiments, the APOE4 positive pericyte factor is a soluble factor produced by an APOE4 pericyte co-incubated with the Aβ producing cell. In some embodiments, the Aβ producing cell is an astrocyte or an endothelial cell. In some embodiments, the method further comprises providing an iBBB as described herein, contacting the BEC vessel of the iBBB with the inhibitor of Aβ, and detecting the effect of the inhibitor of Aβ on the production of Aβ by the iBBB relative to an iBBB which has not been contacted with the inhibitor of Aβ.

In some aspects a method for inhibiting amyloid synthesis in a subject is provided. The method involves determining whether a subject has or is at risk of developing amyloid accumulation by identifying the subject as APOE4 positive, if the subject is APOE4 positive, administering to the subject an inhibitor of calcineurin/NFAT pathway in an effective amount to inhibit amyloid synthesis in the subject. In some embodiments the inhibitor of calcineurin/NFAT pathway is not cyclosporin.

In other aspects a method for inhibiting amyloid synthesis in a subject by administering to the subject having or at risk of having CAA an inhibitor of calcineurin/NFAT pathway in an effective amount to inhibit amyloid synthesis in the subject, wherein the inhibitor of calcineurin/NFAT pathway is not cyclosporin is provided.

In other aspects a method for inhibiting amyloid synthesis in a subject by administering to the subject an inhibitor of C/EBP pathway in an effective amount to inhibit amyloid synthesis in the subject.

In some embodiments the subject has CAA. In some embodiments the subject has Alzheimer's disease. In some embodiments the subject has not been diagnosed with Alzheimer's disease. In some embodiments does not have Alzheimer's disease.

In some embodiments the inhibitor of calcineurin/NFAT pathway is a small molecule inhibitor. In some embodiments the inhibitor of calcineurin/NFAT pathway is FK506. In some embodiments the inhibitor of calcineurin/NFAT pathway is cyclosporin.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIGS. 10A-10H. 10A and 10B, GO analysis (from Toppfun) depicting biological processes associated with up-regulated (a) and down-regulated (b) genes. 10C and 10D, Expression of APOE in isogenic pericytes (c) and astrocyte (d) measured by RNA sequencing each condition represents three biological replicates pericyte, q=0.0003 astrocyte, q=0.0006 10E Violin plots depicting APOE expression in pericytes isolated from post-mortem prefrontal cortex of APOE4-carriers (n=7) compared to non-carriers (n=18). Differential expression was measured using a two-tailed Wilcoxon rank sum test, considering cells with detected expression of APOE (p=0.0026). '0F, Images and quantification of APOE protein expression in post-mortem human prefrontal cortex from APOE4 carriers and non-carriers. Unpaired two-tailed t test (p=0.023). 10G, Differential plot of representative maker genes showing that pericytes and endothelial cells isolated from human hippocampus segregated into distinct cellular clusters 10H, Violin plots depicting APOE expression in endothelial cells isolated from post-mortem hippocampus APOE4-carriers (n=16) compared to non-carriers (n=46). Differential expression was measured using a two-tailed Wilcoxon rank sum test, considering cells with detected expression of APOE.

FIGS. 12A-12K. 12A, Chemical structures of CsA, FK506, and INCA6 showing highly dissimilar structures. 12B, Expression of PGK1, HPRT, and GAPDH in pericytes after two weeks with DMSO, Cyclosporine A (CsA), FK506 or INCA6. One-way ANOVA (p<0.0001) with Bonferroni's multiple comparison. 12C and 12D, Representative immunofluorescence imaging of APOE protein staining in pericytes after two weeks of treatment with chemicals. Scale bar, 50 μm. 12E DEGs and associated GO terms for up-regulated and down-regulated genes in E3 and E4 CsA-treated pericytes. 12F and 12G. Representative imaging and quantification depicting APOE protein expression in the APOE4KI mouse cortical slices following treatment with cyclosporine A (CsA) for one week. Unpaired, two tailed t test (p=0.0009). 12H, Quantification of amyloid APOE4KI mouse cortical slices treated with either CsA or FK506 for one week and then exposed to 20 nM Aβ for 48 hours. One-way ANOVA (p=0.0105) with Bonferroni's multiple comparison. 12I, APOE mRNA expression in primary pericytes isolated from brain microvasculature of APOE4 knock-in mice treated with DMSO, Cyclosporine A, or FK506. One-way ANOVA (p=0.0139) with Bonferroni's multiple comparison. 12J, Representative image of immunostaining for APOE in hippocampal pericytes from APOE4 KI×5XFAD mice treated with cyclosporine A or vehicle for one week. 12K, Representative images of vascular amyloid in the hippocampus following treatment of 6-month-old APOE4KI×5XFAD female mice with either vehicle or CsA. Amyloid was detected and quantified with two independent anti-amyloid antibodies (6e10 and 12F4).

DETAILED DESCRIPTION

Figure 1A:
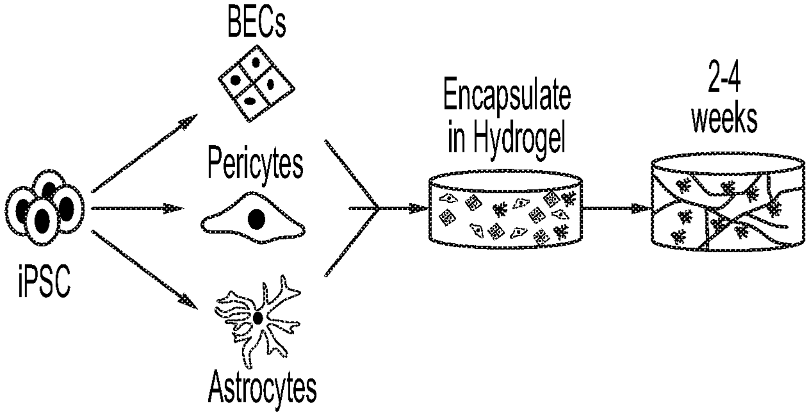
FIGS. 1A-1O. Reconstruction of Anatomical and Physiological Properties of the Human Blood-brain-barrier in vitro (iBBB). 1A, Schematic of iBBB formation from iPSCs. 1B, iBBB stained for endothelial cell marker CD144 demonstrating the presence of multicellular endothelial vessels. Scale bar, 50 μm. 1C, Pericytes localize to endothelial vessels after two weeks in culture. Pericytes are labeled with SM22 (also known as TAGLN) and BEC labeled with tight junction protein ZO-1. Scale bar, 50 μm. 1D, Pericytes are labeled with NG2 and BECs with CD144. 1E, Astrocytes surround endothelial vessels after two weeks in culture. Astrocytes are labeled with GFAP and BECs are labeled with CD144. Scale bar, 50 μm. 1F, Aquaporin 4 (AQP4), is expressed on BEC vessels labeled with ZO-1, pan-astrocyte marker S100β. Scale bar, 50 μm. 1G, qRT-PCR measuring the expression of genes reported to be predictive markers of BBB models. All expression is normalized to pan-endothelial marker PECAM to account for potential differences in BEC cell number. CLDN, RAGE, JAMA, and LRP1; $p<0.0001$. PgP; $p=0.0001$, GLUT1; $p=0.0032$. 1H, qRT-PCR measuring the expression of transporters, adhesion molecules, and efflux-pumps, and tight-junctions found in the BBB. All expression levels are normalized to BECs alone. Y-axis is the expression level in BECs isolated from the iBBB normalized to BECs cultured alone. X-axis is BECs co-cultured with astrocytes normalized to BECs cultured alone. Circles represent means from three biological replicates and three PCR replicates. 1I, Cartoon depicting transwell setup for measuring iBBB permeability 1J, Representative image of BECs (ZO-1), pericytes (SM22) and astrocytes (S100β) co-cultured on transwell membrane. 1K, Trans-endothelial electrical resistance (TEER) measurements from HuVECs, HuVECs plus pericytes (P) and astrocytes (A), BECs only and the iBBB. Circles represent single measurements from individual transwells. Differences were analyzed by one-way ANOVA with Bonferroni's post-hoc analysis ($p<0.0001$). 1L, Permeability of fluorescently labeled molecules for BECs alone or iBBB. All values are reported as a percent of each molecule's permeability across a blank transwell membrane. Stars represent significance determined by multiple student's t-test (FDR=0.01). 1M, BBB properties of the iBBB require cooperative interaction of pericytes and astrocytes. The permeability of 4 kDa dextran was quantified in the iBBB and compared to BECs with 2× pericytes, 2× astrocytes, or BECs with mouse embryonic fibroblasts (MEFs). Permeability is normalized to BECs alone. One-way ANOVA ($p<0.0001$) with Bonferroni's multiple comparisons. 1N, ABCG2 expression is up-regulated in the iBBB. One-way ANOVA with Bonferroni's post-hoc analysis ($p<0.0001$). 1O, Polarization of Pgp was measured by rhodamine 123 transport for both a BECs monolayer and the iBBB from the apical to basolateral surface and vice versa. Inhibitor-treated samples were normalized to each respective non-inhibitor-treated sample. Stars represent significance determined by multiple student's t-tests (FDR=0.01).

A human 3D in vitro model of the BBB (iBBB) which recapitulates numerous molecular and physiological features of the in vivo BBB has been developed. The iBBB is a unique model of a capillary system which allows for the analysis of capillary transport and activity. Prior art artificial BBBs have typically been 2 dimensional systems and/or of a larger size that more closely mimics a larger vessel. The iBBB of the invention provides advantages not previously found in prior art devices.

As described in further detail in the Examples, the iBBB has been developed and extensively studied herein. It's relevance to the physiologic system has been established through extensive analysis and characterization. The iBBB was further designed and validated as a neurodegenerative model. This was through the elucidation of the mechanisms underlying one of the strongest genetic risks factor (APOE4) for cerebrovascular amyloid accumulation. The data generated and described herein using the iBBB revealed that pericytes, the smooth muscle component of cerebral vasculature, are required for the pathogenic effects of APOE4. Subsequent mechanistic dissection pinpointed that APOE itself is highly up-regulated in APOE4 pericytes and that up-regulation is required for increased amyloid accumulation. Using post-mortem human brain tissue, it was confirmed that APOE is also upregulated in human brain pericytes of APOE4 carriers compared to non-carriers. Global transcriptional profiling further revealed that CaN/NFAT signaling in E4 pericytes is highly active. It was further demonstrated that pharmacological inhibition of CaN/NFAT signaling markedly reduced APOE expression in the iBBB and in vivo mouse brain and rescues the pathological amyloid phenotype observed in APOE4 iBBBs. These findings have profound implications for the treatment, diagnosis and further analysis of cerebral amyloid angiopathy (CAA). CAA is a form of angiopathy in which amyloid beta (Aβ) peptide is deposited in the walls of small to medium blood vessels of the central nervous system and meninges. The buildup of Aβ is associated with cognitive decline.

NFAT/CaN signaling is up-regulated during cognitive aging and neurodegeneration. In aged rats, up-regulation of CaN leads to poor cognitive performance. Despite the correlation of up-regulated NFAT/CaN signaling in neurodegeneration it remains unknown whether NFAT/CaN has a causal role in neurodegeneration. Uncertainty surrounding whether CaN and NFAT are viable targets for treatment of neurodegenerative disease such as Alzheimer's disease (AD) and who would benefit from these treatments has limited the development of therapeutic strategies in this area. The results described herein, provide significant advances in understanding the system and identifying therapeutic targets for the treatment of disease associated with Aβ deposition on small vessels. The data identify the cell-type (pericytes), soluble factor (APOE), and regulatory pathway (calcineurin/NFAT) through which APOE4 acts to predispose CAA pathology. The iBBB was also demonstrated to model genotype-related differences in BBB permeability. The relevance of these observations to human neurobiology was further validated using post-mortem human brain tissue and mouse models to demonstrate that these cellular and molecular insights can be translated to an in vivo setting for therapeutic intervention. Through multiple lines of evidence, the iBBB has been shown to be a tractable model and provide biological insight into how genetic variants can influence cerebral vascular pathology, thereby opening new therapeutic opportunities. Importantly, it was shown that treatment of mice in vivo with cyclosporine A showed a significant reduction of cerebrovascular amyloid.

Thus, in some aspects, the invention is an in vitro blood brain barrier (iBBB) that is composed of a 3 dimensional (3D) matrix having human brain endothelial cell (BEC), human pluripotent-derived pericytes and human pluripotent-derived astrocytes arranged therein. The human brain endothelial cells (BECs) form a vessel comprised of a large interconnected network of human pluripotent-derived positive endothelial cells.

The vessel has a size on the order of a capillary. A capillary is an extremely small blood vessel located within the tissues of the body that transports blood. Capillaries measure in size from about 5 to 10 microns in diameter. Capillary walls are thin and are composed of endothelium. The iBBB is on the order of approximately 5 to 50 microns in length. In some embodiments, the iBBB is 5 to 30 microns in length. In some embodiments, the iBBB is 10 to 20 microns in length. In other embodiments, the iBBB is 3-50 microns, 5-45 microns, 5-40 microns, 5-35 microns, 5-30 microns, 5-25 microns, 5-20 microns, 5-15 microns, 5-10 microns, 8-50 microns, 8-45 microns, 8-40 microns, 8-35 microns, 8-30 microns, 8-25 microns, 8-20 microns, 8-15 microns, 8-10 microns, 10-50 microns, 10-45 microns, 10-40 microns, 10-35 microns, 10-30 microns, 10-25 microns, 10-20 microns, 10-15 microns, or 10-12 microns in length.

The endothelial cells, pericytes, and astrocytes are optionally human pluripotent-derived cells. For instance, the cells may be iPSC-derived cells, such as iPSC-derived CD144 positive cells. Autologous induced pluripotent stem cells (iPSCs) can be differentiated into any cell type of the three germ layers: endoderm (e.g. the stomach linking, gastrointestinal tract, lungs, etc), mesoderm (e.g. muscle, bone, blood, urogenital tissue, etc) or ectoderm (e.g. epidermal tissues and nervous system tissues). The term "pluripotent cells" refers to cells that can self-renew and proliferate while remaining in an undifferentiated state and that can, under the proper conditions, be induced to differentiate into specialized cell types. Pluripotent cells, encompass embryonic stem cells and other types of stem cells, including fetal, amniotic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection.

Pluripotent stem cells also encompasses induced pluripotent stem cells, or iPSCs, a type of pluripotent stem cell derived from a non-pluripotent cell. Examples of parent cells include somatic cells that have been reprogrammed to induce a pluripotent, undifferentiated phenotype by various means. Such "iPS" or "iPSC" cells can be created by inducing the expression of certain regulatory genes or by the exogenous application of certain proteins. Methods for the induction of iPS cells are known in the art. As used herein, hiPSCs are human induced pluripotent stem cells, and miPSCs are murine induced pluripotent stem cells.

The cells are seeded onto a 3D matrix or scaffold material. The matrix or scaffold material, may be, for instance, a hydrogel. The matrix may be formed of naturally derived biomaterials such as polysaccharides, gelatinous proteins, or ECM components comprising the following or functional variants thereof: agarose; alginate; chitosan; dextran; gelatin; laminins; collagens; hyaluronan; fibrin, and mixtures thereof. Alternatively the matrix may be a hydrogel formed of Matrigel, Myogel and Cartigel, or a combination of Matrigel, Myogel and Cartigel and a naturally derived biomaterial or biomaterials. The hydrogel may be a macromolecule of hydrophilic polymers that are linear or branched, preferably wherein the polymers are synthetic, more preferably wherein the polymers are poly(ethylene glycol) molecules and most preferably wherein the poly (ethylene glycol) molecules are selected from the group comprising: poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate) and mixtures thereof.

The 3D matrix may be generated using an optimal mixture of endothelial cells, pericytes, and astrocytes. For instance, in some embodiments the iBBB may be generated using about 5 parts endothelial cells to about 1 part astrocytes to about 1 part pericytes. In other embodiments the iBBB may be generated using about 1 million endothelial cells per ml, about 200,000 astrocytes per ml and about 200,000 pericytes per ml.

A unique feature of the 3D matrix is that the cells are seeded onto the matrix and self-assemble into a BBB like structure. The cells arrange themselves such that the BECs form a large interconnected network of cells, similar to a capillary wall. The pericytes are arranged proximal to the BEC vessel on an apical surface. The human pluripotent-derived astrocytes are dispersed throughout the 3D matrix. However some of the astrocytes are positioned proximal to the BEC vessel and have GFAP-positive projections into the perivascular space.

The iBBB has structural properties that mimic in vivo BBB tissue. In addition to the manner in which the cells assemble in the 3D structure, the iBBB and cells found therein have structural properties which are associated with in vivo BBB such as expression of specific genes associated with cells in BBB in vivo. For instance the astrocytes express AQP4 and the BEC may express at least any one of CLDN5, GLUT1, JAMA, PgP, LRP1, and RAGE. In some embodiments the BEC may express at least any one of PECAM, ABCG2, CDH5, CGN, SLC38A5, ABCG2, VWF, and SLC7A5. The cells also produce LAMA4 which has been observed in the matrix. PgP and ABCG2 have been found to be expressed on the apical surface of the iBBB. The levels of PgP and ABCG2 expressed on the apical surface are 2-3 times greater than levels of PgP and ABCG2 expressed on BEC cultured alone or co-cultured with astrocytes. These important markers demonstrate the similarity with in vivo BBB.

The iBBB also has functional properties that mimic in vivo BBB tissue. Functional properties associated with the iBBB (that mimic in vivo BBB) include, for instance, a TEER that exceeds 5,500 Ohm×$cm^2$, reduced molecular permeability and polarization of efflux pumps relative to BEC cultured alone or co-cultured with astrocytes. Trans-endothelial electrical resistance (TEER) is a measurement of electrical resistance across an endothelial monolayer that is used as a sensitive and reliable quantitative indicator of permeability. All immortalized endothelial cell lines that form barriers exhibit TEER values below 150 Ohms/$cm^2$. Likewise, peripheral endothelial cells such as human umbilical cord vascular endothelial cells (HuVECs) have relatively high permeability and thus exhibit low TEER. In agreement with these reported observations, the data presented herein demonstrate TEER values of approximately 100 Ohms/$cm^2$ when HuVECs were cultured in trans-well configuration. HuVEC TEER values did not increase by co-culturing with astrocytes or pericytes. iPSC-derived BECs cultured alone had significantly higher TEER values with an average of 5900 Ohms $cm^2$. However, the TEER values for BECs cultured alone exhibited a high degree of variability (SD=+/−2150 Ohms/$cm^2$). Co-culturing BECs with pericytes and astrocytes in the iBBB disclosed herein reduced TEER variability (SD=+/−513.9 Ohms/$cm^2$) and led to a significant increase in the average resistance (8030 Ohms $cm^2$) suggesting the iBBB is less permeable than HuVECs, or BECs cultured alone. These functional properties make the iBBB unique among capillary sized artificial BBB.

Several AD-risk genes are expressed in cells that constitute the BBB and may directly influence the accumulation and clearance of Aβ. In particular, Apolipoprotein E (APOE) protein is highly expressed in cells of the BBB. In humans, there are three genetic polymorphisms of APOE, E2, E3, and E4. The E4 isoform of APOE (APOE4) is the most significant known risk factor for CAA and sporadic AD. The genotype of the cell plays an important role in the iBBB and related assays. In some embodiments the Aβ producing cell expressed APOE3 and/or APOE4. The Aβ producing cell may have an APOE3/3 genotype or an APOE3/4 genotype or an APOE4/4 genotype. In some embodiments the cells have an APOE4/4 genotype.

The data generated herein has revealed that pericytes play an important role in the production of amyloid-β peptide (Aβ). In view of these findings, other aspects of the invention relate to methods of identifying an inhibitor of amyloid-β peptide (Aβ) production and/or accumulation, by contacting an Aβ producing cell with an APOE4 positive pericyte factor and at least one candidate inhibitor and detecting an amount of Aβ in the presence and absence of the candidate inhibitor, wherein a reduced quantity of Aβ associated with the cell in the presence of the candidate inhibitor relative an amount of Aβ associated with the cell in the absence of the candidate inhibitor indicates that the candidate inhibitor is an inhibitor of Aβ. The APOE4 positive pericyte factor may be a soluble factor in APOE4 pericyte conditioned media, such as APOE protein.

The methods may further involve contacting the BEC vessel described herein with the inhibitor of Aβ, and detecting the effect of the inhibitor of Aβ on the production of Aβ by the iBBB relative to an iBBB which has not been contacted with the inhibitor of Aβ.

The invention, in some aspects, relates to methods for inhibiting amyloid synthesis in a subject. It has been discovered that subjects having or at risk of developing amyloid accumulation can be identified based on genotype, whether they are APOE4 positive and successfully treated with compounds identified using the assays described herein. If the subject is APOE4 positive, those subjects are at risk of developing Aβ disorders such as CAA. However, those subjects are also sensitive to treatment with an inhibitor of a calcineurin/NFAT pathway. While APOE4 has previously been associated with patients that have some Aβ disorders such as Alzheimer's, this genotype has not previously been linked as a successful predictor of a calcineurin/NFAT inhibitory activity. Prior work looking at inhibitors of this pathway in diseased individuals has not shown consistent positive results in patients. The findings of the invention have provided a link between genotype and successful therapeutic utility of compounds in the calcineurin/NFAT pathway.

NFAT (nuclear factor of activated T cells) is a transcriptional activator. In its inactive state NFAT resides in the cytoplasm where it is phosphorylated. Increases in intracellular Ca2+ lead to activation of the calmodulin-dependent phosphatase calcineurin (CaN), which subsequently dephosphorylates NFAT permitting its translocation to the nucleus where it promotes gene activation. In some embodiments the NFAT inhibitor may be a calcinuerin inhibitor and/or may be lipid soluble. The NFAT inhibitor may be selected from: cyclosporin, cyclosporin derivatives, tacrolimus derivatives, pyrazoles, pyrazole derivatives, phosphatase inhibitors, S1P receptor modulators, toxins, paracetamol metabolites, fungal phenolic compounds, coronary vasodilators, phenolic adeide, flavanols, thiazole derivatives, pyrazolopyrimidine derivatives, benzothiophene derivatives, rocaglamide derivatives, diaryl triazoles, barbiturates, antipsychotics (penothiazines), serotonin antagonists, salicylic acid derivatives, phenolic compounds derived from propolis or pomegranate, imidazole derivatives, pyridinium derivatives, furanocumarins, alkaloids, triterpenoids, terpenoids, oligonucleotides, peptides, A 285222, endothall, 4-(fluoromethyl) phenylphosphate FMPP, norcantharidin, tyrphostins, okadaic acid, RCP1063, cya/cypa (cyclophilin A), isa247 (voclosporin)/cypa, $[\text{dat-sar}]^3$-cya, fk506/fkbp12, ascomyxin/fkbp12, pinecrolimus/FKBP12, 1,5-dibenzoyloxymethyl-norcantharidin, am404, btp1, btp2, dibefurin, dipyridamole, gossypol, kaempferol, lie 120, NCI3, PD 144795, Roc-1, Roc-2, Roc-3, ST 1959 (DLI111-it), thiopental, pentobarbital, thiamylal, secobarbital, trifluoperazine, tropisetron, UR-1505, WIN 53071, caffeic acid phenylethyl ester, KRM-III, YM-53792, punicalagin, imperatorin, quinolone alkaloids compounds, impres sic acid, oleanane triterpenoid, gomisin N, $CaN_{457-482}$-AID, $CaN_{424-521}$-AID, $mFATc2_{106-121}$-SPREIT, VIVIT peptide, R11-Vivit, ZIZIT cis-pro, INCA1, INCA6, INCA2, $AKAP79_{330-357}$, RCAN1, RCAN1-$4_{141-197}$-exon7, RCAN1-$4_{143-163}$-CIC peptide, RCAN1-$4_{95-118}$-SP repeat peptide, LxVPc 1 peptide, MCV1, VacA, A238L, and $A238_{200-213}$.

A calcineurin inhibitor may disrupt the activity of calcineurin directly or indirectly. In some embodiments, the calcineurin inhibitor is cyclosporine A, FK506 (tacrolimus), pimecrolimus, or a cyclosporine analog, such as voclosporin. Cyclosporine A and FK506 are both clinically prescribed as immunosuppressants following organ transplantation. Other calcineurin inhibitors are known in the art. For instance, others are disclosed in US 2019/0085040, A calcineurin/NFAT pathway inhibitor, as used herein, is a compound that disrupts the activity of the NFAT pathway. Exemplary calcineurin/NFAT inhibitors include, but are not limited to, peptides such as antibodies small molecule compounds, and other compounds which may disrupt interactions. Calcineurin/NFAT inhibitors also include small molecule inhibitors that directly inhibit one or more components of the calcineurin/NFAT, or other agents that inhibit the binding interaction. In some embodiments the small molecule inhibitors are Cyclosporin or FK506.

The calcineurin/NFAT inhibitory compounds of the invention may exhibit any one or more of the following characteristics: (a) reduces activity of the NFAT pathway; (b) prevents, ameliorates, or treats any aspect of a neurodegenerative disease; (c) reduces synaptic dysfunction; (d) reduces cognitive dysfunction; and (e) reduces amyloid-β peptide (Aβ) accumulation. One skilled in the art can prepare such inhibitory compounds using the guidance provided herein.

The terms reduce, interfere, inhibit, and suppress refer to a partial or complete decrease in activity levels relative to an activity level typical of the absence of the inhibitor. For instance, the decrease may be by at least 20%, 50%, 70%, 85%, 90%, 100%, 150%, 200%, 300%, or 500%, or by 10-fold, 20-fold, 50-fold, 100-fold, 1000-fold, or $10^4$-fold.

In other embodiments, the calcineurin/NFAT compounds described herein are small molecules, which can have a molecular weight of about any of 100 to 20,000 Daltons, 500 to 15,000 Daltons, or 1000 to 10,000 Daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the calcineurin/NFAT inhibitor according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

Alternatively, the inhibitors described herein may inhibit the expression of a component of the calcineurin/NFAT pathway. Compounds that inhibit the expression include, for example, morpholino oligonucleotides, small interfering RNA (siRNA or RNAi), antisense nucleic acids, or ribozymes. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

Calcineurin/NFAT inhibitors include antibodies and fragments thereof. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule.

As used herein, the term "antibody" encompasses not only intact (i.e., full-length) polyclonal or monoclonal antibodies, but also antigen-binding fragments thereof (such as Fab, Fab', $F(ab')_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The inhibitors described herein can be identified or characterized using methods known in the art, whereby reduction, amelioration, or neutralization of compound in the calcineurin/NFAT pathway is detected and/or measured. Further, a suitable calcineurin/NFAT inhibitor may be screened from a combinatory compound library using any of the assay methods known in the art and/or using the pericyte or iBBB assays described herein.

One or more of the calcineurin/NFAT inhibitors described herein can be mixed with a pharmaceutically acceptable carrier (excipient), including buffer, to form a pharmaceutical composition for use in reducing calcineurin/NFAT pathway activity. "Acceptable" means that the carrier must be compatible with the active ingredient of the composition (and preferably, capable of stabilizing the active ingredient) and not deleterious to the subject to be treated. As used herein a pharmaceutically acceptable carrier does not include water and is more than a naturally occurring carrier such as water. In some embodiments the pharmaceutically acceptable carrier is a formulated buffer, a nanocarrier, an IV solution etc.

Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. The pharmaceutical compositions to be used in the present methods can comprise pharmaceutically acceptable carriers, excipients, or stabilizers in the form of lyophilized formulations or aqueous solutions. (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (poloxamers) or polyethylene glycol (PEG). Pharmaceutically acceptable excipients are further described herein.

In some examples, the pharmaceutical composition described herein comprises liposomes containing the calcineurin/NFAT inhibitor, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., an calcineurin/NFAT inhibitor) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy $20^{th}$ Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing a calcineurin/NFAT inhibitor with Intralipid™ (a lipid emulsion) or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

To practice the methods disclosed herein, an effective amount of the pharmaceutical composition described above can be administered to a subject (e.g., a human) in need of the treatment via a suitable route (e.g., intravenous administration).

The subject to be treated by the methods described herein can be a human patient having, suspected of having, or at risk for a neurodegenerative disease. Examples of a neurodegenerative disease include, but are not limited to, CAA, MCI (mild cognitive impairment), post-traumatic stress disorder (PTSD), Alzheimer's Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, vascular dementia, progressive supranuclear palsy or cortical basal degeneration.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a neurodegenerative disease (e.g., MCI). A subject having a neurodegenerative disease can be identified by routine medical examination, e.g., clinical exam, medical history, laboratory tests, MRI scans, CT scans, or cognitive assessments. A subject suspected of having a neurodegenerative disease might show one or more symptoms of the disorder, e.g., memory loss, confusion, depression, short-term memory changes, and/or impairments in language, communication, focus and reasoning. A subject at risk for a neurodegenerative disease can be a subject having one or more of the risk factors for that disorder. For example, risk factors associated with neurodegenerative disease include (a) age, (b) family history, (c) genetics, (d) head injury, and (e) heart disease.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a neurodegenerative disease. Alternatively, sustained continuous release formulations of an calcineurin/NFAT inhibitor may be appropriate. Various formulations and devices for achieving sustained release are known in the art.

In one example, dosages for a calcineurin/NFAT inhibitor as described herein may be determined empirically in individuals who have been given one or more administration(s) of calcineurin/NFAT inhibitor. Individuals are given incremental dosages of the inhibitor. To assess efficacy of the inhibitor, an indicator of a neurodegenerative disease (such as cognitive function) can be followed.

Generally, for administration of any of the peptide inhibitors described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a neurodegenerative disease, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen can vary over time.

For the purpose of the present disclosure, the appropriate dosage of a calcineurin/NFAT inhibitor will depend on the specific calcineurin/NFAT inhibitor(s) (or compositions thereof) employed, the type and severity of neurodegenerative disease, whether the inhibitor is administered for preventive or therapeutic purposes, previous therapy, the patient's clinical history and response to the inhibitor, and the discretion of the attending physician. Typically the clinician will administer a calcineurin/NFAT inhibitor until a dosage is reached that achieves the desired result. Administration of a calcineurin/NFAT inhibitor can be continuous or intermittent, depending, for example, upon the recipient's physiological condition, whether the purpose of the administration is therapeutic or prophylactic, and other factors known to skilled practitioners. The administration of a calcineurin/NFAT inhibitor may be essentially continuous over a preselected period of time or may be in a series of spaced dose, e.g., either before, during, or after developing neurodegenerative disease.

As used herein, the term "treating" refers to the application or administration of a composition including one or more active agents to a subject, who has a neurodegenerative disease, a symptom of a neurodegenerative disease, or a predisposition toward a neurodegenerative disease, with the purpose to cure, heal, alleviate, relieve, alter, remedy, ameliorate, improve, or affect the disorder, the symptom of the disease, or the predisposition toward a neurodegenerative disease.

Alleviating a neurodegenerative disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a neurodegenerative disease includes initial onset and/or recurrence.

In some embodiments, the calcineurin/NFAT inhibitor is administered to a subject in need of the treatment at an amount sufficient to enhance synaptic memory function by at least 20% (e.g., 30%, 40%, 50%, 60%, 70%, 80%, 90% or greater). Synaptic function refers to the ability of the synapse of a cell (e.g., a neuron) to pass an electrical or chemical signal to another cell (e.g., a neuron). Synaptic function can be determined by a conventional assay.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Treatment efficacy can be assessed by methods well-known in the art, e.g., monitoring synaptic function or memory loss in a patient subjected to the treatment.

The practice of the present invention will employ, unless otherwise indicated, conventional techniques of molecular biology (including recombinant techniques), microbiology, cell biology, biochemistry and immunology, which are within the skill of the art.

EXAMPLES

In order that the invention described herein may be more fully understood, the following examples are set forth. The examples described in this application are offered to illustrate the methods, compositions, and systems provided herein and are not to be construed in any way as limiting their scope.

Materials and Methods

Cell Lines and Differentiation

All hESC and hiPSC were maintained in feeder-free conditions in mTeSR1 medium (Stem Cell Technologies) on Matrigel coated plates (BD Biosciences). iPSC lines were generated by the Picower Institute for Learning and Memory iPSC Facility. CRISPR/Cas9 genome editing was performed as previously described. All iPSC and hESC lines used in this study are listed in Table 2. ESC/iPSC were passaged at 60-80% confluence using 0.5 mM EDTA solution for 5 minutes and reseeding 1:6 onto matrigel-coated plates.

BEC Differentiation from iPSC

BEC differentiation was adapted from Qian et al., 2017 (Directed differentiation of human pluripotent stem cells to blood-brain barrier endothelial cells. Sci Adv 3, e1701679 (2017)). Human ESC/iPSC's were disassociated to single cell via Accutase and reseeded at $35*10^3/cm^2$ onto matrigel coated plates in mTeSR1 supplemented with 10 μM Y27632 (Stem Cell Technologies). For the next two days, media was replaced with mTesR1 medium daily. On the third day, the medium as changed to DeSR1 medium (DMEM/F12 with Glutamax (Life Technologies) Supplemented with 0.1 mM B-mercaptoethanol, 1×MEM-NEAA, 1× penicillin-streptomycin and 6 μM CHIR99021 (R&D Systems). The following 5 days the medium was changed to DeSR2 (DMEM/F12 with Glutamax (Life Technologies) Supplemented with 0.1 mM B-mercaptoethanol, 1×MEM-NEAA, 1× penicillin-streptomycin and B-27 (Invitrogen)) and changed every day. After 5 days of DeSR2, the medium was changed to hECSR1 Human Endothelial SFM (ThermoFisher) supplemented with B-27, 10 μM retinoic acid and 20 ng/mL bFGF. The BEC's were then split using Accutase and reseeded with hECSR1 supplemented with 10 μM Y27632. The BECs were then maintained through hECSR2 medium (hECSR1 medium lacking RA+bFGF).

Pericyte Differentiation Protocol

Pericytes differentiation was adapted from Patsch et al., 2015 (Patsch, C. et al. Generation of vascular endothelial and smooth muscle cells from humanpluripotent stem cells. Nat. Cell Biol. 17, 994-1003 (2015)) and Kumar et al., 2017 (Kumar, A. et al. Specification and Diversification of Pericytes and Smooth Muscle Cells from Mesenchymoangioblasts. Cell Rep 19, 1902-1916 (2017)). iPSC's were disassociated to single cell via Accutase and reseeded onto Matrigel-coated plates at 40,000 cells/$cm^2$ in mTeSR1 media supplemented with 10 μM Y27632. On day one media was changed to N2B27 media (1:1 DMEM:F12 with Glutamax and Neurobasal Media (Life Technologies) supplemented with B-27, N-2, and penicillin-streptomycin) with 25 ng/ml BMP4 (Thermo Fisher PHC9531) and 8 μM CHIR99021. On day 4 and 5 medium was changed to N2B27 Supplemented with 10 ng/mL PDGF-BB (Pepprotech, 100-14B) and 2 ng/mL Activin A (R&D Systems, 338-AC-010). Pericytes were then maintained in N2B27 media until co-cultured.

NPC Differentiation Protocol

NPCs were differentiated using dual SMAD inhibition and FGF2 supplementation as described in Chambers et al., *Nat. Biotech* 2009 (Chambers, S. M. et al. Combined small-molecule inhibition accelerates developmental timing and converts human pluripotent stem cells into nociceptors. Nat Biotechnol 30, 715-720 (2012)).

Astrocyte Differentiation Protocol

Astrocytes were differentiated as described in T C W, J et al., 2017 (T C W, J. et al. An Efficient Platform for Astrocyte Differentiation from Human Induced Pluripotent Stem Cells. Stem Cell Reports 9, 600-614 (2017)). NPC's were cultured with Neurobasal NPC Medium (DMEM/F12+GlutaMAX, Neurobasal Media, N-2 Supplement, B-27 Supplement, 5 mL GlutaMAX, 10 mL NEAA, 10 mL penicillin-streptomycin) supplemented with bFGF (20 ng/mL). Astrocyte differentiation was induced using astrocyte medium (AM) (Sciencell, 1801). AM was changed every other day and cells passaged at a 1:3 split when 90% confluent.

iBBB Permeability Studies

BECs were enzymatically dissociated by Accutase for 5 minutes following differentiation from iPSC's. BECs were resuspended with hECSR1 supplemented with 10 μM Y27632 onto 24 well Matrigel-coated transwell polyester membrane cell culture inserts (0.4 μm pore size)(Corning, 29442-082) at a density of 500,000-1,000,000 cells/cm$^2$ to achieve a confluent monolayer. 24 hours after seeding pericytes, astrocytes or MEFS were seeded on top of the BECs at a density of 50,000 cells/cm$^2$. Permeability assays were completed when TEER values plateaued with minimum values >1000 Ohms/cm$^2$ for two consecutive days, typically 6 days post-seeding. 4 kDa, 10 kDa, and 70 kDa labeled with fluorescein isothiocyanate (Sigma, 46944, FD10S, 46945), Transferrin (ThermoFisher T-13342), Alexa Fluor 555 Cadaverine (ThermoFisher a30677), BSA (ThermoFisher A34786) were mixed with media and a standard curve was generated. 600 μL Fresh media was added to the bottom of the transwell, 100 μL dye and media were added to the top. Permeability assays were conducted at 37° C. for 1 hour. Media from the bottom of the transwell chamber was collected and analyzed via plate reader. For Efflux transporter Assays, cells were pre-incubated with 10 μM rhodamine 123 (ThermoFisher, R302) and Hoechst dye, 5 μM reversine 121, or 5 μM K0143 (Cayman Chemical 15215) for one hour at 37° C.

3D Cultures

1×10$^6$ BECs/ml, and 2×10$^5$ Astrocytes/ml and 2×10$^5$ pericytes/ml were mixed together and encapsulated in Matrigel supplemented with 10% FBS, 10 ng/ml PDGF-BB, 10 ng/ml VEGF, and 10 ng/ml bFGF. Matigel cell solution was then seeded onto glass bottom culture dish. Matrigel was allowed to solidify for 40 minutes at 37° C. and then grown in complete Astrocyte Media (SciCell) supplemented 10 ng/ml VEGFA. After two weeks VEGFA was withdrawn and iBBBs were subsequently cultured in astrocyte media only. 3D cultures matured for 1 month prior to experimentation and analysis. For imaging experiments, 3D cultures were fixed with 4% PFA overnight at 4° C., washed and blocked for 24 hours each, then incubated with primary and secondary antibodies overnight at 4° C. each followed by a minimum of 48 hours washing.

Amyloid Beta Accumulation

Amyloid accumulation was determined using both neuronal cell conditioned media and 20 nM recombinant labeled Hilyte fluor 488 β-amyloid (1-40) (Anaspec, AS-60491-01) and β-amyloid (1-42) (Anaspec, AS-60479-01) resuspended in PBS. Aβ accumulation for each cell line and experimental permutation was determined from 2D cultures containing all three cells types containing same ratio of cells as 3D experiments. Total area positive for Aβ was divided by the total number of nuclei and normalized to experimental controls. At least four images for each biological replicate were analyzed and for each condition at least three biological replicates were employed. 2D quantifications were corroborated by 3D imaging and analysis.

Immunofluorescence Staining and APOE Immuno-Depletion

Cells were washed with PBS and fixed for 15 minutes with 4% PFA (Electron Microscopy Sciences 15714-S). Samples were then washed with PBS three times for five minutes followed by a permeabilization in PBST for 30 minutes. Cells were blocked in PBST (0.1% Triton X-100) containing 5% Normal Donkey Serum (Millipore S30) and 0.05% sodium azide. Primary antibody staining was done overnight at 4° C. Primary antibodies are listed Table 1. Cells were washed three times for 5 minutes with PBST and incubated an hour at room temperature with their secondary antibody. For immunodepleting experiments, APOE was immunodepleted from pericyte conditioned media by incubating conditioned media with 5 μg of anti-APOE or non-specific IgG control antibodies overnight at 4° C. Antibodies were then removed with magnetic protein A/G beads.

Western Blot and ELISA Lysis Preparation

Cells were washed with PBS and then dissociated using Accutase. Cells were then counted using a hemocytometer with trypan blue and normalized to total cell number. Cells were then washed twice with PBS and lysed with RIPA buffer. Samples were resolved on 4-20% precast polyacrylamide gels (Bio-Rad 4561095). Protein was transferred onto PVDF membranes and blocked with TBST (50 mM Tris, 150 mM NaCl, 0.1% Tween 20) and 5% Milk for one hour at room temperature. Samples were probed overnight at 4° C. on shaking incubator with the indicated primary antibodies. Soluble APOE was quantified from media condition by pericytes for 48 hours using APOE ELISA kit (ThermoFisher, EHAPOE).

RNA Analysis of iPSC-Derived Cell Lines

Total RNA was isolated using Trizol and zymogen RNA-direct spin column treated with DNAse on column of 30 minutes prior to washing and elution. For RT-PCRs, 500 ng of total RNA was reverse transcribed into cDNA with iScript (BioRad). Expression was quantified by SsoFast EvaGreen supermix (BioRad). For RNAsequencing, extracted total RNA was subject to QC using an Advanced Analytical-fragment Analyzer before library preparation using Illumina Neoprep stranded RNA-seq library preparation kit. Libraries were pooled for sequencing using Illumina HiSeq2000 or NextSeq500 platforms at the MIT Biomicro Center. The raw fastq data were aligned to human hg19 assembly using STAR 2.4.0 RNA-seq aligner. Mapped RNA-seq reads covering the edited APOE3/4 site were used to validate data genotypes. Gene raw counts were generated from the mapped data using feature Counts tool. The mapped reads were also processed by Cufflinks2.2 with hg19 reference gene annotation to estimate transcript abundances. Gene differential expression test between APOE3 and APOE4 groups of each cell type was performed using Cuffdiff module with adjusted q-value <0.05 for statistical significance. Geometric method was chosen as the library normalization method for Cuffdiff. Color-coded scatterplots were used to visualize group FPKM values for differentially expressed genes and other genes.

Single-Nucleus RNA-Sequencing and Human Post-Mortem Tissue Staining

Human hippocampal single-nuclei transcriptomic data profiled as part of The Religious Orders Study and Rush Memory and Aging Project (https://www.synapse.org/#!Synapse:syn3219045) was analyzed for computational identification and extraction of pericyte and endothelial single-cell transcriptomes. Putative pericyte and endothelial cells were identified by annotating groups of clustering cells presenting enriched expression of either pericyte or endothelial markers. Identified cells formed disjointed cell groups that did not display enrichment of neuronal, oligodendrocyte, oligodendrocyte progenitors, microglia or astrocyte markers. Cell type annotation was conducted using ACTIONet computational framework (http://compbio.mit.edu/ACTIONet/). A total of 614 putative endothelial and 4,523 putative pericyte cells with detected expression of either APOE, NFATC1, or NFATC2 were detected and considered for analysis. Differential expression for APOE and NFAT genes in APOE4 vs. non-carrier cells was measured using a two-sided Wilcoxon rank sum test, considering cells with detected expression for the genes. snRNA-seq of prefrontal cortex was analyzed further to identify putative pericytes and endothelial cells by extracting a cluster of cells specifically enriched with expression of pericyte markers. Identified cells (n=495 cells). Human Post-mortem tissues were stained with the exception that hippocampal sections which had been imbedded in paraffin and, therefore, xylene deparaffination and re-hydration steps preceded the staining protocol.

In Vivo Administration of Cyclosporine A.

All experiments were performed according to the Guide for the Care and Use of Laboratory Animals and were approved by the National Institute of Health and the Committee on Animal Care at Massachusetts Institute of Technology. 5XFAD mice were obtained from The Jackson Laboratory and APOE4KI were obtained from Taconic. 5XFAD and APOE4KI mice were crossed for at least eight generations. Cylcosporine A was prepared 1 mg/ml in olive oil and injected interperitoneally at a concentration of 10 mg/kg into 6-month-old female mice daily for three weeks. Animals were anaesthetized with gaseous isoflurane and transcardially perfused with ice-cold phosphate-buffered saline (PBS). Brains were dissected out and split sagittally. One hemisphere was frozen, and one was post-fixed in 4% paraformaldehyde at 4° C. overnight. The fixed hemisphere was sliced at a thickness of 40 μM using a Leica vibratome. Slices were blocked for two hours at room temperature and then incubated with primary antibody overnight at 4 C, subsequently washed five times for ten minutes in PBS, and incubated with secondary antibody and Hoechst (1:10000) for two hours at room temperature. Slices were then washed five times for ten minutes in PBS then mounted for imaging. Researchers performing imaging, quantification, and analysis were blind to experimental group of each mouse and unblinded only following analysis.

Isolation of Primary Mouse Brain Pericytes

Primary brain pericytes were isolated from 6 to 8 week old APOE4 knock-in mice. Primary brain pericytes were subsequently expanded for at least two passages and then treated with 2.5 μM cyclosporine A or 5 μM FK506 for two weeks. Gene expression was analyzed by RT-qPCR for human APOE and normalized to mouse GAPDH.

Results

Figure 6A:
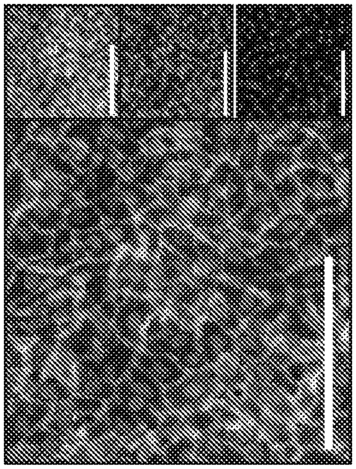
FIGS. 6A-6O. 6A and 6B iPSC-derived brain endothelial cells stained with CD144 (VE-Cadherin), CD31 (PECAM), ZO1 and GLUT1. 6C and 6D, iPSC-derived astrocytes stained with GFAP, S100β and AQP4 6E and 6F Comparative expression analysis of genes in iPSC-derived astrocytes from RNA-sequencing that are reported to be the most differentially upregulated in 6E, fibroblasts and 6F, oligodendrocytes when compared to astrocytes from 6G, 6H, 6I iPSC-derived pericytes stained with CD13, SM22, NG2, and SMA. 6J. Comparative expression analysis of the top differentially upregulated genes in pericytes compared to smooth muscle cells (SMCs). Expression is represented as FPKM values from bulk RNA-sequencing 6K, Comparative expression analysis of the top differentially upregulated genes in SMCs compared to pericytes. Expression is represented as FPKM values from bulk RNA-sequencing 6L, Expression of the top three differentially upregulated genes in pericytes compared to fibroblasts. 6M, Expression of the top three differentially upregulated genes in fibroblasts compared to pericytes. 6N, Expression of pericyte and mesenchymal marker genes in iPSC-derived pericytes. For 6E, 6F, 6J, 6K, 6L, 6M, differential gene lists are based on analysis provided shown as average counts compared to FPKM from bulk RNA-sequencing of iPSC-derived astrocytes and pericytes. 6O, Global hierarchical clustering of transcriptomes (23,588 genes) demonstrates that iPSC-derived pericytes cluster with primary human brain pericytes. Clustering was performed by spearman rank correlation with complete linkage. Mouse brain pericyte transcriptional dataset was obtained from GSE117083. Arterial smooth muscle cell (SMC) dataset from GSE78271.
Figure 6B:
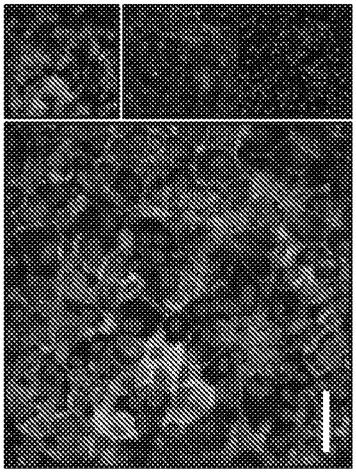
Figure 6C:
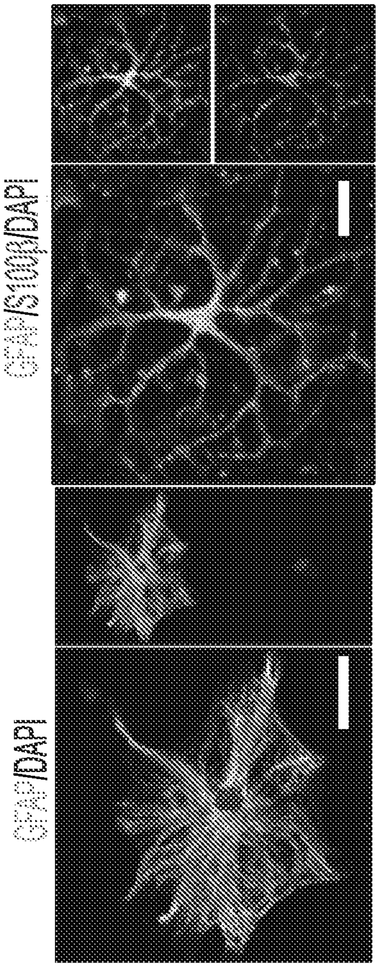
Figure 6D:
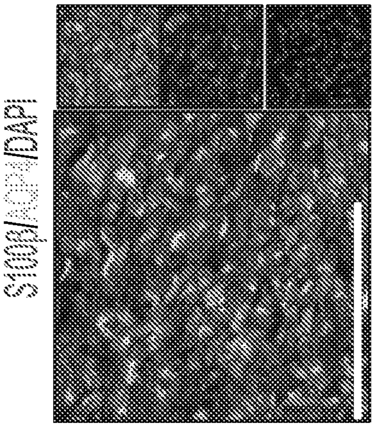
Figure 6E:
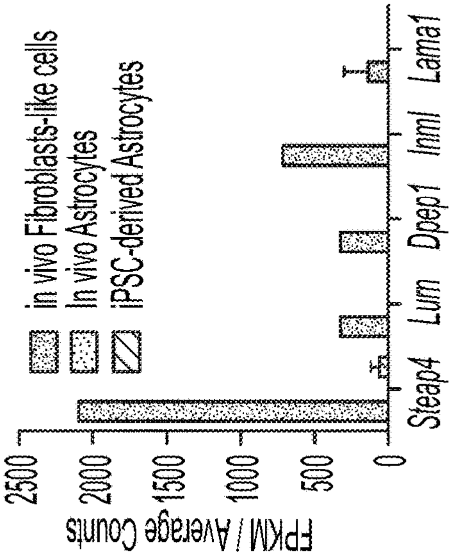
Figure 6F:
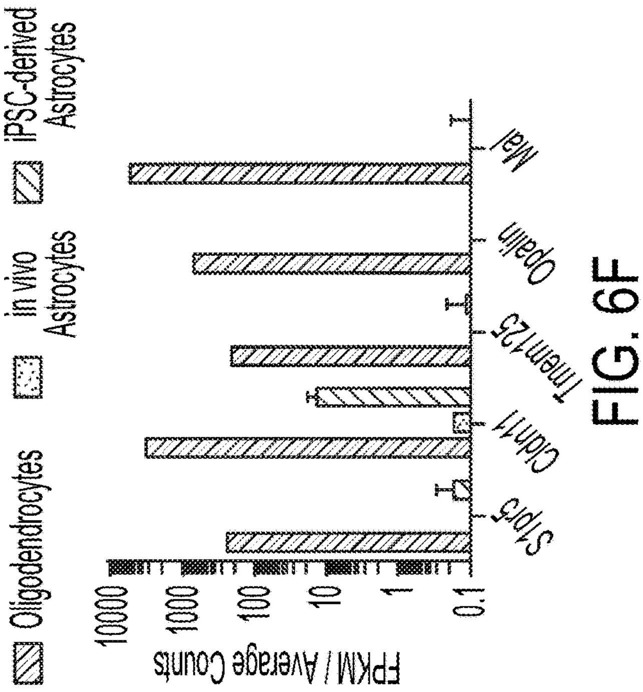
Figure 6G:
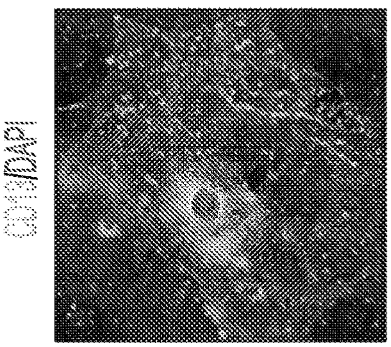
Figure 6H:
Figure 6I:
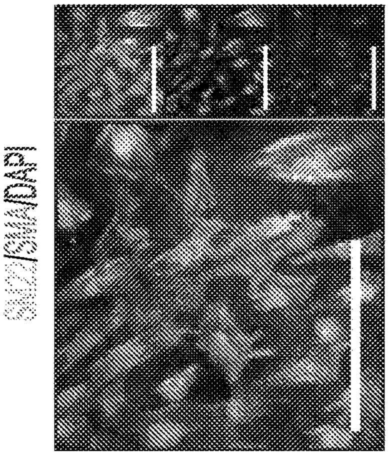
Figure 6J:
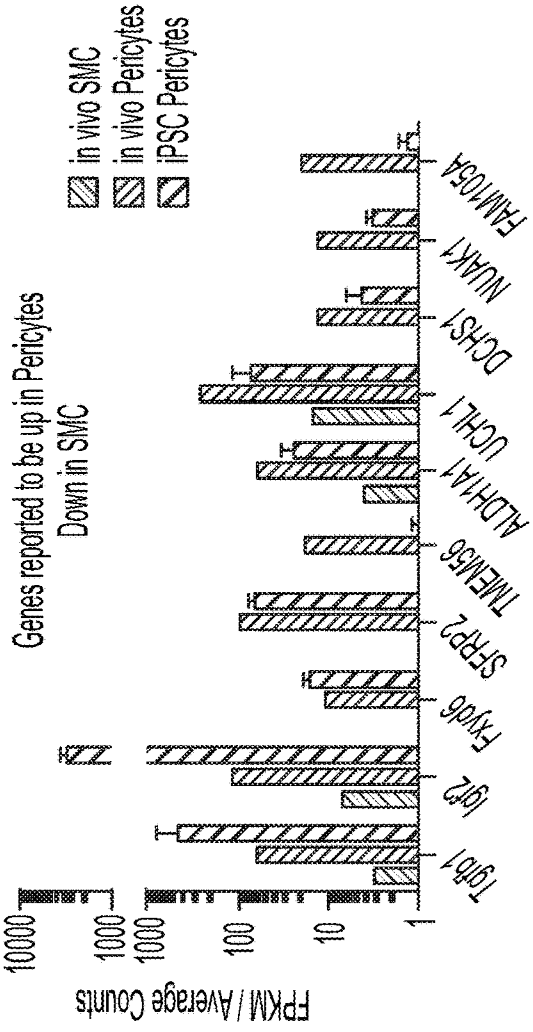
Figure 6K:
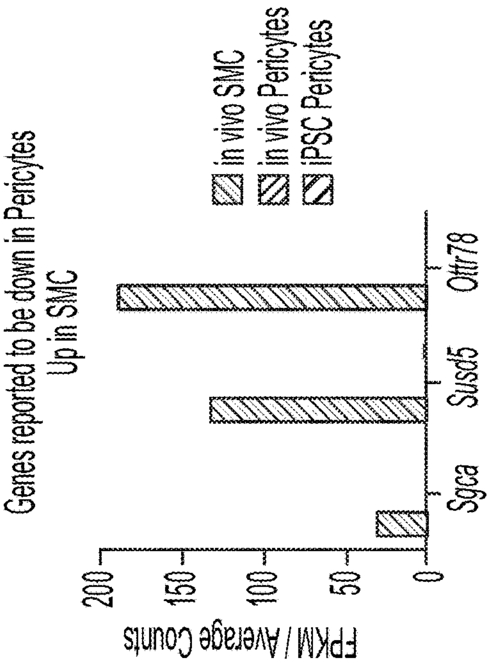
Figure 6L:
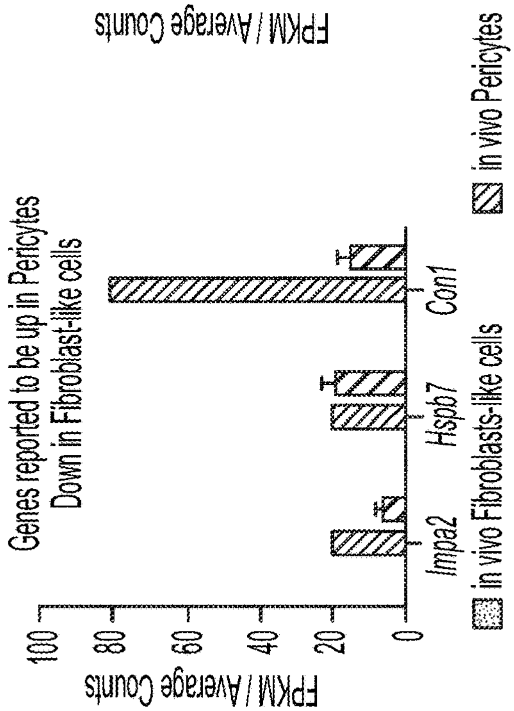
Figure 6M:
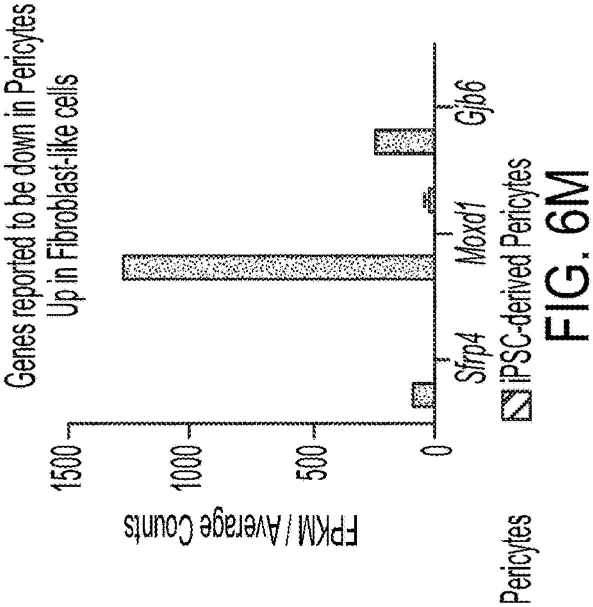
Figure 6O:
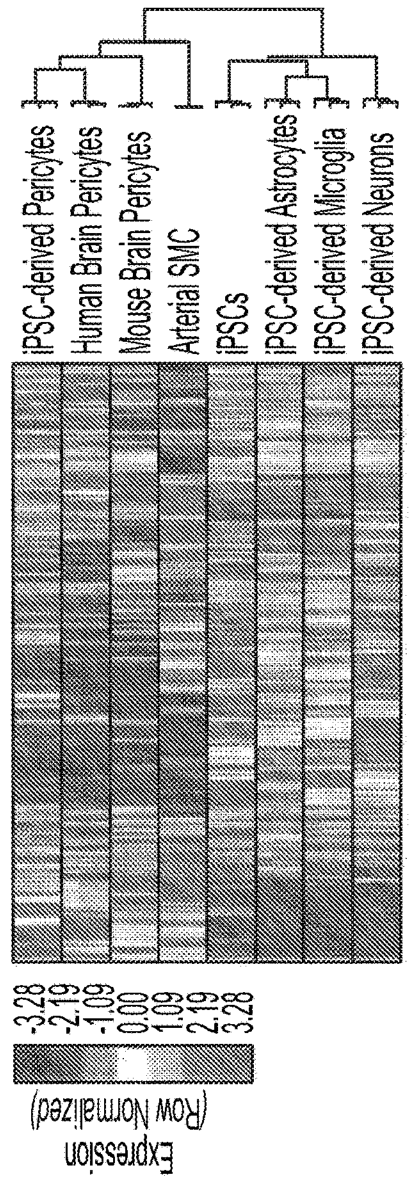
Figure 6N:
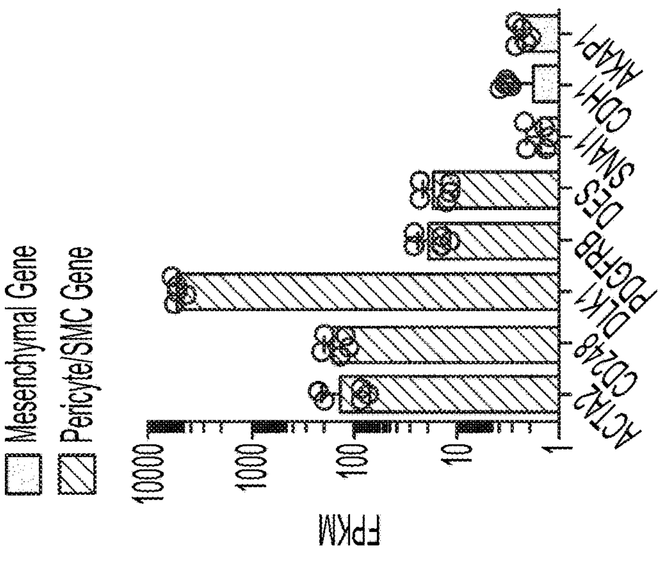

Example 1: Reconstruction of Anatomical and Physiological Properties of the Human Blood-Brain Barrier In Vitro The human BBB is a multicellular tissue formed through the interactions of three cells types: brain endothelial cells (BECs), smooth muscle cells and pericytes, and astrocytes. To reconstruct the BBB in vitro, we first optimized protocols for efficiently differentiating human iPSCs into BECs and astrocytes with morphology and marker expression characteristic of each cell type (FIG. 6*a-d*). Through RNA-sequencing, we validated that iPSC-derived astrocytes express no or low levels of genes that are identified to be differentially upregulated in fibroblasts (Steap4, Lum, Dpep1, Inmt, and Lama1) and oligodendrocytes (S1pr5, Cldn11, Opalin, and Mal) compared to astrocytes (FIGS. 6*e* and *f*). To differentiate iPSCs into pericytes we generated a common mural cell progenitor by exposing iPSCs to Wnt inhibition while simultaneously activating BMP. We then exposed this progenitor to high levels of PDGF-BB while inhibiting TGF-τ3 signaling via Activin A, conditions known to bias differentiation to pericytes over smooth muscle cells (SMC). Similar to pericytes, these iPSC-derived cells expressed CD13, NG2, SMA, and SM22 (FIG. 1*a*; FIG. 6*g-i*). Definitive identification of pericytes is challenging due to the lack of specific markers. Therefore, to more extensively characterize the identity of iPSC-derived pericytes we performed RNA-sequencing of iPSC-derived pericytes and determined the expression of genes that are reported to be differentially up-regulated in pericytes relative to smooth muscle (SMCs). We found that iPSC-derived pericytes robustly expressed TGFBI, IGF2, FXYD6, SFRP2, TMEM56, ALDH1A1, UCHL1, DCHS1, NUAK1, and FAM105A which are among the most differentially upregulated genes in pericytes when compared to SMCs (FIG. 6*j*). In contrast, iPSC-derived pericytes did not express SGCA, SUSD5, and OLFR78 which are among the top significantly upregulated genes in SMCs compared to pericytes (FIG. 6*k*). Likewise, iPSC-derived pericytes did not express genes highly expressed in vascular fibroblasts (SFRP4, MOXD1, and GJB6) but instead highly expressed genes reported to be differentially up-regulated in pericytes (Impa2, Hspb7, and Cnn1) when compared to vascular fibroblasts (FIGS. 6*l* and *m*). Our RNA-sequencing also did not detect the expression of common mesenchymal marker genes (SNA1, CDH1, and AKAP1), in iPSC-derived pericytes but instead robustly detected pericyte and SMC marker genes ACTA2, CD248, DLK1, PDGFRB and DES (FIG. 6*n*). Global hierarchical clustering revealed that human iPSC-derived pericytes are more similar to primary human brain pericytes than arterial SMCs, primary mouse brain pericytes or human iPSC-derived astrocyte, microglia, or neurons (FIG. 6*o*). Collectively, this data demonstrates that these cells express pericyte markers while lacking markers for genes highly upregulated in SMCs, fibroblasts, and mesenchymal cells.

Figure 1B:
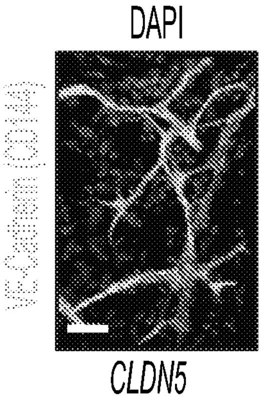
Figure 1C:
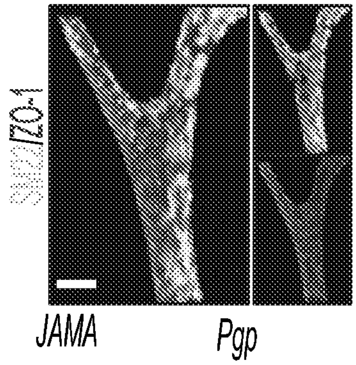
Figure 1D:
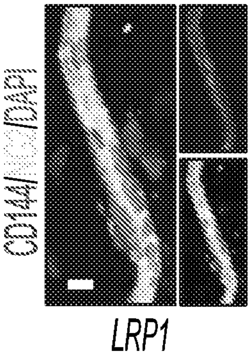
Figure 7A:
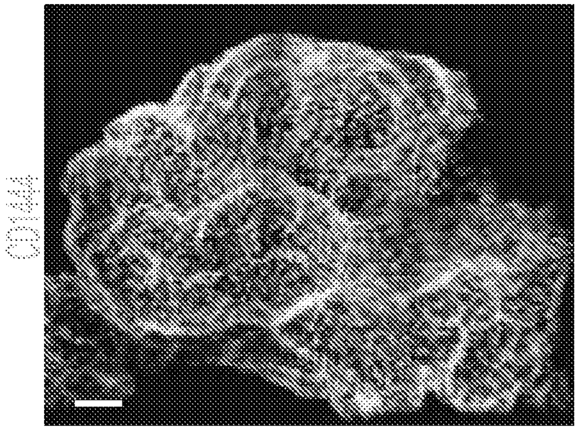
FIGS. 7A-7J. 7A Three-dimensional vascular network of endothelial cells stained with CD144 scale bar=200 μm. 7B, one week after formation pericytes labeled with SM22 are homogeneously dispersed and rudimentary vessels started forming. After two weeks endothelial vessels have formed and pericytes have homed to perivascular space. 7C, Astrocytes are dispersed throughout iBBB cultures. 7D, mRNA expression of AQP4 in each cell type alone, pair-wise and combined. 7E, iBBB without astrocytes do not stain for AQP4. In iBBBs with astrocytes AQP4 densely stains along endothelial vessels. 7F, Immunostaining for LAMA4 showing that Matrigel does not contain LAMA4 however iBBB cultures remodel basement membrane surrounding endothelial vessels to contain LAMA4. 7G, PLVAP mRNA expression is upregulated in BECs from iBBB cultures compared to BECs cultured alone. 7H, PLVAP mRNA expression is downregulated in BECs from iBBB upon removal of VEGFA from culture media. 7I, iBBB cultured in trans-well format express high levels of BBB marker CLDN5 and ZO1. 7J, Polarization of ABCG2 was measured by Hoechst transport for both a BECs monolayer and the iBBB from the apical to the basolateral surface and vice versa. Samples treated with the ABCG2 specific inhibitor KO143 were normalized to each respective non-inhibitor treated sample. Stars represent significance determined by multiple student's t-test (FDR=0.01).
Figure 7B:
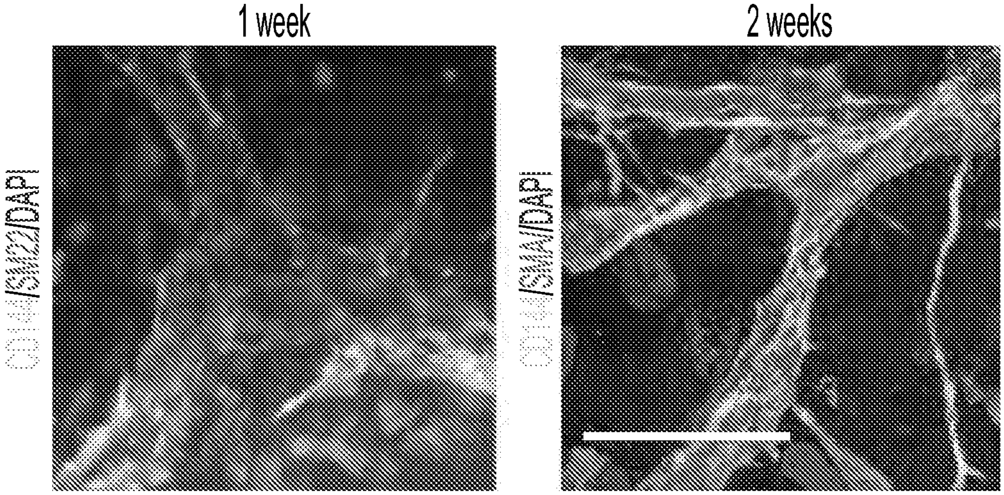

BECs, pericytes, and astrocytes were subsequently encapsulated in Matrigel providing a 3D extracellular matrix. To promote the establishment and survival of each cell type in 3D culture, the Matrigel was initially supplemented with 10% fetal bovine serum and growth factors (10 ng/ml PDGF-BB and 10 ng/ml VEGFA) critical for each of the cell-type. We reasoned that over time these growth factors and positional cues would diffuse, and the cells would become reliant upon paracrine signaling from each other precipitating self-assembly into a tissue. Indeed, after two weeks in the hydrogel matrix, BECs assembled into large (>5 $mm^2$) networks of interconnected CD144-positive cells resembling blood vessels (FIG. 1*b*; FIG. 7*a*). In vivo endothelial cells secrete PDGF-BB recruiting pericytes to the perivascular space surrounding endothelial vessels. Initially, pericytes were evenly dispersed throughout the Matrigel (FIG. 7*b*). However, after two weeks, the pericytes reorganized to occupy positions proximal to the BEC vessels. In the iBBB, we observed SM22-positive and NG2 positive cells lining large and small endothelial vessels potentially reflective of SMC and pericyte coverage of venule to capillary like structures seen in vivo (FIGS. 1*c* and

Figure 1E:
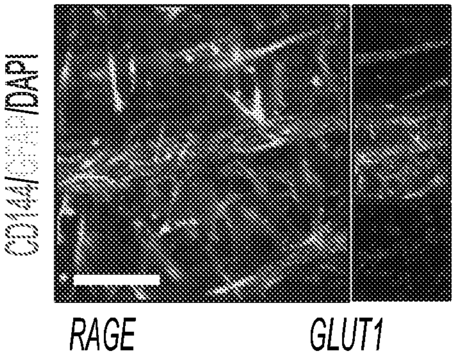
Figure 1F:
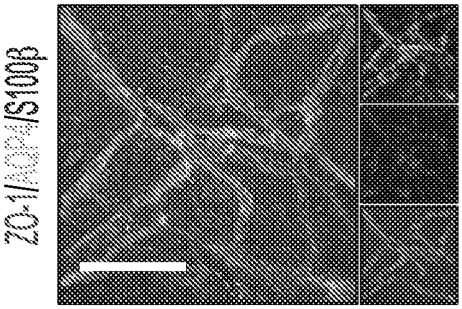
Figure 7C:
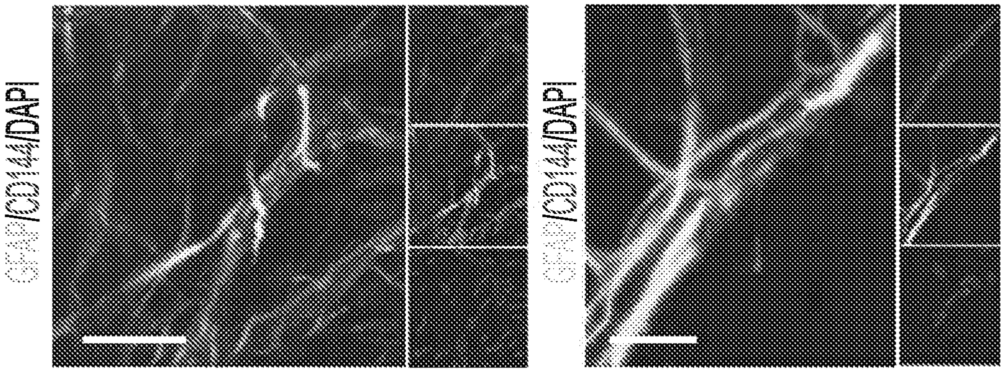
Figure 7D:
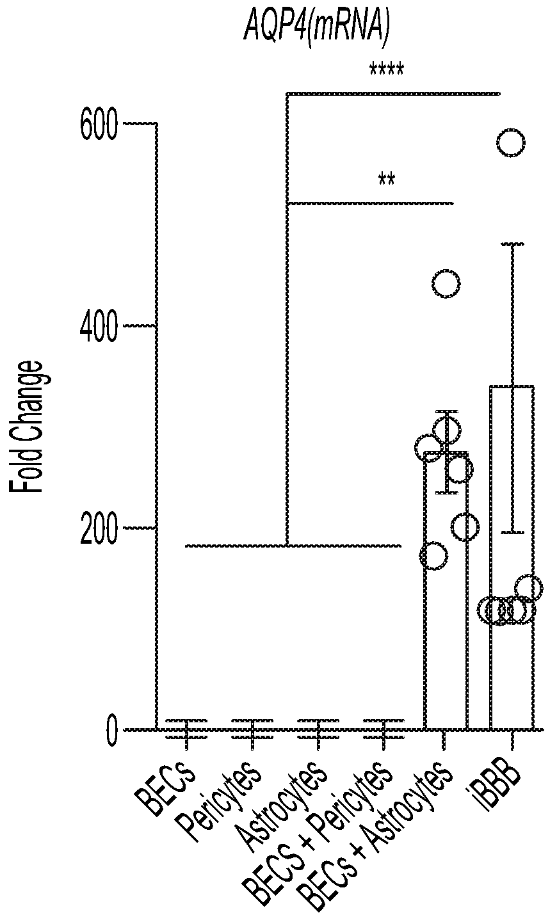
Figure 7E:
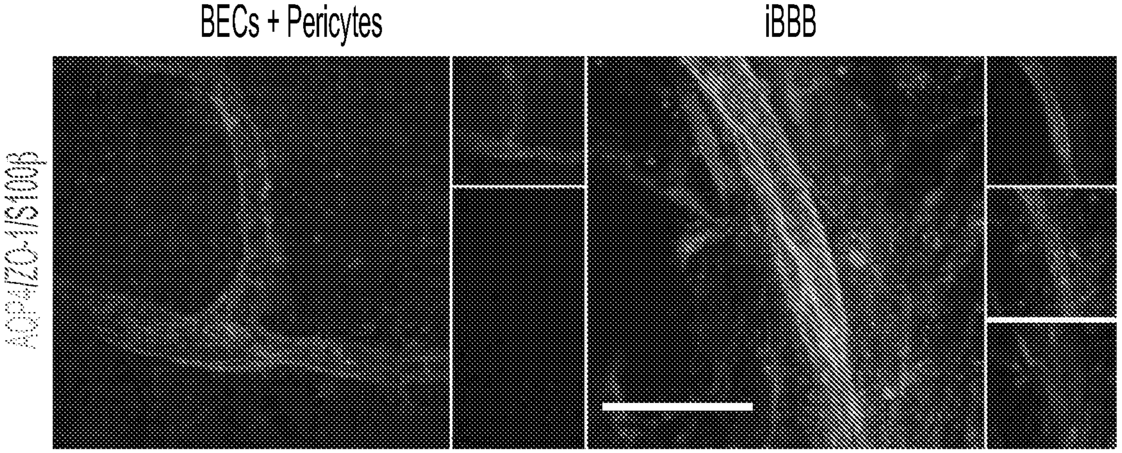
Figure 7F:
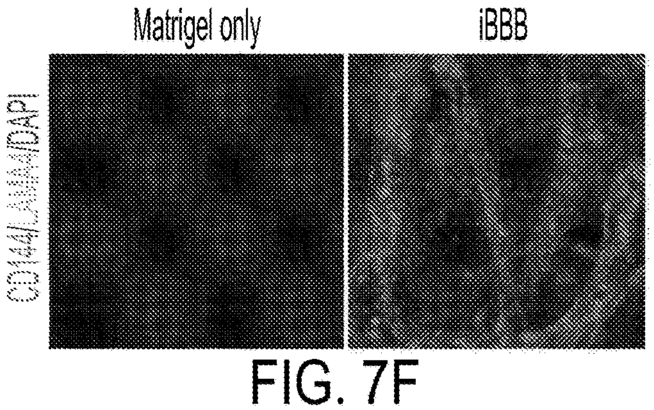

*d*; FIG. 7*b*). In contrast, astrocytes remained more evenly dispersed throughout the 3D culture. However, numerous astrocytes surrounded each endothelial vessel and extend GFAP-positive projections into the perivascular space (FIG. 1*e*, FIG. 7*c*). In vivo astrocytes extend processes known as "end-feet" onto the brain vasculature where they express transport molecules such as aquaporin 4 (AQP4) that regulate the transport of water and other molecules across the BBB. In cultures lacking astrocytes (BECs alone, Pericytes alone, or BECs+pericytes) we did not detect the expression of AQP4 mRNA or protein by qRT-PCR or immunocytochemistry (FIGS. 7*d* and *e*). In contrast, 3D co-cultures that contained all three-cell types, robustly expressed AQP4 mRNA and endothelial vessels were lined with S100β and GFAP-positive astrocytes expressing AQP4 (FIG. 1*f*; FIGS. 7*d* and 7*e*). In the brain, pericytes, astrocytes, and BECs secrete extracellular matrices creating basement membranes that surround the BBB. In vivo BECs secrete laminin α4 (LAMA4), which lines endothelial cells. Through immunostaining we found that LAMA4 is not naturally present in Matrigel (FIG. 7*f*). However, after 1 month in culture we found LAMA4 immunoreactivity surrounding endothelial vessels of the iBBB (FIG. 7*f*). This suggests that iBBB cultures remodel the extracellular matrix to acquire basement membrane proteins found in the in vivo BBB. Collectively, these observations suggest the 3D co-culture of BECs, pericytes, and astrocytes generates vascular structures with anatomical properties consistent with the BBB.

Figure 1G:
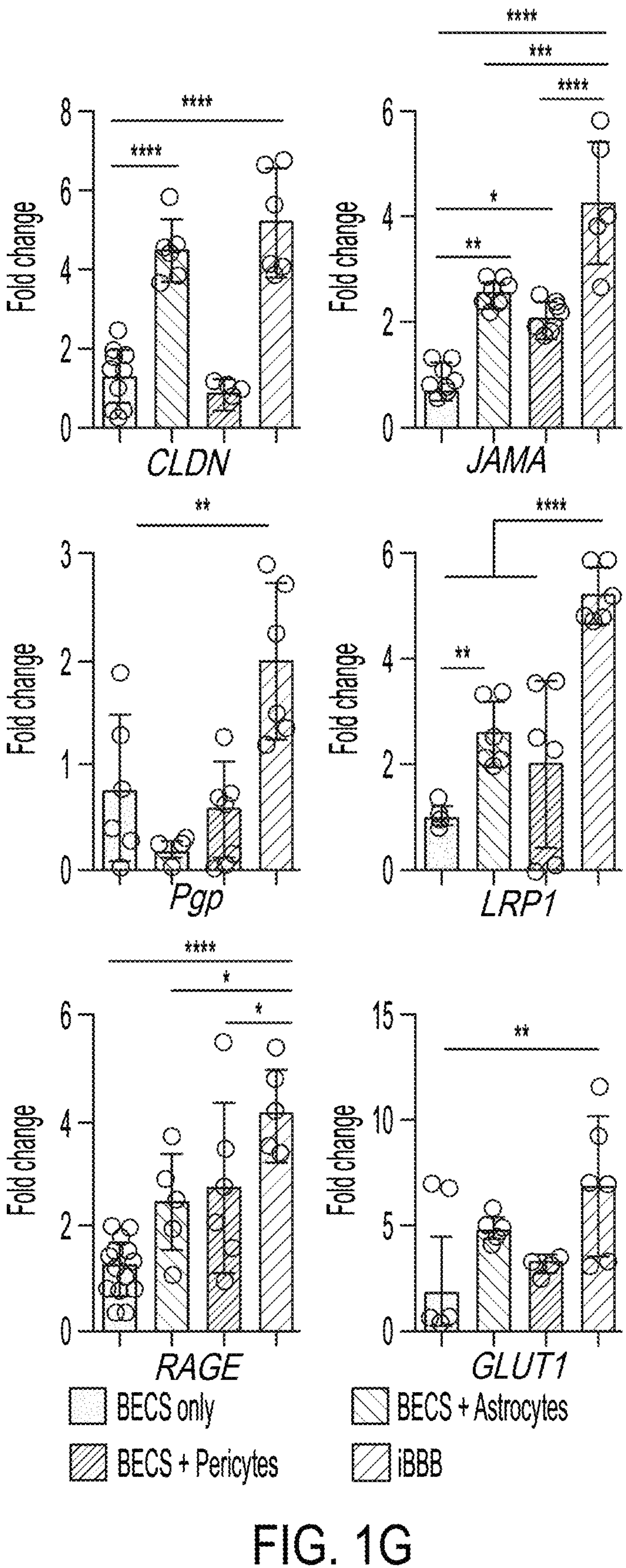
Figure 1H:
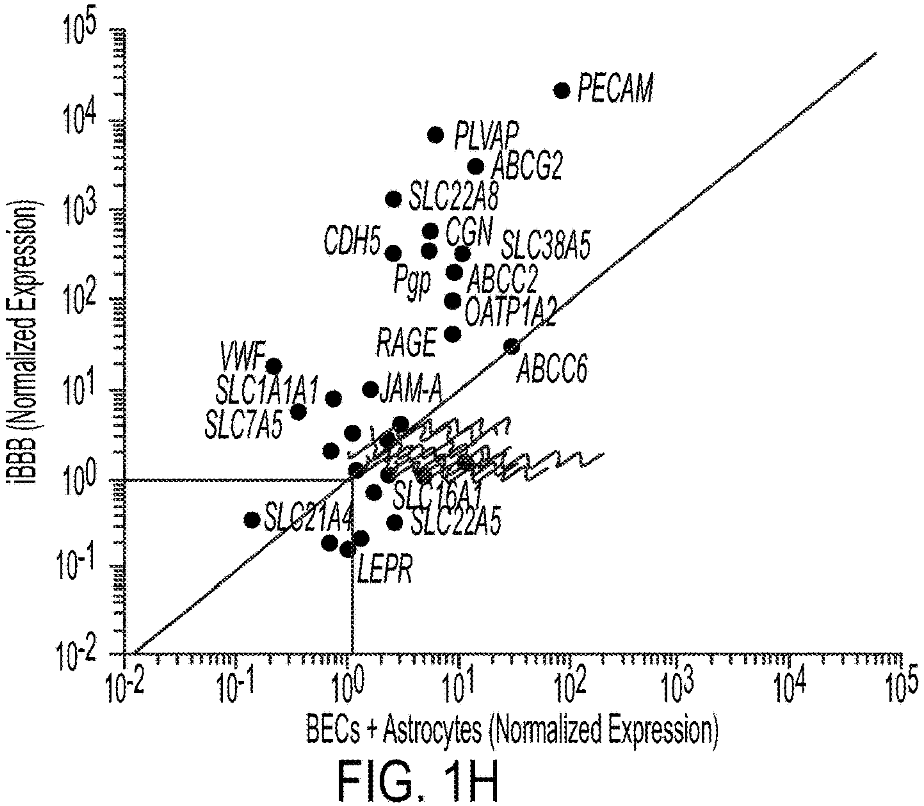
Figure 7G:
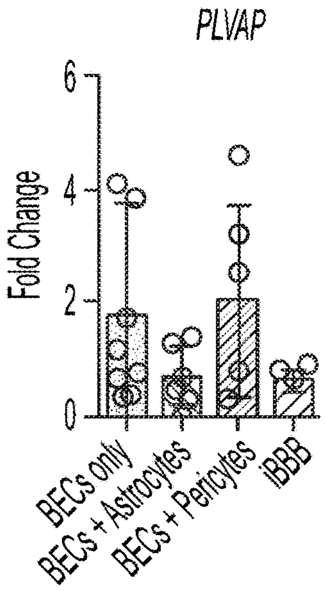
Figure 7H:
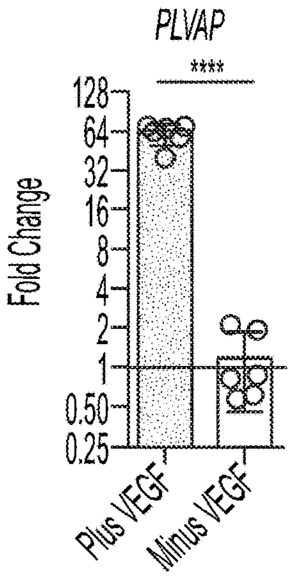

Transplantation studies have demonstrated that the BBB is not an intrinsic function of endothelial cells, but rather is endowed through cooperative interactions with pericytes and astrocytes. In vivo BECs up-regulate tight-junction proteins, cellular adhesion molecules, and solute transporters that generate a specialized barrier restricting paracellular diffusion of fluids, chemicals, and toxins. For example, CLDN5, JAMA, PgP, LRP1, RAGE, and GLUT1 encode tight-junction proteins, transporters, and receptors expressed on BECs and are critical to the function of the BBB that have been used as biomarkers for BBB formation. To examine whether the interaction of BECs with astrocytes and pericytes in our in vitro BBB model resulted in elevated expression of these and other BBB genes, we performed transcriptional profiling by qRT-PCR of BECs cultured alone, with astrocytes or pericytes, and the iBBB that included astrocytes and pericytes. We found that the RNA expression of BBB predictive biomarkers CLDN5, JAMA, PgP, LRP1, RAGE, and GLUT1 were significantly higher in BECs from the iBBB than BECs cultured alone and BECs co-cultured with astrocytes or pericytes except for CLDN5 which was up-regulated to similar levels as the iBBB when astrocytes were co-cultured with BECs (FIG. 1*g*). In addition, numerous other solute transporters, tight-junction components and, cellular adhesion molecules including PECAM, ABCG2, CDH5, CGN, SLC38A5, ABCC2, VWF, and SLC7A5, were selectively up-regulated in the iBBB model compared to BECs alone or co-cultured with astrocytes (FIG. 1*h*). These genes are highly expressed in the BBB and their cooperative action is thought to endow the BBB with its unique barrier properties. We did observe high expression of PLVAP, a marker of angiogenic endothelium known to be induced by VEGFA. We found that the expression of PLVAP was not influenced by the presence of pericytes or astrocytes but was significantly decreased upon removal of VEGFA from culture media (FIGS. 7*g* and *h*). These observations suggest that BECs in the iBBB are able to respond to soluble cues such as VEGFA. To minimize the effects of VEGFA we subsequently cultured the iBBB in VEGFA containing media only for the first two weeks of iBBB formation. Collectively, our results demonstrate that co-culture of iPSC-derived BECs, pericytes, and astrocytes generates a multicellular tissue with fundamental anatomical and molecular properties of the BBB that are observed in vivo.

Figure 1I:
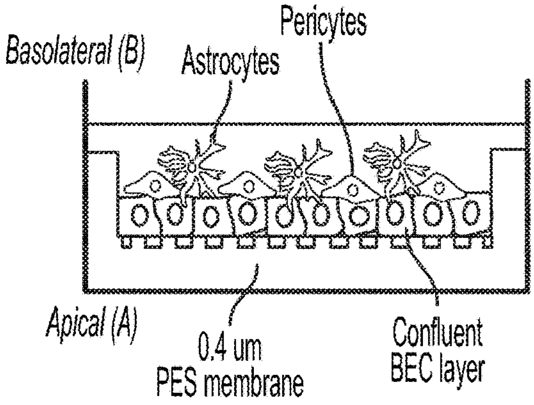
Figure 1J:
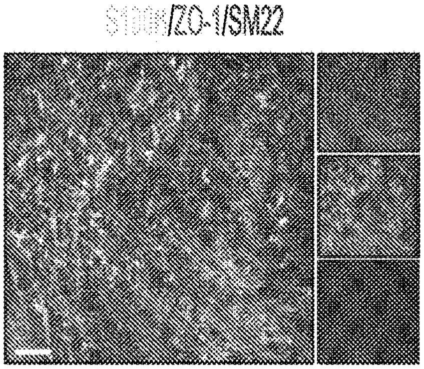
Figure 1K:
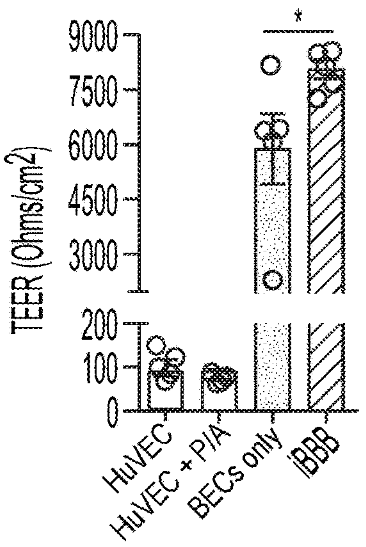
Figure 7I:
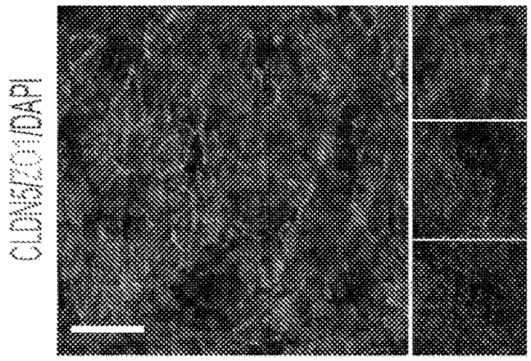

The BBB is a highly selective membrane that restricts the passage of most molecules into the central nervous system. To examine whether the iBBB exhibits increased functional properties of the BBB we established a trans-well system by first generating a confluent monolayer of BECs on a permeable membrane and subsequently layering on top pericytes and then astrocytes (FIGS. 1*i* and *j*). In the trans-well configuration, BECs highly expressed tight junction proteins ZO-1, and CLDN5 that are associated with the BBB (FIG. 7*i*). Trans-endothelial electrical resistance (TEER) is a measurement of electrical resistance across an endothelial monolayer that is used as a sensitive and reliable quantitative indicator of permeability. All immortalized endothelial cell lines that form barriers exhibit TEER values below 150 Ohms/cm. Likewise, peripheral endothelial cells such as human umbilical cord vascular endothelial cells (HuVECs) have relatively high permeability and thus exhibit low TEER. In agreement with these reported observations, we observed TEER values of approximately 100 Ohms/cm$^2$ when we cultured HuVECs in our trans-well configuration (FIG. 1*k*). HuVEC TEER values did not increase by co-culturing with astrocytes or pericytes. As previously reported, iPSC-derived BECs cultured alone had significantly higher TEER values with an average of 5900 Ohms cm$^2$ (FIG. 1*k*). However, the TEER values for BECs cultured alone exhibited a high degree of variability (SD=+/−2150 Ohms). Co-culturing BECs with pericytes and astrocytes reduced TEER variability (SD=+/−513.9 Ohms) and led to a significant increase in the average resistance (8030 Ohms cm$^2$) suggesting the iBBB is less permeable than HuVECs, or BECs cultured alone (FIG. 1*k*).

Figure 1L:
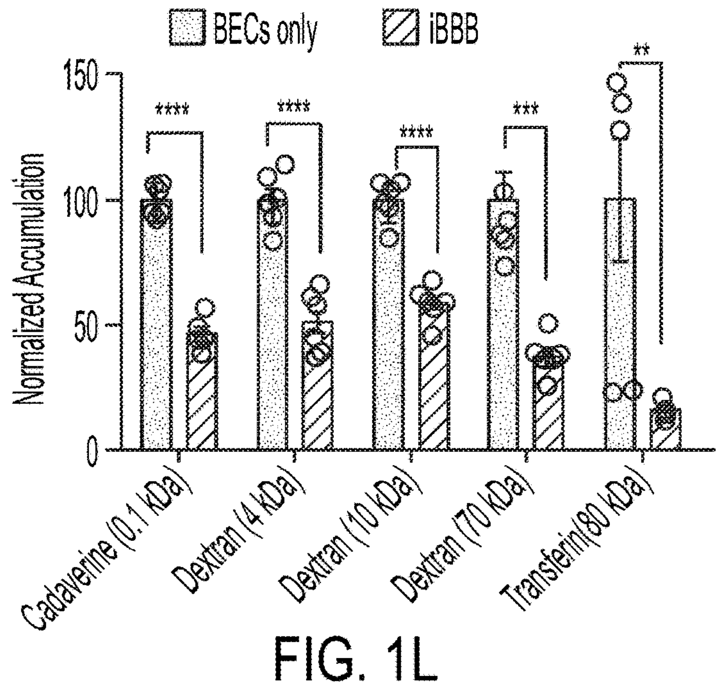
Figure 1M:
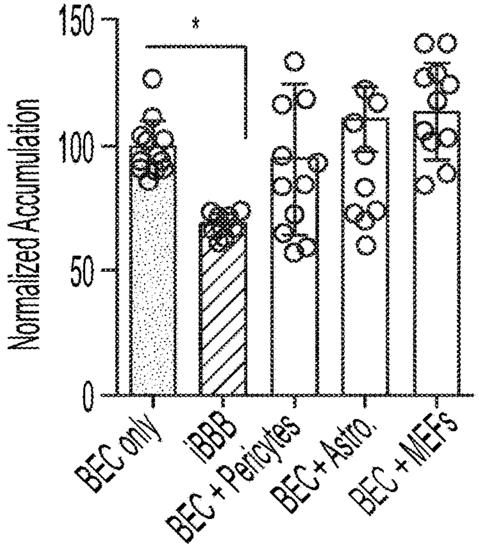
Figure 1N:
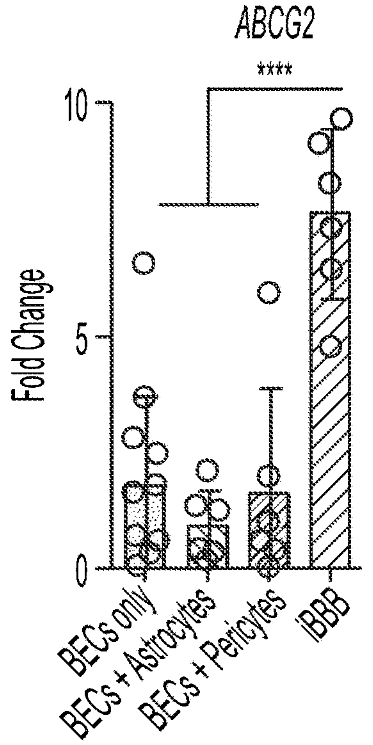

To more fully assess the barrier properties of the iBBB we compared the paracellular permeability of molecules with molecular weights ranging from 0.1 to 80 kDa. For molecules that ranged between 0.1 to 10 kDa, we observed an approximately 50% reduction in paracellular permeability of the iBBB compared to BECs alone (FIG. 1*l*). Molecules with higher molecular weights of 70 and 80 kDa crossed the iBBB far less efficiently compared to BECs alone with 70 and 90% reductions (FIG. 1*l*). To rule out the possibility that the reduced permeability of the iBBB was simply the result of additional layers of cells, we layered on top of BECs double the normal number of pericyte-only, astrocytes-only or a non-relevant cell type, mouse embryonic fibroblasts (MEFs). Neither astrocytes, pericytes nor MEFs cultured alone with BECs led to a reduced permeability whereas the co-culture of astrocytes and pericytes in the iBBB led to a significant reduction in permeability (FIG. 1*m*). This demonstrates that the reduced permeability of the iBBB requires the cooperative presence of both astrocytes and pericytes and, is not just an effect of physically layering additional cells. In conjunction with molecular profiling and TEER values, this establishes that cooperative interaction of astrocytes, pericytes, and brain endothelial cells in the iBBB imparts molecular and functional properties consistent with a physiological BBB.

Figure 1O:
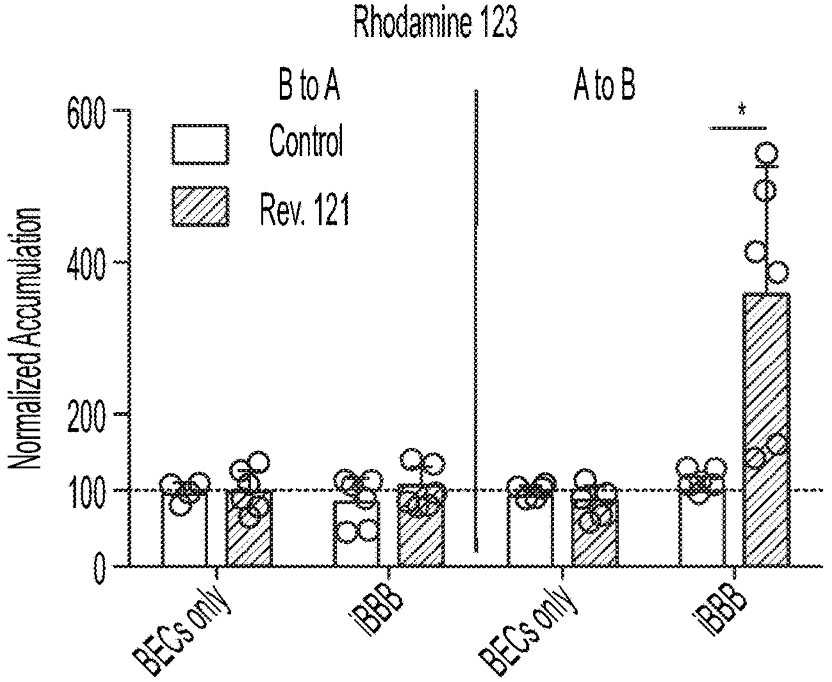
Figure 7J:
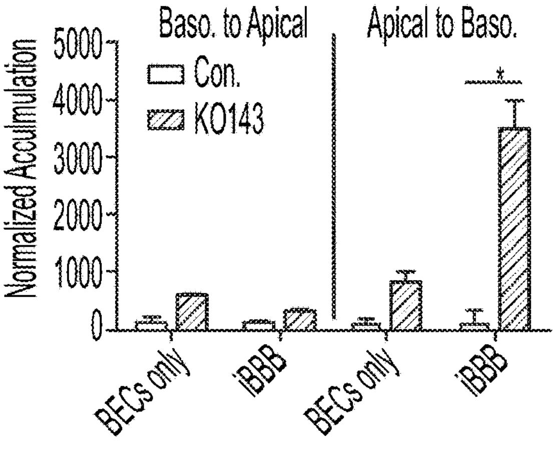

Endothelial cells in the BBB express efflux pumps that are selectively present on the apical surface. Expression and polarization of efflux pumps is an important mechanism by which the BBB prevents small and lipophilic molecules from entering the brain. Molecular profiling identified two common efflux pumps p-glycoprotein (Pgp) and ABCG2 to be up-regulated more than 2-fold and 3-fold respectively in the iBBB compared to BECs alone or BECs co-cultured with astrocytes (FIGS. 1*g* and *n*). To determine whether Pgp is polarized on the apical surface of the iBBB we measured the efflux of rhodamine 123 in the presence and absence of the Pgp-specific inhibitor reversine 121, from the apical surface to the basolateral and vice versa. Inhibition of Pgp dramatically increased the permeability of rhodamine 123 from the apical to basolateral side, but not from the basolateral to apical surface (FIG. 1*o*). This suggests that Pgp is largely localized to the apical membrane of the iBBB (FIG. 1*o*). Consistent with a polarized endothelium, inhibition of ABCG2 with the specific ABCG2 inhibitor K0143 also robustly increased the apical to basolateral transport of Hoechst 33258 an ABCG2 substrate (FIG. 7*j*). Collectively, these results demonstrate that the iBBB has high TEER, reduced molecular permeability, and polarization of efflux pumps, which are all key functional properties of the BBB in vivo. Differences between the in vivo human BBB and iBBB likely remain; however, as we demonstrate below the iBBB can provide disease-relevant insight into human BBB biology which can be leveraged to reduce disease pathology in vivo.

Example 2: APOE4 Increases Aβ Accumulation in the iBBB

Figure 2A:
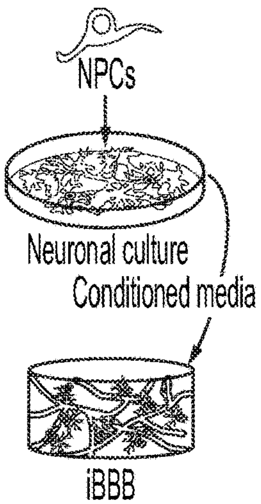
FIGS. 2A-2L. APOE4 increases Aβ accumulation in the iBBB. 2A, Cartoon depicting the experimental paradigm for exposing iBBBs to exogenous amyloid-β 2B, Aβ selectively accumulates on non-AD iBBBs exposed to media conditioned by iPSC-derived neuronal cells from a familial AD patient with an APP-duplication (APP1.1). iBBB derived from APOE3/3 iPSC line (E3/3 parental) from a healthy 75-year-old female. 6e10 antibody recognizes A131-16 epitope. Scale bar, 50 μm. 2C, The APOE3/3 parental iPSC line was genetically edited to an isogenic APOE4/4 allowing the generation of genetically identical iBBBs. Isogenic APOE4/4 iBBBs accumulated more Aβ compared to the parental APOE3/3 iBBB when simultaneously exposed to APP1.1 conditioned media for 96 hours. Scale bar, 50 μm. 2D, Quantification of Aβ accumulation in two isogenic iBBBs with reciprocal genetic editing strategies. Arrows indicate direction of genetic editing where the right-facing arrow indicates editing from APOE3/3 to APOE4/4 and the left-facing arrow indicates editing from APOE4/4 to APOE3/3. Total area positive for Aβ was divided by total nuclei and then normalized to the mean amyloid/nuclei from all E3/3 samples such that the mean of E3/E3 is set to 100%. Automated image analysis was performed with ImageJ. Student t-test (p=0.0114). 2E, APOE3/4 heterozygous iBBBs accumulate significantly more Aβ than APOE3/3 iBBBs. Quantification performed as described in 2D. 2F, Representative images depicting that iBBBs derived from isogenic APOE3/3 and APOE4/4 individuals exhibit high levels of amyloid accumulation assay with anti-amyloid antibody D54D2. 2G, Quantification of amyloid in isogenic iBBBs for Thioflavin T (p=0.0258), and two different amyloid antibodies D54D2 (p=0.0020) and 12F4 (p=0.0054). 2H, Quantification of soluble versus in soluble Aβ 1-40 in remaining in the iBBB culture media 96 hours after inoculation with 20 nM Aβ 1-40 (p=0.0319). 2I Representative three-dimensional IMARIS renderings depicting vascular amyloid accumulation in APOE3/3 and APOE4/4 iBBBs. iBBBs were allowed to mature for 1 month and then simultaneously exposed to neuronal conditioned media from the fAD APP1.1 line. Three-dimensional surfaces of 6e10 and Vecad staining were created using IMARIS software. The total area of 6e10 within 20 μM of the Vecad surfaces was measured. This was normalized to the total area of the Vecad surfaces Scale bar, 10 μm. 2J, Quantification of vascular (<20 μm from BEC vessel) (p=0.0055) and non-vascular (>20 μm from BEC vessel) (p=0.0062) using IMARIS software. Amyloid area was normalized to total vascular area for each image. 2K, Representative image depicting amyloid accumulation in non-vascular cells positive for astrocyte marker S100β Scale bar μm. 2L, Quantification showing the number of astrocytes positive for amyloid for each isogenic genotype. (p=0.0003).
Figure 2B:
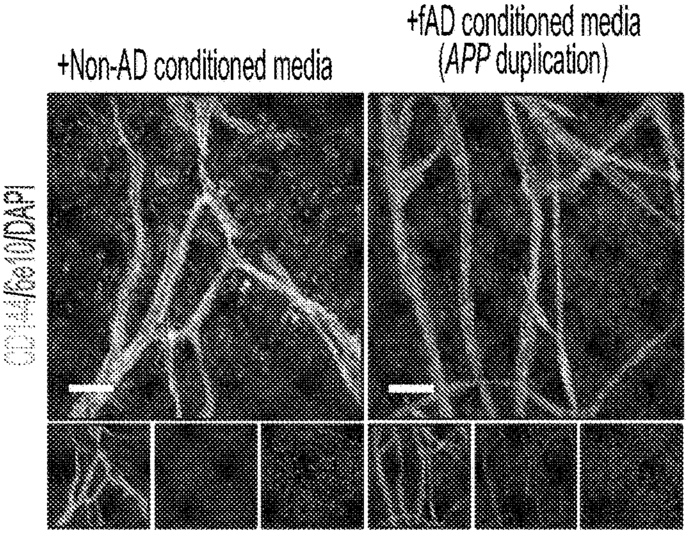
Figure 8A:
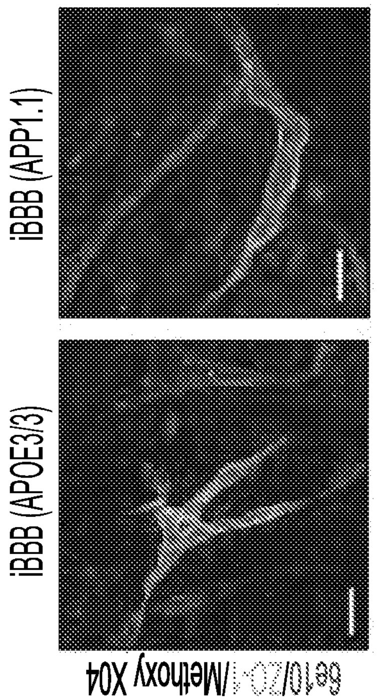
FIGS. 8A-8J. 8A iBBBs generated from a familial AD patient iPSC with duplication of the APP gene (APP1.1) do not inherently have higher amyloid levels than non-AD controls (AG09173). 8B, iBBBs generated from iPSCs with a familial AD-associated mutation (M146I) in the PSEN1 gene do not inherently have higher amyloid levels than its non-AD isogenic control. 8C, Media conditioned by neuronal cells derived from familial AD patient has significantly higher Aβ (1-42). Student t-test ($p=0.0022$). 8D, Representative images depicting that iBBBs derived from APOE3/4 individuals exhibit high levels of Aβ accumulation relative to iBBBs generated from APOE3/3 individuals. 8E and 8F, Representative images depicting that iBBBs derived from isogenic APOE3/3 and APOE4/4 individuals exhibit high levels of amyloid accumulation assay with anti-amyloid antibody Thioflavin T (f) and 12F4 (e). 8G and 8H, Representative images and quantification of Aβ accumulation in isogenic iBBBs exposed to 20 nM Aβ-FITC for 1-40 and 1-42 isoforms. The total area positive for Aβ was divided by total nuclei and then normalized to the mean amyloid/nuclei from all E3/3 samples such that the mean of E3/E3 is set to 100% for each isoform. Students t-test, 1-40 $p=0.0044$; 1-42 $p>0.00001$. 8I and 8J, Normalized amyloid accumulation in isogenic pericyte FIGS. 9A-9C. 9A, Quantification of Aβ accumulation in deconstructed iBBBs. BPA3 and BPA4 indicate all E3/3 and E4/4 iBBBs respectively where B=BECs only, BA=BECs and astrocytes, and BP=BECs and pericytes. Analysis was performed by One-way ANOVA with Bonferroni's post-hoc analysis ($p<0.0001$). 9B, Exposing APOE4/4 astrocytes to APOE4/4 pericyte conditioned media significantly increases amyloid accumulation compared APOE3/3 pericyte conditioned media. Student t test, $p<0.0001$. 9C Quantification and representative image of APOE protein expression in pericytes (NG2-positive cells) and non-pericytes (NG2-negative) cells. Student t test, $p<0.0001$.
Figure 8B:
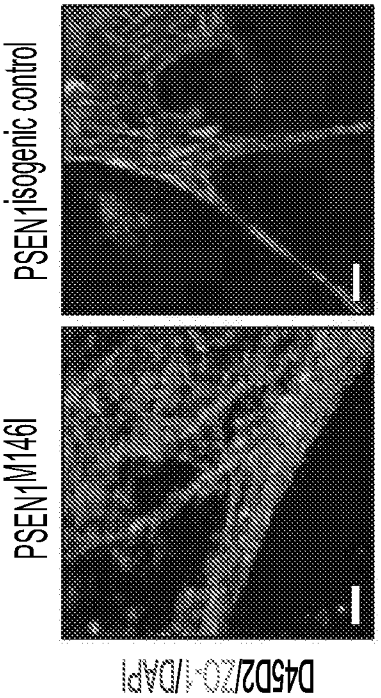
Figure 8C:
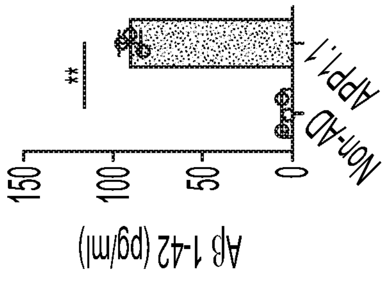

Most (>90%) Alzheimer's disease patients and 20-40% of non-demented elderly people exhibit amyloid deposits along their cerebral vasculature, a condition known as CAA. CAA impairs BBB function, promoting cerebral ischemia, hemorrhages, and accelerating cognitive decline. Thus, we sought to examine amyloid accumulation in our iBBB model, first testing whether iBBBs derived from control or familial AD (fAD) patient lines intrinsically accumulate amyloid. Consistent with low levels of Aβ produced by iBBB cell types, we did not detect appreciable accumulation of amyloid in fAD iBBBs derived from patients with duplication of the APP gene encoding amyloid precursor protein and a separate isogenic pair with a $PSEN1^{M146I}$ mutation and its corrected non-AD control (FIGS. 8*a* and *b*). In contrast, neurons highly express APP and are the most significant source of amyloid in the human brain. Therefore, we next utilized Aβ-rich conditioned media from control and fAD neuronal cultures generated from an iPSC line with duplication of the APP gene. First, we allowed the iBBB to form and mature over 1 month and subsequently exposed it to media conditioned by fAD neuronal cells that we confirmed contained elevated levels of Aβ1-42 by ELISA (FIG. 2*a*; FIG. 8*c*). iBBBs exposed to media conditioned by non-AD neural cells for 96 hours exhibited minimal Aβ accumulation (FIG. 2*b*). In contrast, iBBBs exposed to fAD neural media for 96 hours had significantly more amyloid accumulation, suggesting that the iBBB can model BBB amyloid deposition observed in vivo.

Figure 2C:
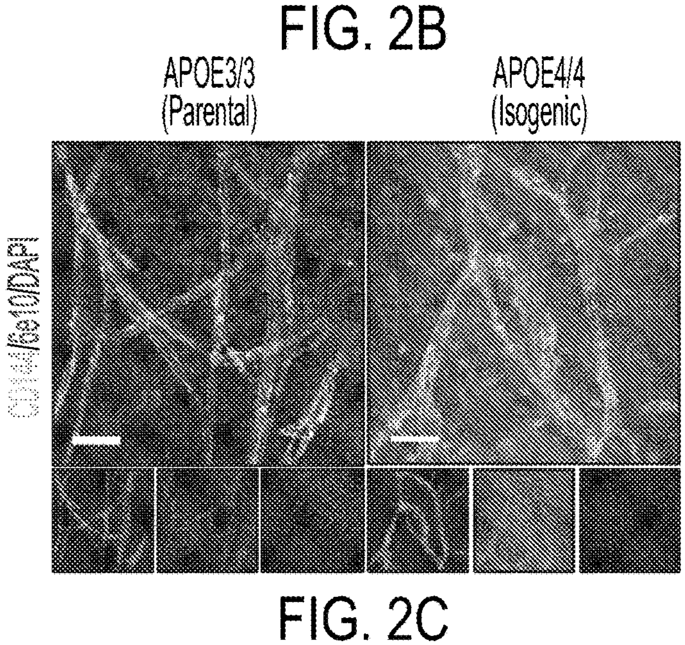
Figure 2D:
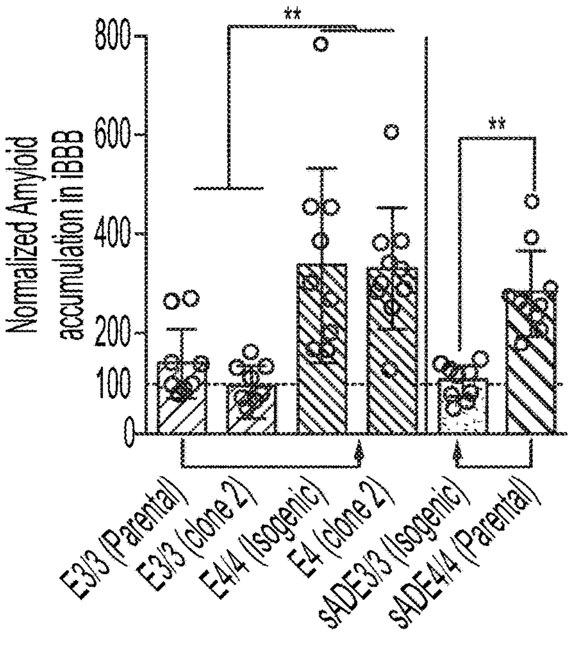
Figure 2E:
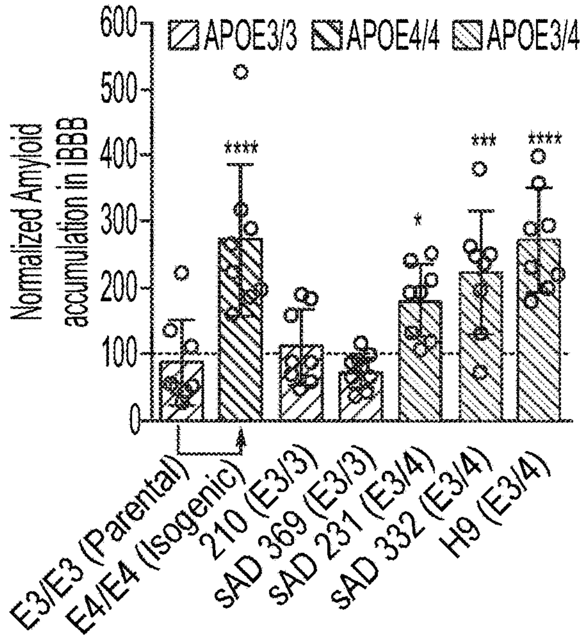
Figure 8D:
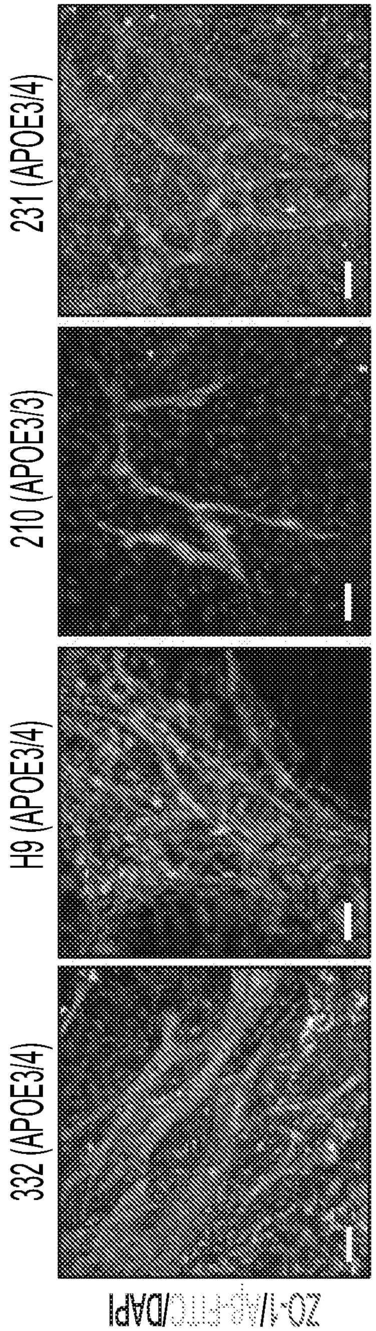

During aging, Aβ levels naturally rise in the human brain. Genetic polymorphisms that influence Aβ deposition and clearance are thought to sporadically precipitate pathologies associated with AD and CAA. In humans, there are three genetic polymorphisms of APOE, 2, 3, and 4. Both clinical and mouse studies have found that APOE4 is the most significant known risk factor for CAA and sporadic AD. However, the underlying mechanism is largely unknown. To examine whether Aβ accumulation is influenced by APOE genotype in the iBBB, we generated iBBBs from isogenic APOE3/3 (E3/3) and APOE4/4 (E4/4) iPSCs, previously reported. When we exposed the iBBB to conditioned media with elevated Aβ isogenic E4/4 iBBBs consistently exhibited significantly more 6e10-positive amyloid accumulation compared to the parental E3/3 iBBBs (FIG. 2*c*). We next examined whether genetically modifying iPSCs from an E4/4 individual to E3/3 could rescue the amyloid phenotype. We again observed that E4/4 iBBB exhibit significantly more 6e10-positive amyloid accumulation in additional clones of the original isogenic pair and a second isogenic pair with the opposite editing strategy (E4/4-risk to E3/3-non-risk), suggesting that increased amyloid deposition in the E4/4 iBBBs is unlikely the result of clonal variation or genetic editing (FIG. 2*d*). APOE3/4 (E3/4) heterozygous humans also have an increased incidence of CAA and AD. Therefore, we next examined whether iBBBs generated from E3/4 heterozygotes exhibit increased amyloid deposition compared to E3/3 iBBBs. Consistent with clinical observations, iBBBs generated from three different E3/4 heterozygous individuals exhibited significantly more amyloid accumulation than iBBBs generated from E3/3 individuals (FIG. 2*e*; FIG. 8*d*).

Figure 2F:
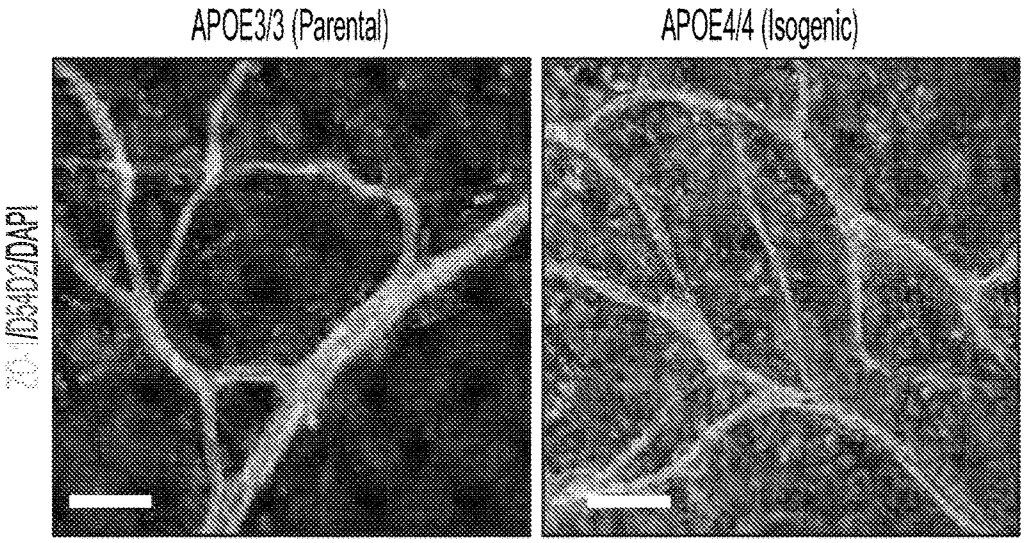
Figure 2G:
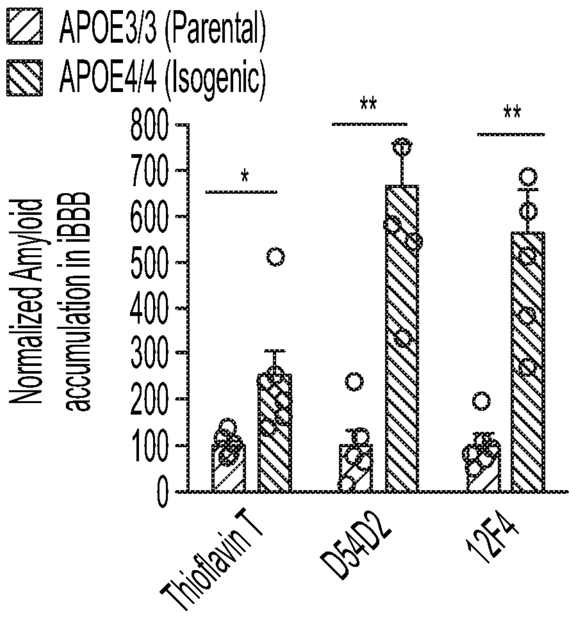
Figure 2H:
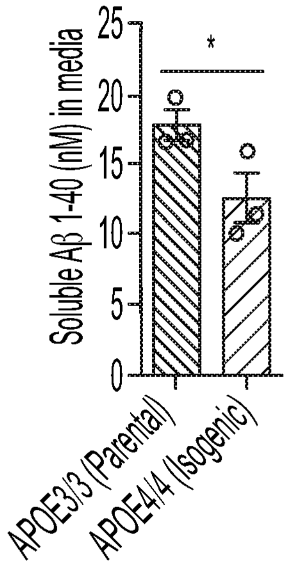
Figure 8E:
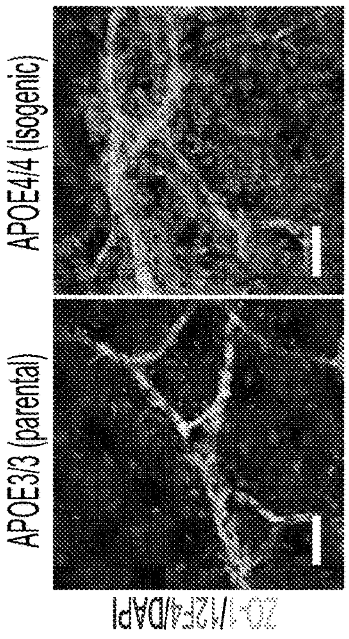
Figure 8F:
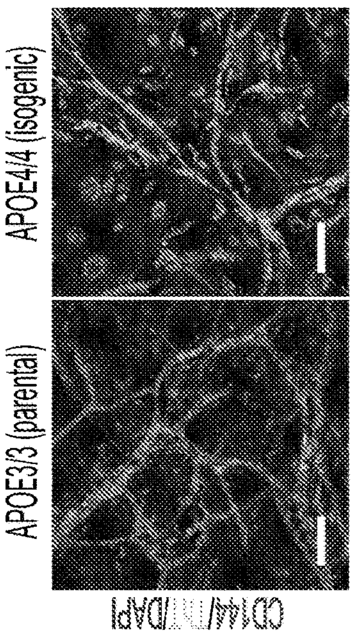
Figure 8G:
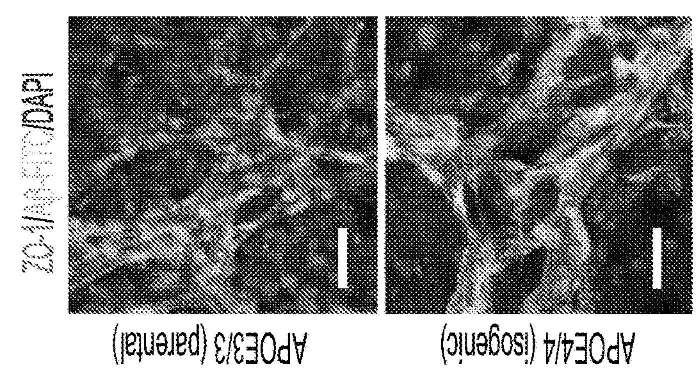
Figure 8H:
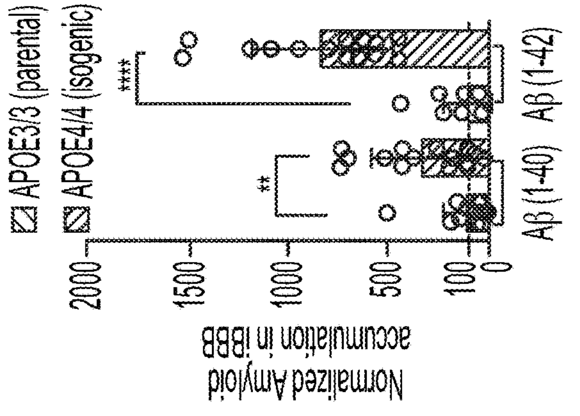

We quantified iBBB Aβ accumulation with four additional methods. First, using two additional antibodies D54D2 (detects several aggregated isoforms of Aβ, such as $Aβ_{1-37}$, $Aβ_{1-38}$, $Aβ_{1-39}$, $Aβ_{1-40}$ and $Aβ_{1-42}$), and 12F4 (detects $Aβ_{1-42}$ oligomers), we further validate that amyloid accumulation is elevated in the APOE4 iBBB compared to the APOE3 iBBB (FIGS. 2*f* and *g* and FIG. 8*e*). We also found that APOE4 iBBBs exposed to fAD conditioned media exhibited significantly higher staining with the chemical dye Thioflavin T (ThT) that binds fibril amyloid (FIG. 8*f*). Furthermore, E4 iBBBs directly exposed to 20 nM fluorescently labeled Aβ peptides (20 nM 1-40/1-42) for 96 hours exhibited higher levels of Aβ accumulation suggesting that the phenotype is intrinsic to E4 iBBBs rather than a secondary response requiring factors in the conditioned media (FIG. 8*g*). We independently tested synthetic Aβ 1-40 and 1-42 isoforms, and found they both exhibited significantly more amyloid in E4 iBBBs when tested alone (FIG. 9*h*). We also found that increased amyloid accumulation in the APOE4 iBBB corresponded with a reduction of soluble monomeric Aβ in the APOE4 iBBB culture media compared to APOE3 iBBBs, further suggesting that APOE4 iBBBs accumulate more amyloid than APOE3 iBBBs (FIG. 2*h*). Collectively, these data demonstrate that similar to clinical studies APOE4 iBBBs accumulate more amyloid compared to isogenic APOE3 iBBBs.

Figure 2I:
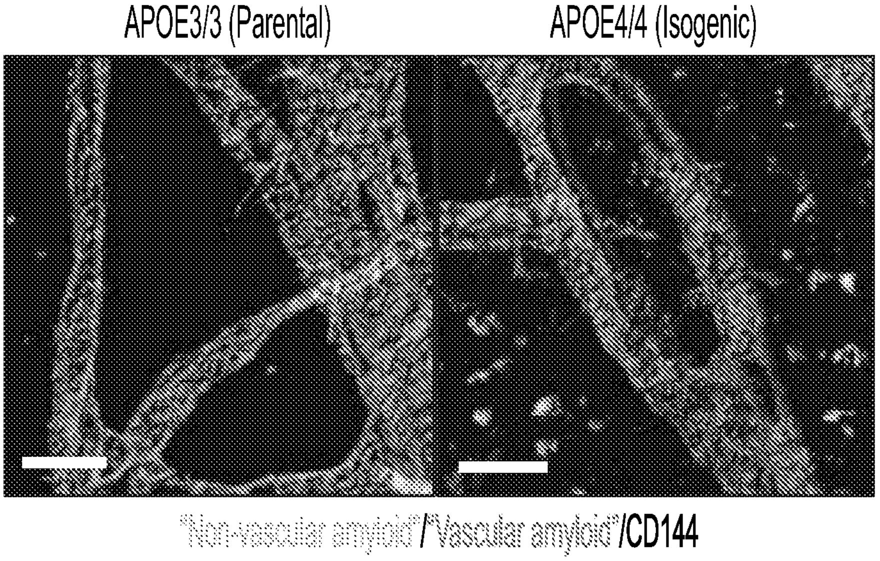
Figure 2J:
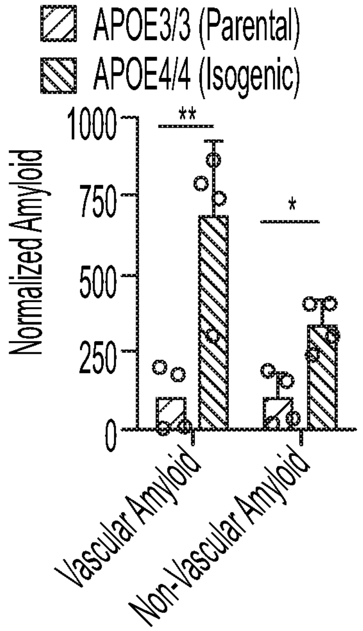
Figure 2K:
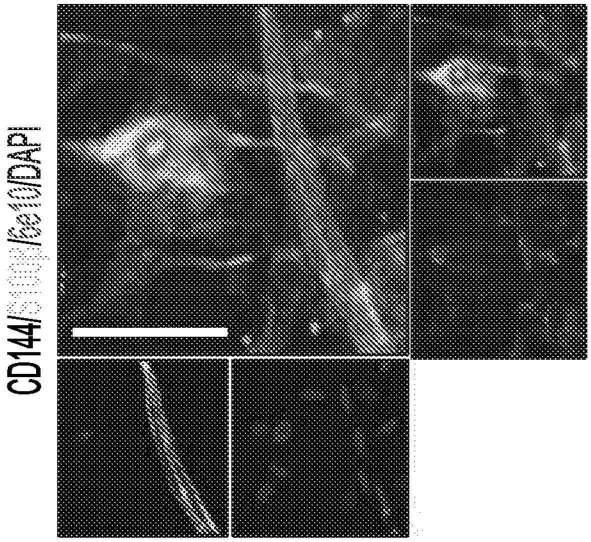
Figure 2L:
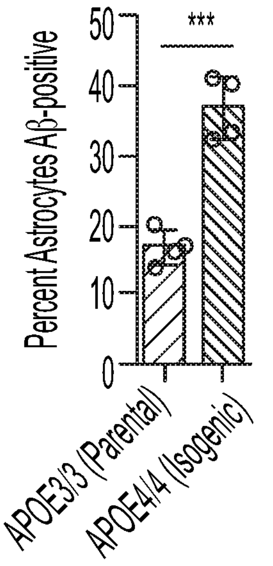
Figure 8I:
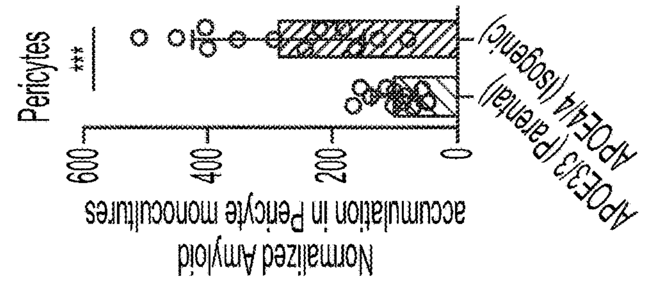
Figure 8J:
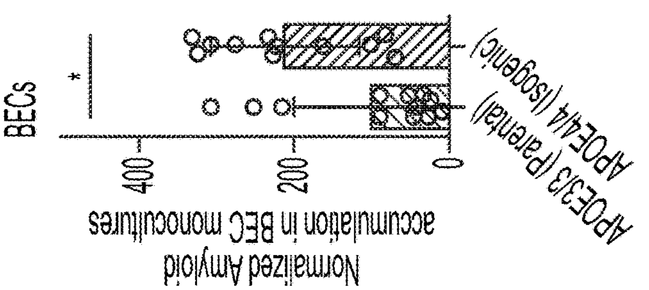

Next, we determined the spatial distribution of the increased amyloid accumulation in the APOE4 iBBB. When cultured alone in 2D, both APOE4 pericytes and BECs accumulated more fluorescently labeled Aβ than their APOE3 counterparts (FIGS. 8*i* and *j*). Using high-resolution IMARIS image analysis, we quantified amyloid via 6e10-positive immunoreactivity that is less than 20 μm from the center of VE-Cadherin-positive vessels, defined as "vascular amyloid", and 6e10-positive immunoreactivity that is greater than 20 μm from the center of a vessel, defined as "non-vascular amyloid" (FIG. 2*i*). In agreement with APOE4 BECs and pericytes accumulating more amyloid in 2D, we found significantly more 6e10-positive amyloid signal on and surrounding BEC vessels of the APOE4 iBBBs compared to APOE3/3 iBBBs (FIGS. 2*i* and *j*). Interestingly, non-vascular amyloid was also increased in the parenchymal space surrounding each vessel in APOE4 iBBB (FIG. 2*j*). This non-vascular amyloid appeared cellular surrounding nuclei positive for astrocytic markers GFAP and S100β (FIG. 2*k*). We found in the APOE4 iBBB approximately 36.8% of astrocytes contained amyloid whereas significantly less (16.8%) of APOE3 astrocytes contained amyloid (FIG. 2*l*). Collectively, these results demonstrate that the iBBB can model aspects of amyloid accumulation observed in CAA and AD and a common genetic predisposition to these pathologies.

Example 3: Pericytes are Required for Increased Aβ Deposition in the iBBB

Figure 3A:
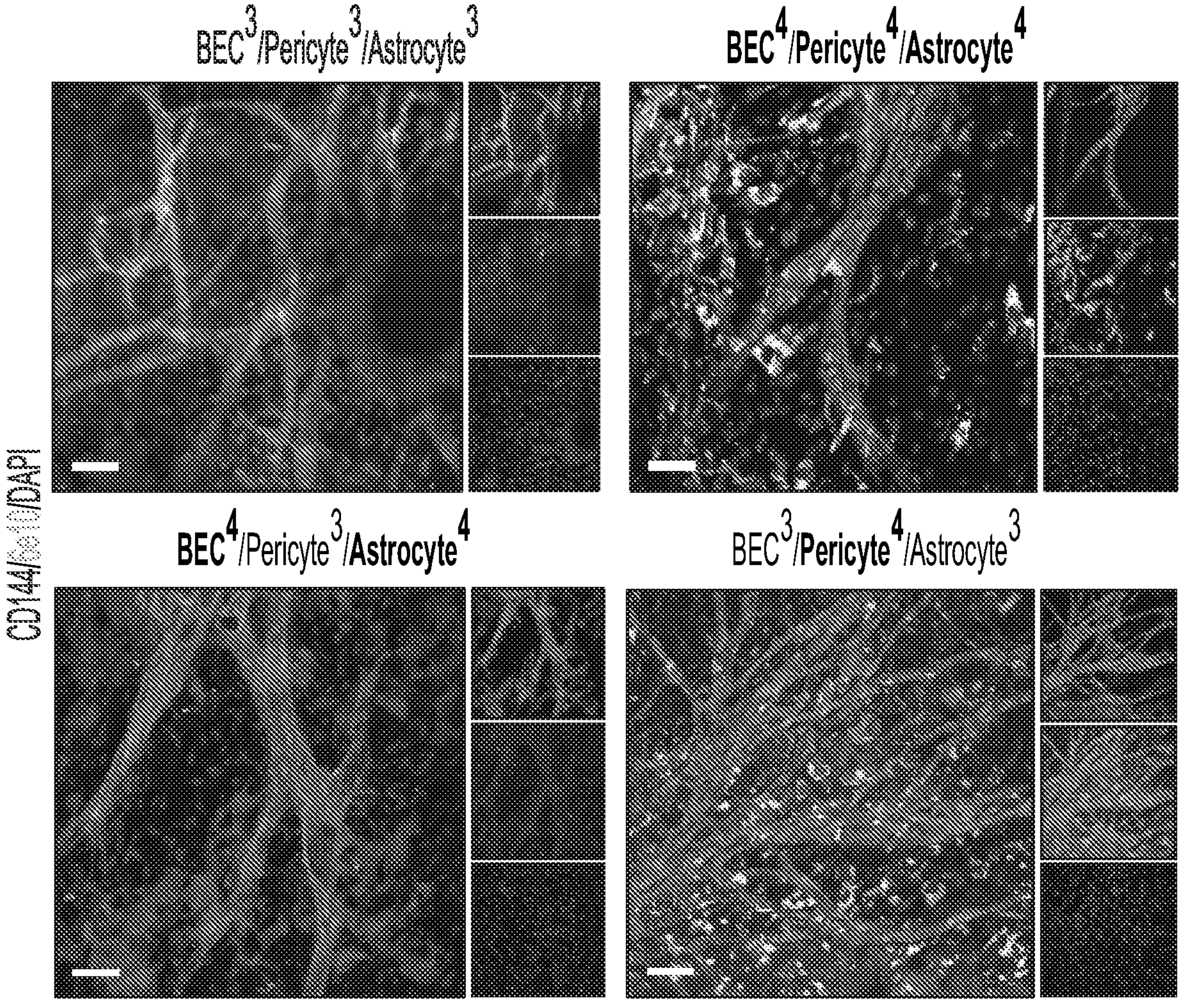
FIGS. 3A-3E. Pericytes are required for increased Aβ deposition in the iBBB. 3A, Representative images depicting combinatorially interchange of E3/3 and E4/4 isogenic cell-types reveals that E4/4 expression in pericytes is required for increased Aβ iBBB accumulation. 3B, Quantification of Aβ accumulation in isogenic iBBBs for each permutation of combinatorial matrix. 3C, Segregating each isogenic permutation based on relative Aβ levels (low or high), reveals that E3/3 and E4/4 BECs and astrocytes are equally represented between the two conditions, however, pericytes are not. For the low Aβ condition only E3/3 pericytes are present. In contrast, for the high Aβ condition, only E4/4 pericytes are present. 3D, Quantification of Aβ accumulation in iBBBs derived from APO3/3 (3), H9 is APOE3/4 heterozygous and 210 is APOE3/3 homozygous. 3E, Quantification of Aβ accumulation in isogenic iBBBs and APOE3/3 iBBBs treated with pericyte conditioned media from either E3/3 (parental) or E4/4 (isogenic) pericytes. Media was conditioned for 48 hours and added iBBBs with 1:1 ratio of fresh media and 20 nM Aβ-FITC for 96 hours.
Figure 3B:
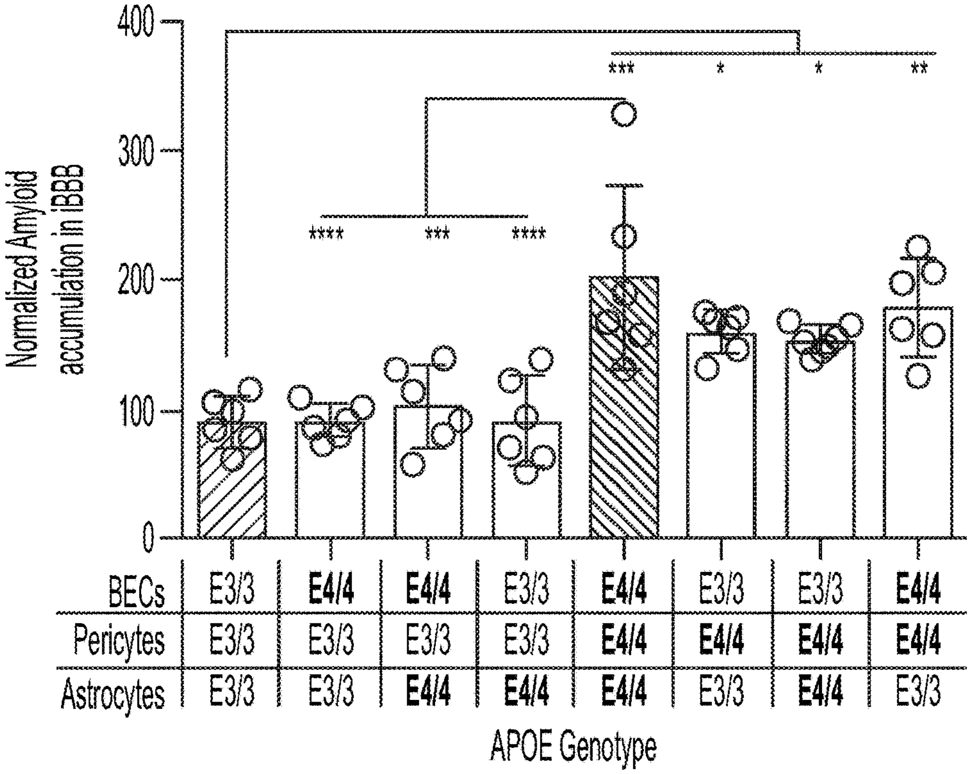
Figure 3C:
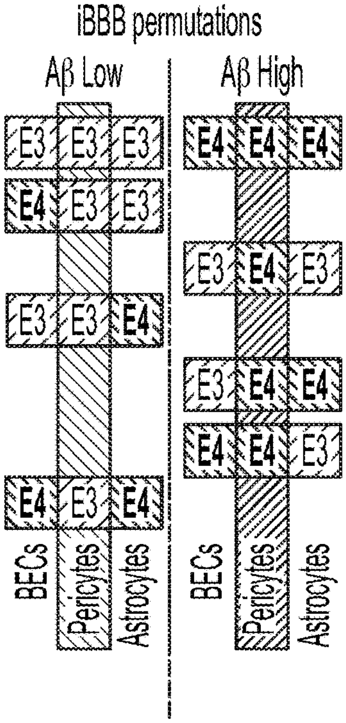
Figure 3D:
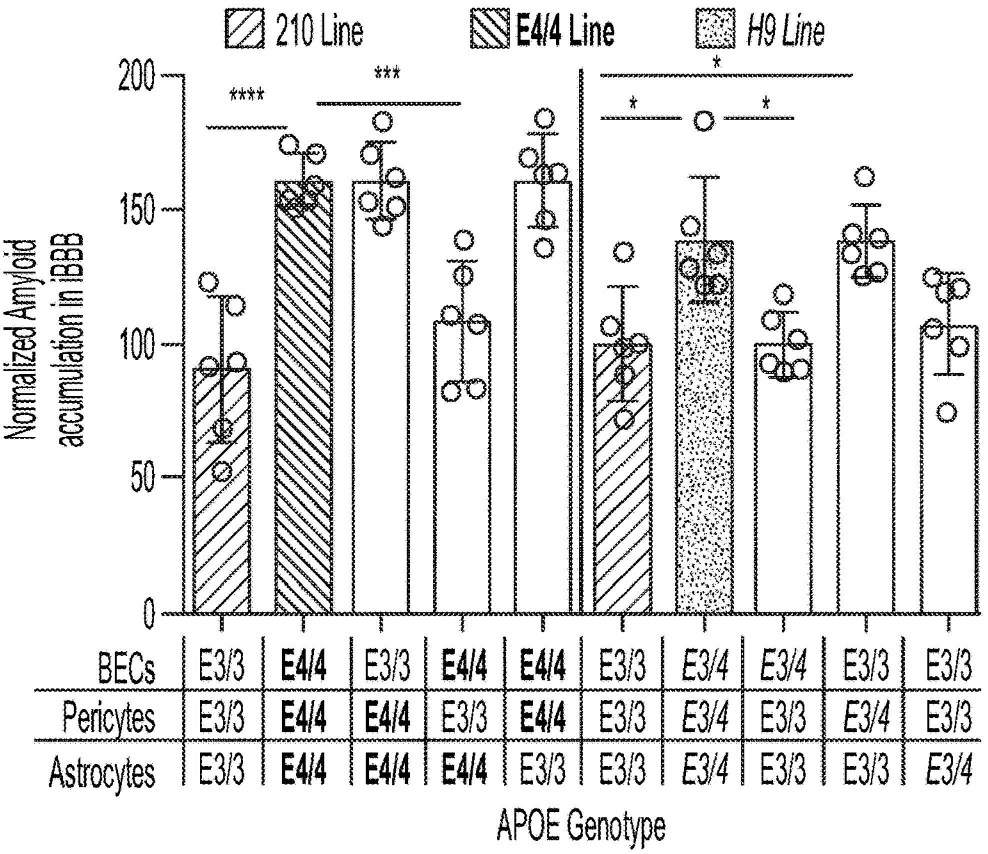
Figure 3E:
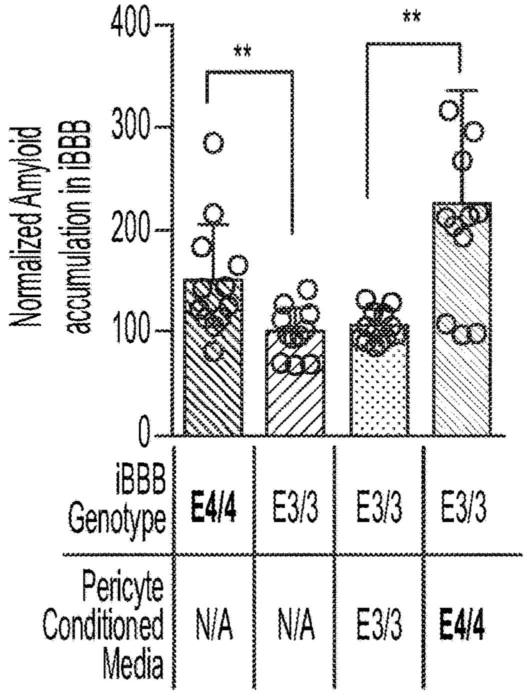
Figure 9A:
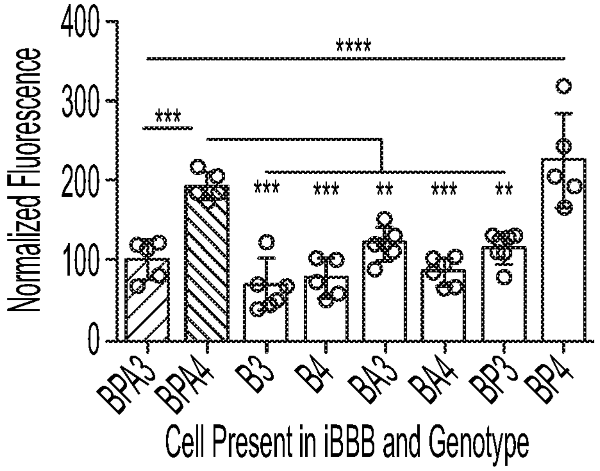
Figure 9B:
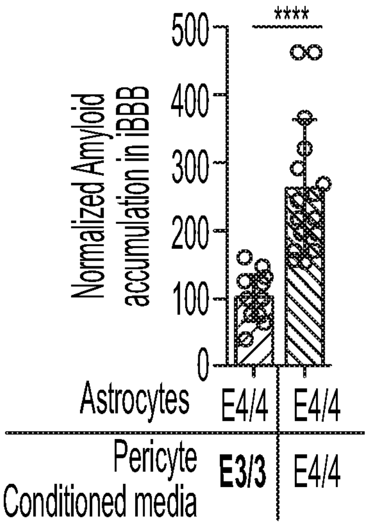
Figure 9C:
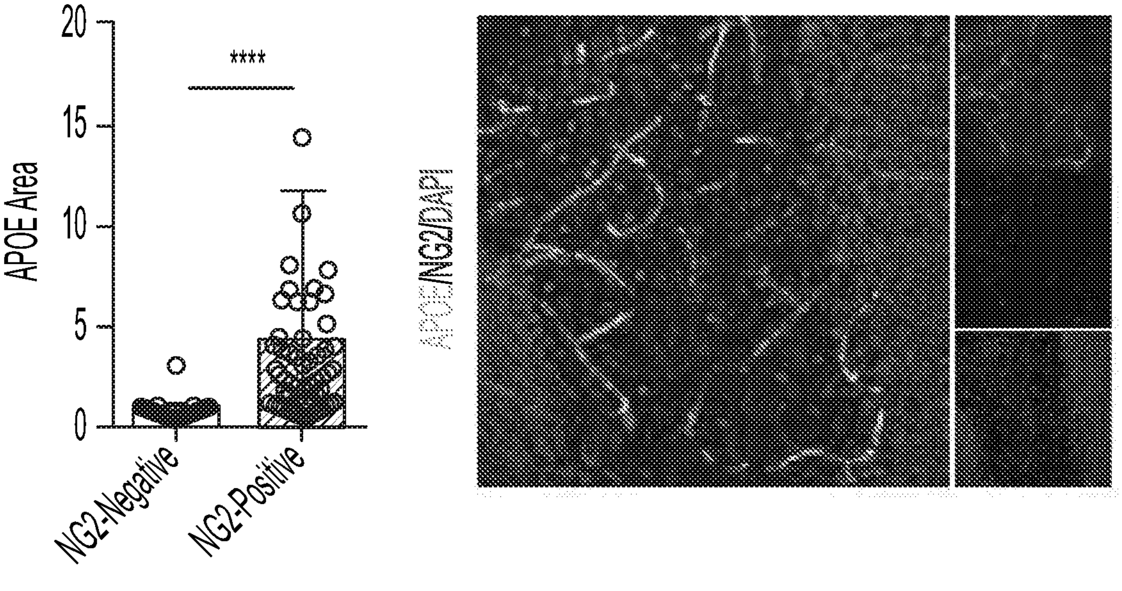

The observed increase in Aβ deposition may require APOE4 expression in all or only some of the cell types present in the BBB. Pinpointing the responsible cells would permit subsequent studies to dissect and target the underlying mechanisms. Therefore, to determine the cellular origins of increased Aβ deposition we performed combinatorial experiments by generating iBBBs from the eight possible permutations of E3/3 and E4/4 from isogenic iPSCs. We first allowed the iBBBs to mature for 1 month then exposed them to 20 nM synthetic FITC-labeled Aβ for 96 hours and quantified the total Aβ-FITC accumulation in each permutation. As previously observed, all E4/4 iBBBs exhibited significantly more amyloid deposition than all E3/3 iBBBs (FIG. 3 *a* and *b*). To analyze the combinatorial effects, we first segregated each of the iBBB permutation based on whether they exhibited low Aβ statistically similar ($p<0.05$) to the all E3/3 iBBB (low Aβ) or the all E4/4 iBBB (high Aβ), and then looked for cellular commonalities between the two conditions (FIG. 3*c*). Both the low and high Aβ conditions equally contained astrocytes and BECs from both E3/3 and E4/4 genotypes (FIG. 3*c*). However, strikingly, all the low Aβ conditions contained only E3/3 pericytes whereas all the iBBBs that exhibited high Aβ accumulation contained only E4/4 pericytes (FIG. 3*b*-*c*). This strongly suggests that E4/4 pericytes are necessary for the increased amyloid phenotype observed in E4 iBBBs. We further confirmed that replacing only E4/4 pericytes with pericytes derived from a different E3/3 individual (210) resulted in a significant reduction in iBBB amyloid deposition regardless of the BEC's or astrocytes' genotype (FIG. 3*d*). To examine whether one copy of E4 in pericytes is sufficient to cause increased amyloid deposition we performed a combinatorial experiment with E3/4 heterozygous BECs, astrocyte and pericytes derived from the H9 human embryonic stem cell line that is APOE3/4 heterozygous (FIG. 3*d*). Again, substituting E3/3 astrocytes or BECs with E3/4 astrocytes or BECs did not significantly increase iBBB amyloid accumulation (FIG. 3*d*). However, as observed with E4/4 homozygous pericytes, replacing E3/3 pericytes with heterozygous E3/4 pericytes increased iBBB amyloid accumulation to a similar level as observed in the all E3/4 iBBB (FIG. 3*d*). This demonstrates that both APOE4 heterozygous and homozygous pericytes alone are sufficient to increase amyloid accumulation in the iBBB (FIG. 3*d*). To further confirm that APOE4 pericytes are sufficient to increase vascular amyloid accumulation, we deconstructed the iBBB into BECs alone, BECs with pericytes, or BECs with astrocytes from each genotype. E4/4 BECs alone or BECs with astrocytes did not recapitulate the observed phenotype. However, E4/4 BECs with pericytes led to a significant increase in amyloid accumulation (FIG. 9*a*). Similarly, we exposed E3/3 iBBBs to media conditioned by either E3/3 or E4/4 pericytes and then added 20 nM Aβ-FITC to all conditions. This revealed that E4/4 pericyte conditioned media is sufficient to increase amyloid accumulation of the E3/3 iBBB (FIG. 3*e*). We also found that treating APOE4 astrocytes with APOE4 pericyte conditioned media significantly increased astrocytic amyloid accumulation (FIG. 9*b*). Together, these results demonstrate that expression of APOE4 in pericytes promotes increased Aβ deposition in the iBBB via an unknown soluble factor. Pericytes and smooth muscle cells express high levels of APOE in the mouse brain (FIG. 9*c*) and pericyte degeneration is accelerated in APOE4 individuals. Recently, pericytes were found to constrict capillaries and induce hypoxia in response to Aβ. How genetic polymorphisms influence pericytes during disease pathogenesis is poorly understood.

Figure 4A:
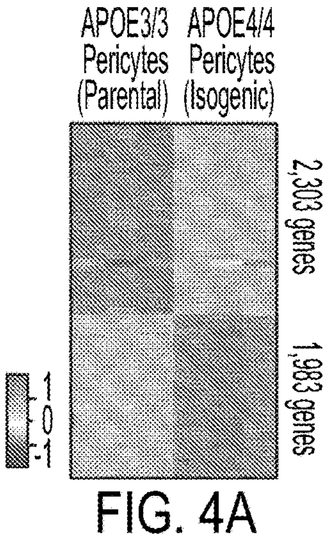
FIGS. 4A-4L. APOE and Calcineurin signaling are up-regulated in APOE4 pericytes. 4A, Heat map depicting differentially expressed genes between isogenic APOE3/3 and APOE4/4 pericytes. (q=0.01) 4B, APOE gene expression is significantly up-regulated in APOE4/4 pericytes whereas it is down-regulated in E4/4 astrocytes. Expression values from qRT-PCR from different RNA than used for RNAseq experiment Astrocyte (p=0.0009), Pericytes (p<0.0001). 4C, Immunofluorescence staining and quantification of APOE in isogenic pericytes. Scale bar, 50 μm. Dots are mean APOE fluorescence intensity from four independent images from a single well. Four wells were measured for each genotype. Unpaired Two-tailed t test (p=0.0005). 4D, Western blot and quantification for APOE protein in APOE isogenic pericyte. Two constitutively expressed proteins in pericytes are included smooth muscle actin (SMA) and GAPDH. (p=0.0033) 4E, qRT-PCR showing APOE gene expression is also up-regulated in an additional isogenic pair that was edited from E4/4 to E3/3 and three APOE3/4 heterozygous pericytes from iPSC lines derived from individuals with sporadic AD and H9 hESC line. Arrows indicated the direction of genetic editing. All values are normalized to the mean expression in all APOE3/3 (n=4) pericytes. Significance determined by One-way ANOVA (p<0.0001) with Bonferroni's multiple comparison test to E3/3 pericytes. 4F, Violin plots depicting APOE expression in pericytes isolated from post-mortem hippocampus of APOE4 carriers. Differential expression was measured using a two-tailed Wilcoxon rank sum test, considering cells with detected expression of APOE. 4G, Representative images and quantification depicting the expression of APOE protein in hippocampal NG2-positive pericytes in post-mortem brains from APOE4-carriers (n=6) and non-carriers (n=6). For each genotype more than 250 NG2-positive pericytes were identified. Unpaired t test, p=0.0068. 4H, Isogenic iBBBs that are deficient for APOE by genetically knocking-out (KO) display similar amyloid accumulation to E3/3 iBBBs. Significance displayed as One-way ANOVA (p<0.0001) with Bonferroni's multiple comparison test 4I Immunodepleting APOE from APOE4 pericyte conditioned media significantly reduces amyloid accumulation in the APOE3 iBBB. One-way ANOVA (p<0.0001) with Bonferroni's multiple comparison test. 4J, Transcription factors differentially expressed between APOE3/3 and E4/4 isogenic pairs (q<0.05). The five transcription factors highlighted are reported to bind APOE gene regulatory elements. 4K, APOE isogenic pericytes stained for NFATc1 and SM22. NFATc1 is present in both cytoplasm and nucleus. Dephosphorylation of NFAT by calcineurin leads to NFAT translocation to the nucleus. Quantification of NFATc1 staining per nuclei for each APOE3/3 and APOE4/4. 150 cells were analyzed for each genotype. Significance determined by students t-test, (p<0.0001). 4L, Nfatc1 expression in brain pericytes of APOE3 and APOE4 knock-in mice. Unpaired two-tailed t test (p=0.0041). was measured using a two-tailed Wilcoxon rank sum test, considering cells with detected expression of APOE.
Figure 4B:
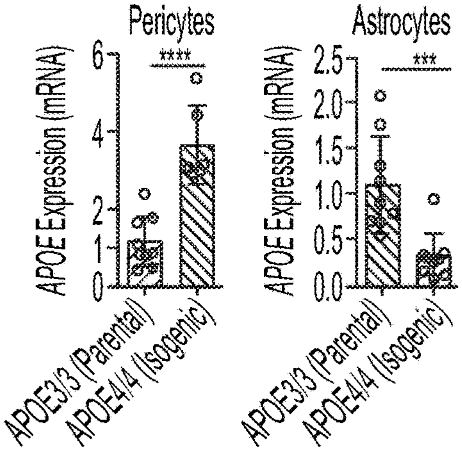
Figure 4C:
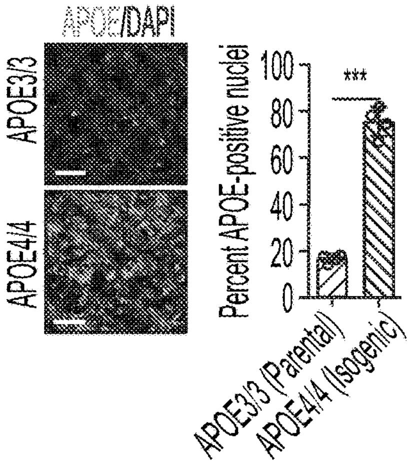
Figure 4D:
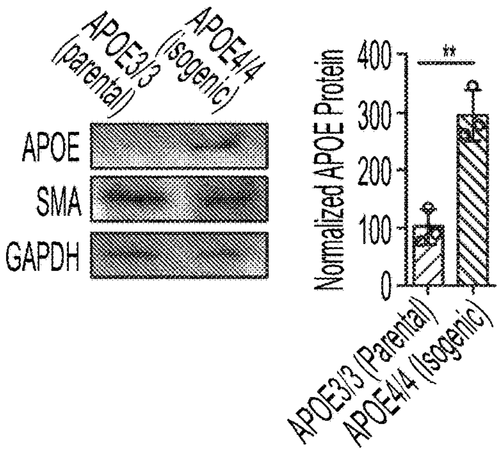
Figure 4E:
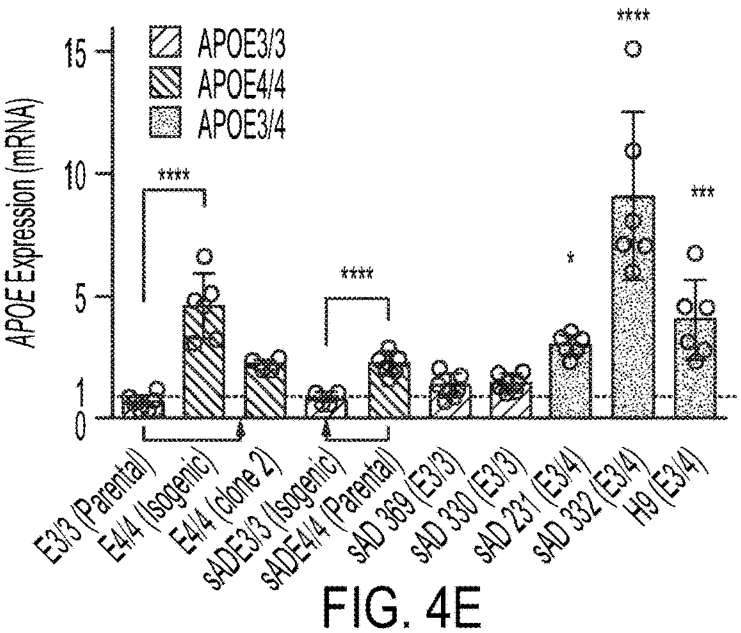
Figures 10C, 10D, 10E, 10F:
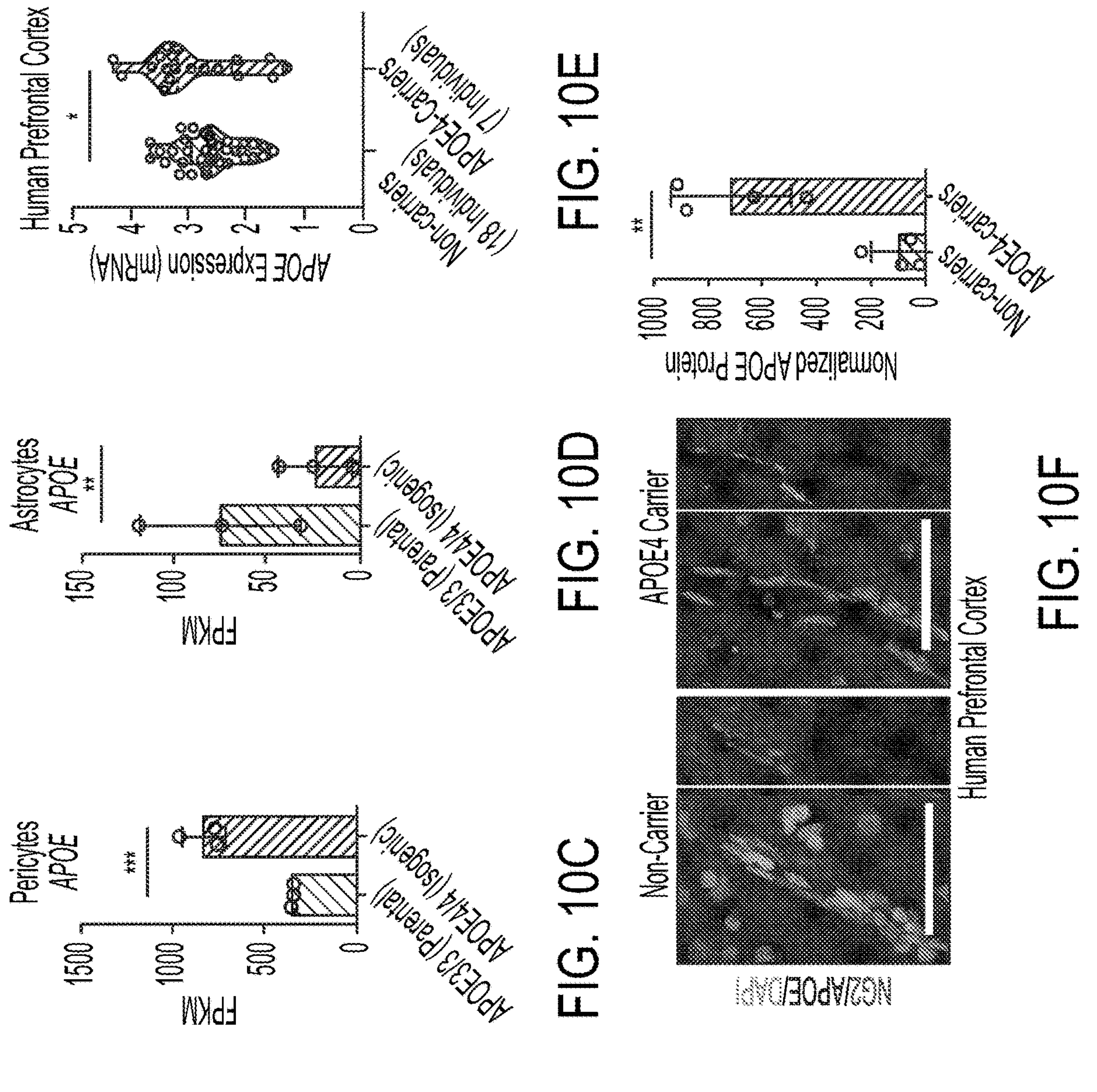

Example 4: APOE and Calcineurin Signaling are Up-Regulated in APOE4 Pericytes To further examine how pericytes and APOE4 jointly promote increased amyloid deposition we next performed global transcriptional profiling of isogenic iPSC-derived APOE3/3 and APOE4/4 pericytes. Previously, we found that hundreds to thousands of genes were differentially expressed between isogenic E3/3 and E4/4 cells including iPSCs (150 genes), neurons (443 genes), astrocytes (1325 genes), and microglia-like cells (1458 genes) generated from the same iPSC lines. We found a much larger number of genes (4286) to be differentially expressed (DEGs; $q<0.05$) between isogenic pericytes with 2,303 genes significantly up-regulated and 1,983 genes down-regulated in E4/4 pericytes (FIG. 4*a*). Gene ontology analysis suggested that the biological processes involved in protein targeting to the membrane and endoplasmic reticulum are up-regulated in APOE4 pericytes whereas mitosis and cell cycle progression are down-regulated (FIGS. 10*a* and *b*). Previously, we observed the expression of APOE in E4/4 astrocytes to be down-regulated. Similar to previous reports in mice, we found human iPSC-derived pericytes highly express APOE based on relative comparison of astrocyte and pericyte APOE FPKM values from RNA-sequencing (FIG. 10*c*). However, in striking contrast to astrocytes, pericytes exhibited robust up-regulation of APOE in E4/4 pericytes whereas genetically identical E4/4 astrocytes exhibited the reverse expression profile with reduced level of APOE compared to E3/3 (FIG. 10*d*). We confirmed differential up-regulation and down-regulation of APOE in pericytes and astrocytes respectively via qRT-PCR of RNA harvested from samples independent from the RNAseq samples (FIG. 4*b*). We found that increased APOE gene expression in E4/4 pericytes translates to an increase in protein via immunofluorescence imaging and western blotting (FIGS. 4*c* and *d*). APOE gene expression was also up-regulated in E4/4 pericytes from our reciprocal isogenic pair suggesting the effect is unlikely to be an artifact of genetic editing or clonal variation (FIG. 4*e*). Furthermore, pericytes from multiple APOE3/4 heterozygous individuals consistently expressed higher APOE mRNA than E3/3 pericytes including E3/3 pericytes generated from non-edited iPSC (FIG. 4*e*).

Figure 4F:
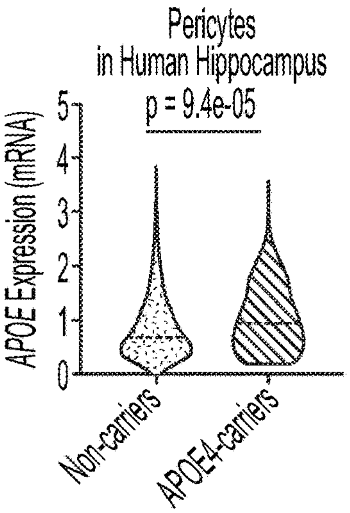
Figure 4G:
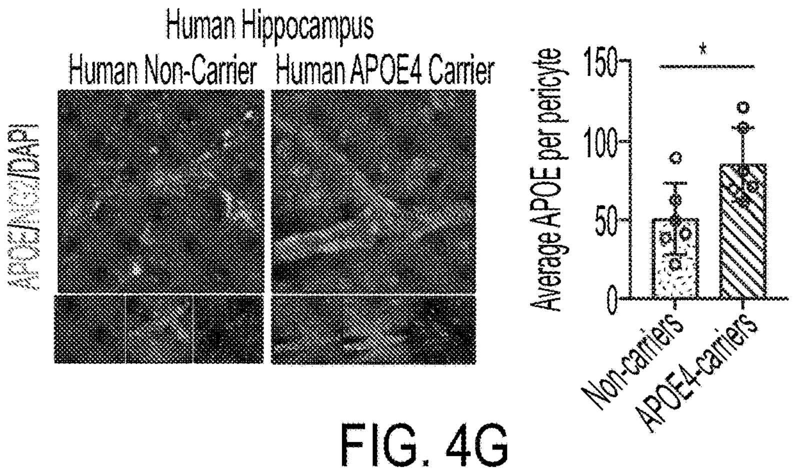
Figure 10H:
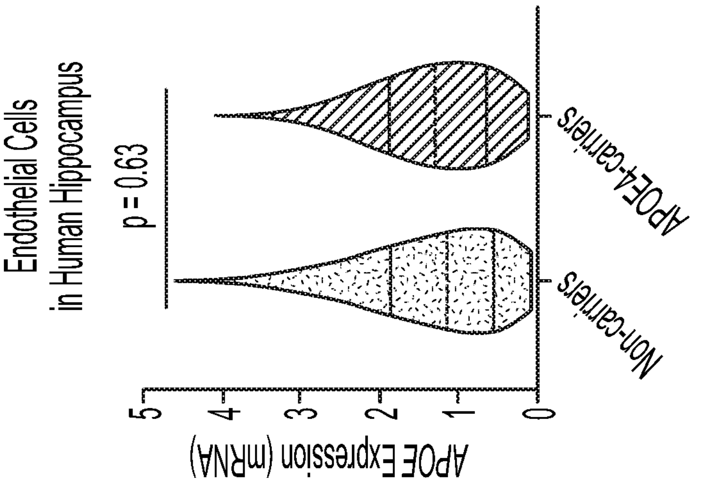
Figure 10G:
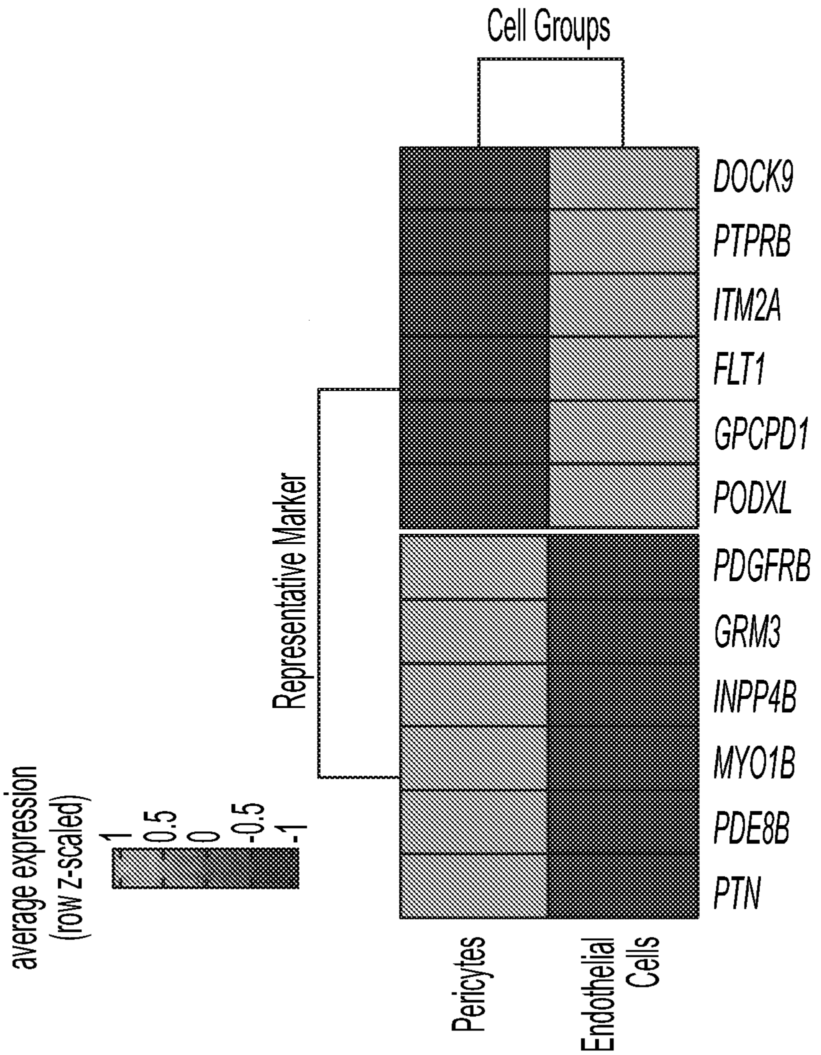

To confirm the relevance of these findings in the human brain we employed single-nucleus RNA-sequencing (snRNAseq) to assess the expression of APOE in pericytes and endothelial cells from our recently published single cell transcriptomic study of the BA10 region of human prefrontal cortex using single-nucleus RNA-seq. We found that the transcriptional cluster of pericytes partially overlapped with that of endothelial cells. To simplify our analysis, we treated the two cell populations as a single pericyte/endothelial cluster. We found that cortical pericytes/endothelial cells from APOE4-carriers (n=7 individuals) exhibited significantly higher APOE mRNA expression compared to non-carriers (n=18 individuals) (FIG. 10*e*). In addition to scRNAseq we performed immunohistochemistry to specifically examine the expression of APOE in human brain pericytes. In the human prefrontal cortex, we found that APOE protein expression in the NG2-positive pericytes from APOE4-carriers (n=4 individuals) was significantly elevated compared to non-carriers (n=4 individuals) (FIG. 10*f*). To further assess whether APOE is elevated in in vivo APOE4 pericytes from other brain regions we analyzed snRNAseq data of the hippocampus of APOE4-carriers (n=16 individuals) and non-carriers (n=46 individuals). A larger number of cells from the hippocampus dataset enabled a clear separation of endothelial cells and pericytes based on marker gene expression (FIG. 10*g*). Similar to the prefrontal cortex, we found that expression of APOE in hippocampal pericytes from APOE4-carriers was significantly higher compared to non-carriers (FIG. 4*f*) whereas in endothelial cells there was no significant difference in APOE expression between APOE4-carriers and non-carriers (FIG. 10*h*). To further validate this observation, we analyzed APOE expression in human hippocampal pericytes using immunohistochemistry from a different cohort of APOE4-carriers and non-carriers. Similar to snRNAseq we observed that APOE4-carriers (n=6 individuals) exhibited significantly higher APOE immunoreactivity that non-carriers (n=6 individuals) in NG2-positive pericytes (FIG. 4*g*). Collectively, these results are consistent with the notion that in vivo human brain pericytes from APOE4-carriers express higher APOE than pericytes from non-carriers across multiple brain regions.

Figure 4H:
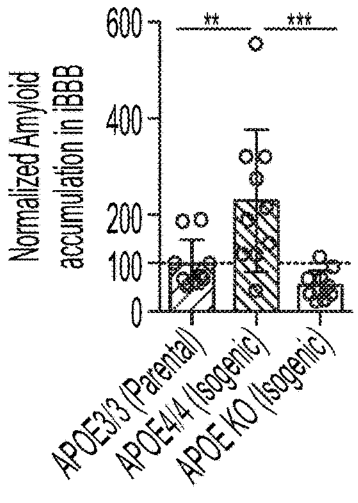
Figure 4I:
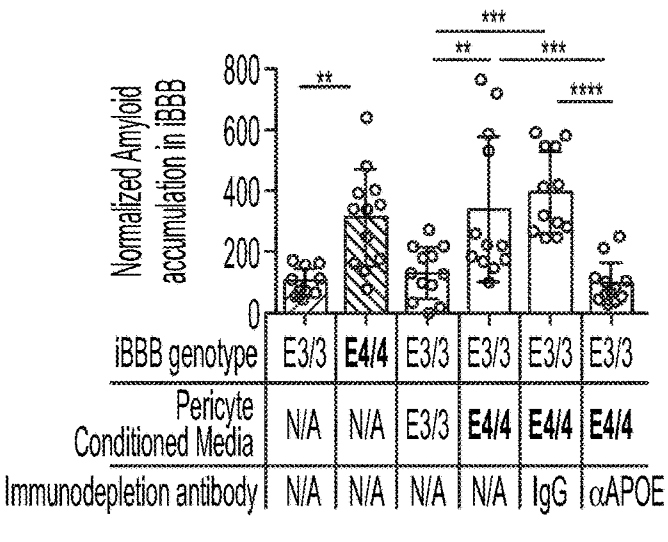
Figure 11A:
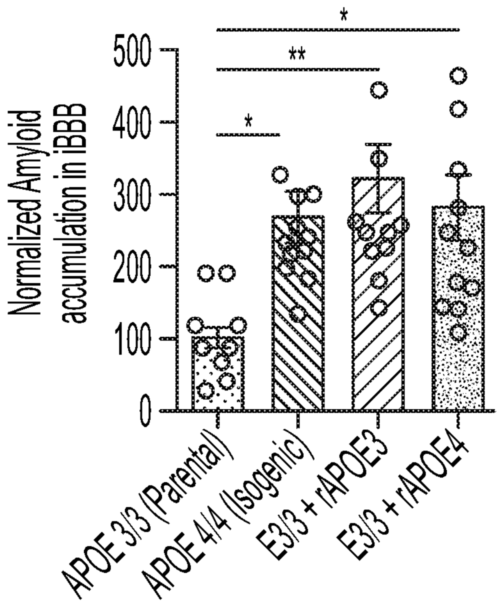
FIGS. 11A-11L. 11A, Increasing the soluble APOE concentration through the addition of recombinant APOE protein to iBBB culture increases amyloid accumulation. One-way ANOVA with Bonferroni's post-hoc analysis (p=0.0011)K 11B and 11C, Representative western blot and quantification depicting nuclear NFATc1 expression in isogenic APOE3 and 4 pericytes. Unpaired student t test, p=0.0254. 11D, Expression of calcineurin catalytic subunits measured by RNAseq. PPP3CA (q=0.0003); PPP3CC (q=0.0188). 11E, Expression of negative Regulators of Calcineurin genes (RCANs) measured by RNAseq. RCAN2 (q=0.0003); RCAN3 (q=0.0123). 11F, Expression of DYRKs kinases known to phosphorylate NFAT measured by RNAseq. DYRK4 (q=0.0003). 11G, Expression of predicted NFAT response gene, VCAM1 and ACTG2, in pericytes. Expression is quantified by qRT-PCR and normalized to the average of E3/3 cells. Significance determined by One-way ANOVA (p<0.0001) with Bonferroni's multiple comparison. 11H and 11I, Violin plots depicting NFATC1 (h) and NFATC2 (i) expression in pericytes isolated from post-mortem prefrontal cortex of APOE4-carriers (n=16) compared to non-carriers (n=46). Differential expression was measured using a two-tailed Wilcoxon rank sum test, considering cells with detected expression of APOE. 11J and 11K, Violin plots depicting NFATC1 and NFATC2 expression in endothelial cells isolated from post-mortem hippocampus of APOE4-carriers (n=16) and non-carriers (n=46). Differential expression 11L, Violin plots depicting NFATC2 expression in endothelial cells isolated from post-mortem prefrontal cortex of APOE4-carriers (n=7 compared to non-carriers (n=18). Differential expression was measured using a two-tailed Wilcoxon rank sum test, considering cells with detected expression of APOE (p=0.035).

APOE is a soluble protein that binds Aβ promoting its interaction with cells and the extracellular environment. Mouse knockout studies have demonstrated that APOE is required for CAA pathologies and haploinsufficiency of APOE3 and APOE4 reduces cerebral amyloid accumulation in knock-in mice. Therefore, the increased expression of APOE observed in E4 pericytes could promote the increased seeding and deposition of amyloid observed in APOE4 iBBBs and human carriers. To explore this scenario, we generated isogenic APOE deficient iPSC lines using CRISPR/Cas9 editing. We then produced isogenic iBBBs that were E3/3, E4/4, or deficient for APOE (Knockout, KO). Again E4/4 iBBBs displayed higher levels of amyloid accumulation compared to E3/3. In contrast, APOE-deficient iBBBs had reduced levels of florescent Aβ accumulation similar to the E3/3 iBBBs (FIG. 4*h*). To test whether APOE is directly required for increased amyloid accumulation, we first immunodepleted APOE from pericyte conditioned media and then exposed the APOE3 iBBBs to APOE-depleted or control media (non-specific IgG or no depletion). These cultures were subsequently exposed to fluorescently labeled Aβ for 96 hours. Immuno-depletion of APOE from the APOE4/4 pericyte conditioned media led to a significant reduction in the accumulation of Aβ compared to non-depleted or non-specific IgG depleted controls (FIG. 4*i*). This suggests that elevated APOE concentrations increase amyloid deposition. To further examine this hypothesis, we next used recombinant human APOE protein to increase the concentrations of APOE in the APOE3 iBBB culture media to approximately the levels observed in APOE4 iBBB culture media (200 ng/ml) and subsequently exposed these iBBB to fluorescently labeled Aβ for 96 hours. We found that increasing APOE concentrations, regardless of E3 or E4, was sufficient to increase Aβ accumulation in APOE3/3 iBBB to similar levels in APOE4 to levels (FIG. 11*a*). This demonstrates that APOE protein abundance directly correlates with amyloid accumulation. Therefore, given that pericytes are an abundant source of APOE, we hypothesized that reducing APOE protein in APOE4 pericytes could lead to reduced amyloid accumulation.

Figure 4J:
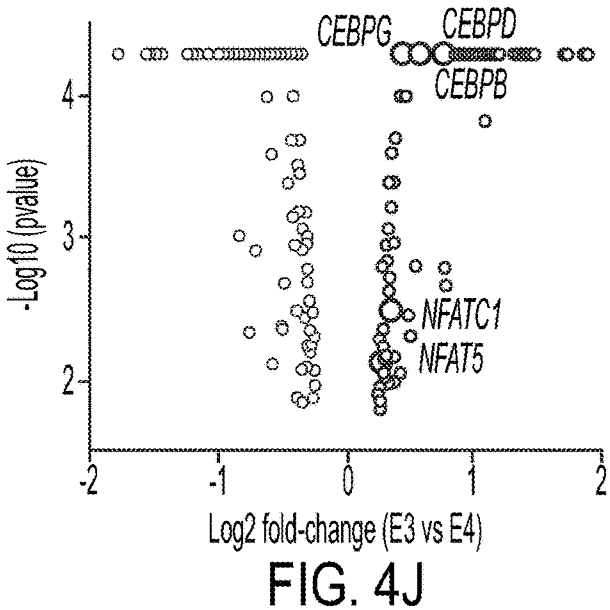

Next, we sought to identify regulatory pathways underlying the differential expression of APOE genotypes in pericytes. In particular, we were interested in potential DNA binding proteins that may mediate the up-regulation of APOE in E4 pericytes. Thus, we first identified all transcription factors differentially expressed between isogenic E3/3 and E4/4 pericytes. In E4/4 compared to isogenic E3/3 pericytes 127 transcription factors were differentially up-regulated and 101 down-regulated (with q<0.05) (FIG. 4*j*). To pinpoint transcription factors that could regulate APOE expression, we next assessed whether any of the differentially expressed transcription factors have been reported to bind APOE gene regulatory elements. Up-regulation of NFATs and C/EBPs in E4/4 pericytes suggests that the increased expression of either NFAT or C/EBP in E4/4 pericytes could contribute to the increased expression of APOE. We found the up-regulation of NFAT signaling particularly interesting because a dysregulation of NFAT, its upstream effector calcineurin, and calcium signaling have been observed during aging, AD, and cognitive decline. However, the mechanistic details underlying these observations are limited.

Figure 4K:
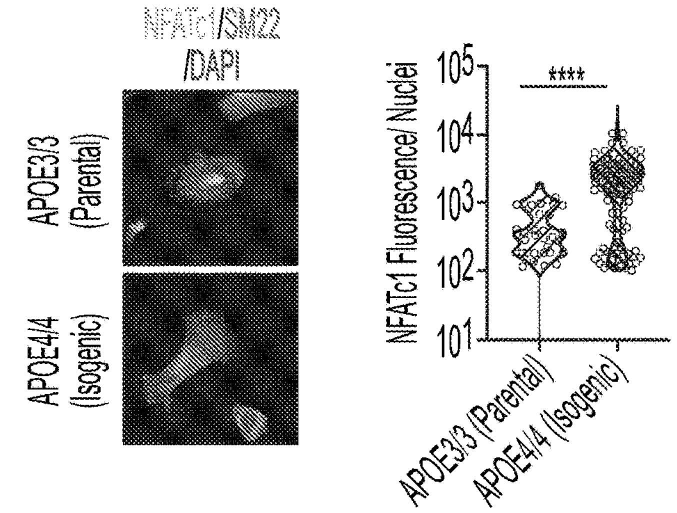
Figure 11B:
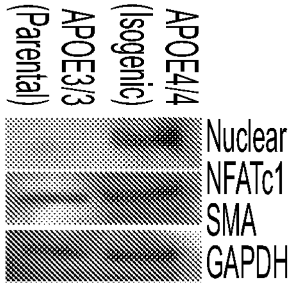
Figure 11C:
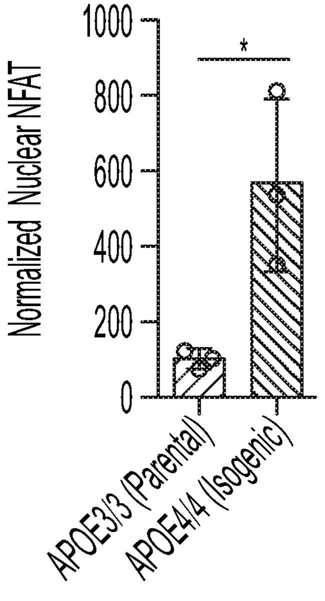
Figure 11D:
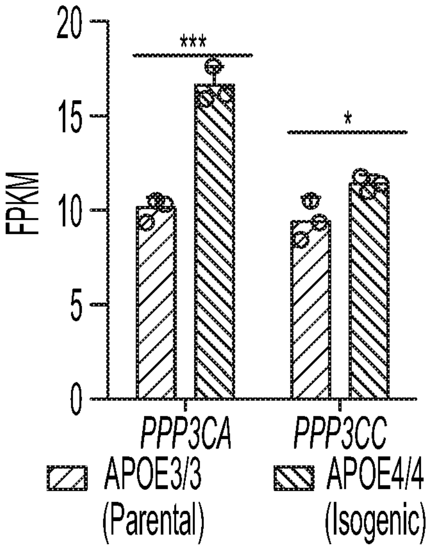
Figure 11E:
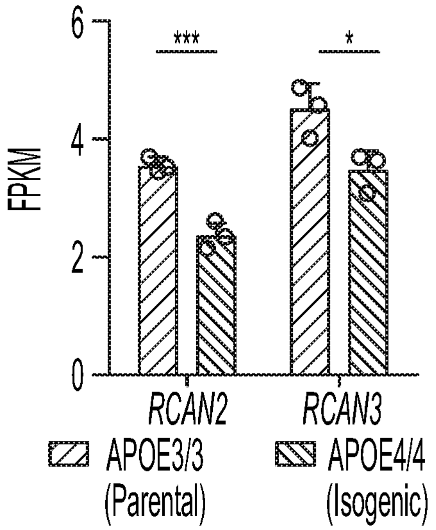
Figure 11F:
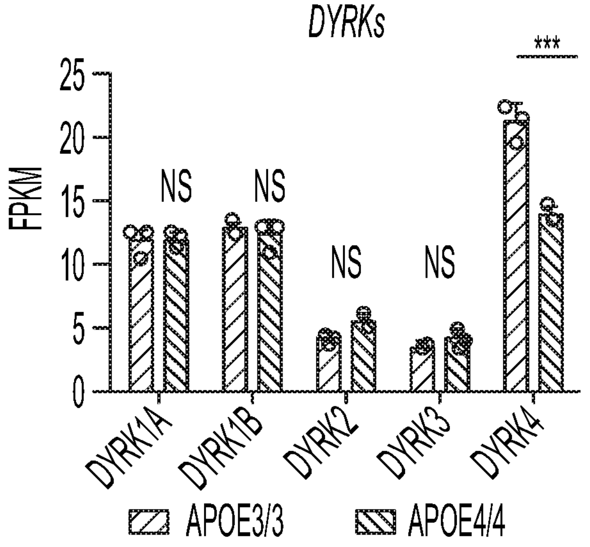
Figure 11G:
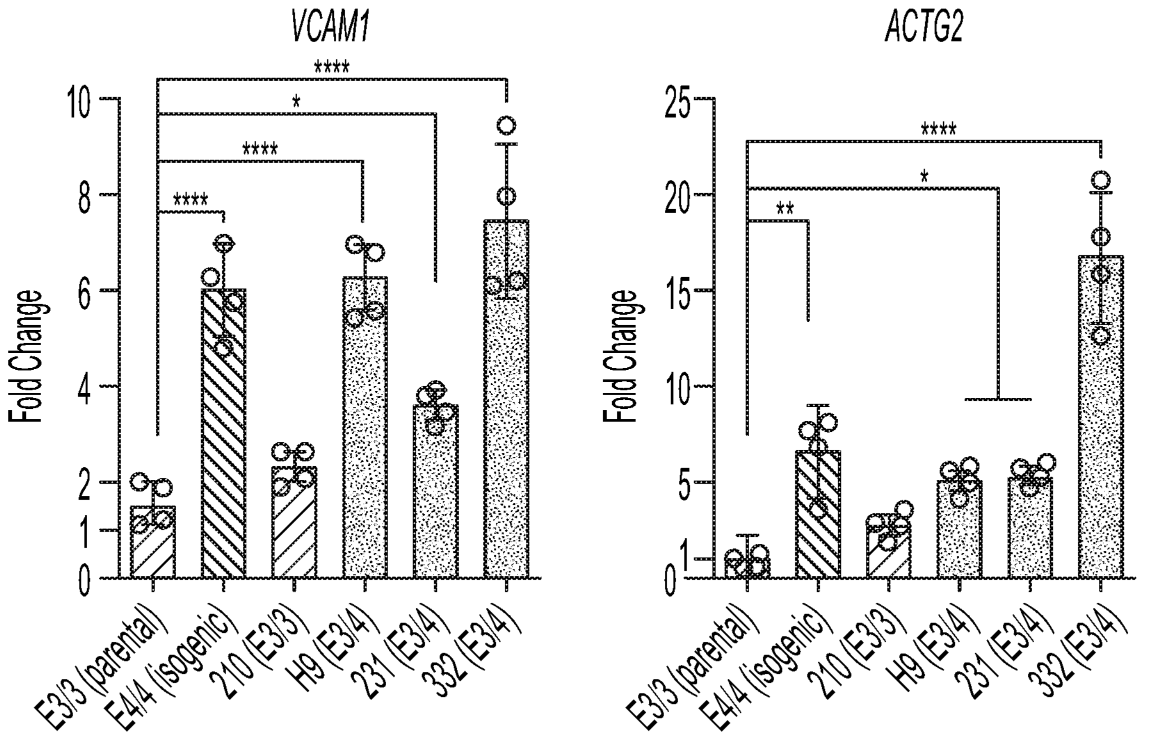
Figure 11H:
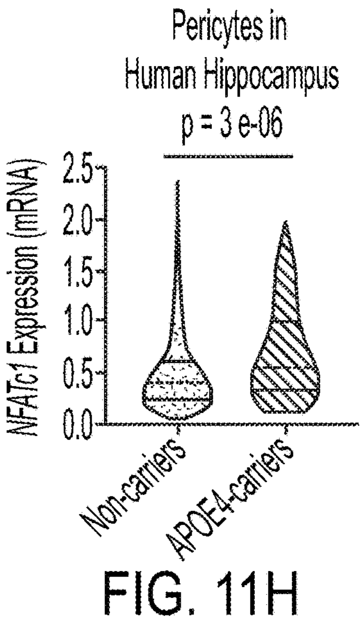
Figure 11I:
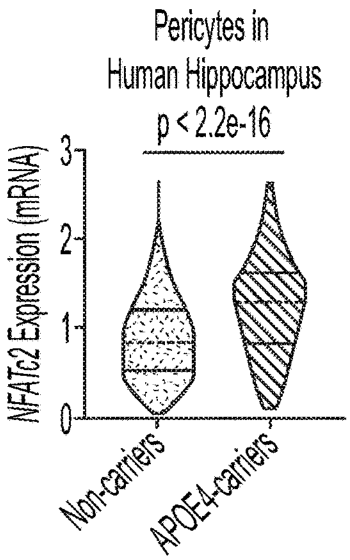
Figure 11J:
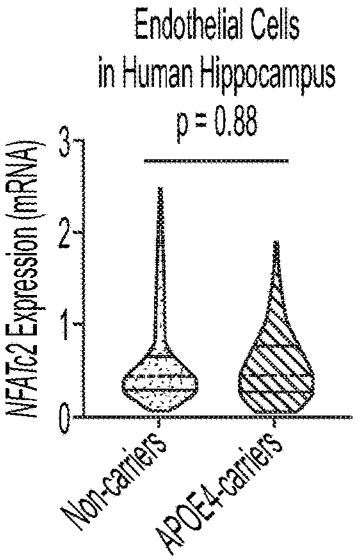
Figure 11K:
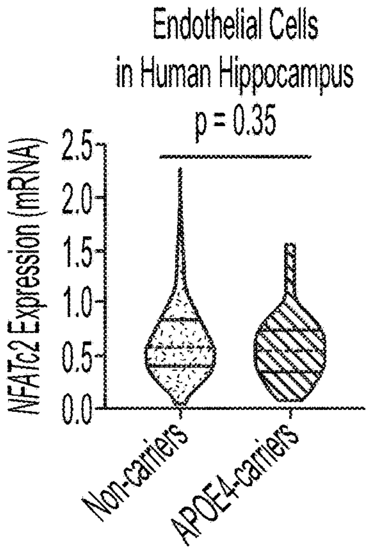

We confirmed that E4 pericytes contain significantly higher cytoplasmic and nuclear NFATc1 protein by immunostaining and western blotting (FIG. 4*k*; FIGS. 11*b* and *c*). Furthermore, the genes encoding the catalytic subunits of CaN, PPP3CA and PPP3CC were significantly up-regulated (49.8% and 26.5%, respectively) in E4/4 pericytes (FIG. 11*d*). In contrast, negative Regulators of Calcineurin, RCAN2, and RCAN3, kinases that phosphorylate and inhibit CaN phosphatase activity, were down-regulated (−23.7% and −27.7%, respectively) in E4/4 pericytes (FIG. 11*e*). Similarly, in APOE4/4 iPSC-derived pericytes, we observed that DYRK4, a kinase that phosphorylates NFAT promoting its cytoplasmic retention, was significantly down-regulated (−38.9%) (FIG. 11*f*). We did not observe significant changes in DYRK 1-3 by RNA-sequencing (FIG. 110. Collectively, these results indicate that E4/4 pericytes exhibit bidirectional alterations of intracellular molecules consistent with elevated CaN/NFAT-signaling yielding an environment that could actively promote NFAT-mediated transcription. To test this, we examined by qRT-PCR whether genes reported to be NFAT-responsive in pericytes are up-regulated in E4 pericytes. Consistently, both ACTG2 and VCAM1 were significantly up-regulated across both E4 homo- and heterozygous pericytes (FIG. 11*g*).

Figure 4L:
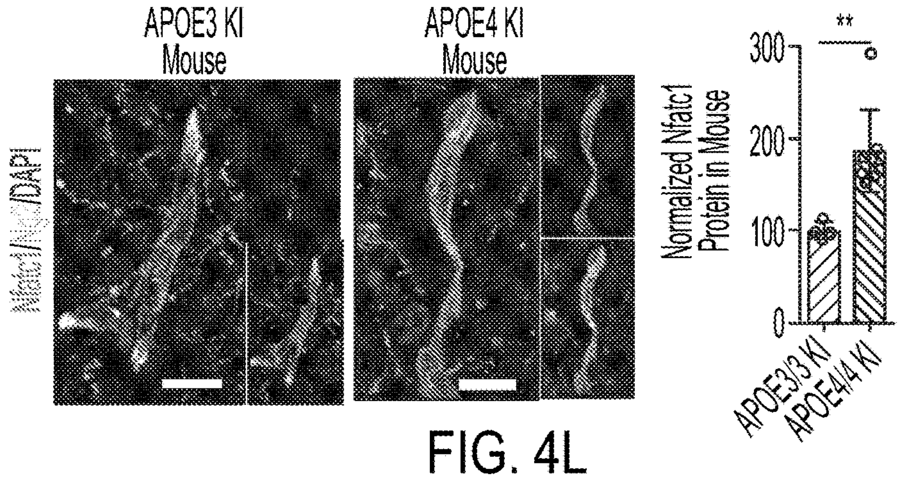
Figure 11L:
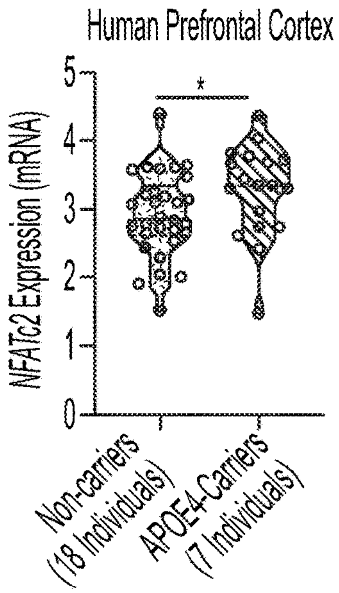

To examine whether NFAT is upregulated in APOE4 pericytes in vivo, we first examined Nfatc1 expression in mice in which the murine APOE coding region was genetically replaced with either the human APOE3 or APOE4 coding regions. Comparing APOE expression in Ng2-positive pericytes using immunohistochemistry, we found that APOE4 knock-in mice (APOE4KI) exhibited approximately 86% higher Nfatc1 protein staining in brain vascular Ng2-positive pericytes compared to APOE3 knock-in (APOE3KI) mice (FIG. 4*l*). Similarly, snRNA-seq transcriptomics analysis of the human hippocampus revealed that both NFATc1 and NFATc2 are significantly higher in pericytes from APOE4-carriers (n=16 individuals) relative to non-carriers (n=46 individuals) (FIGS. 11*h* and *i*) whereas neither NFATc1 or NFATc2 are differentially expressed in endothelial cells (FIG. 11 *j* and *k*). In the prefrontal cortex, we also observed significant upregulation of NFATc2 mRNA in human cortical pericytes/endothelial cells from APOE4-carriers via snRNAseq (FIG. 11*l*). Collectively, multiple lines of in vitro and in vivo evidence suggest that several components of the NFAT/CaN signaling pathway are altered in E4 pericytes, which could promote the expression of APOE and lead to APOE4-mediated amyloid accumulation.

Figure 5A:
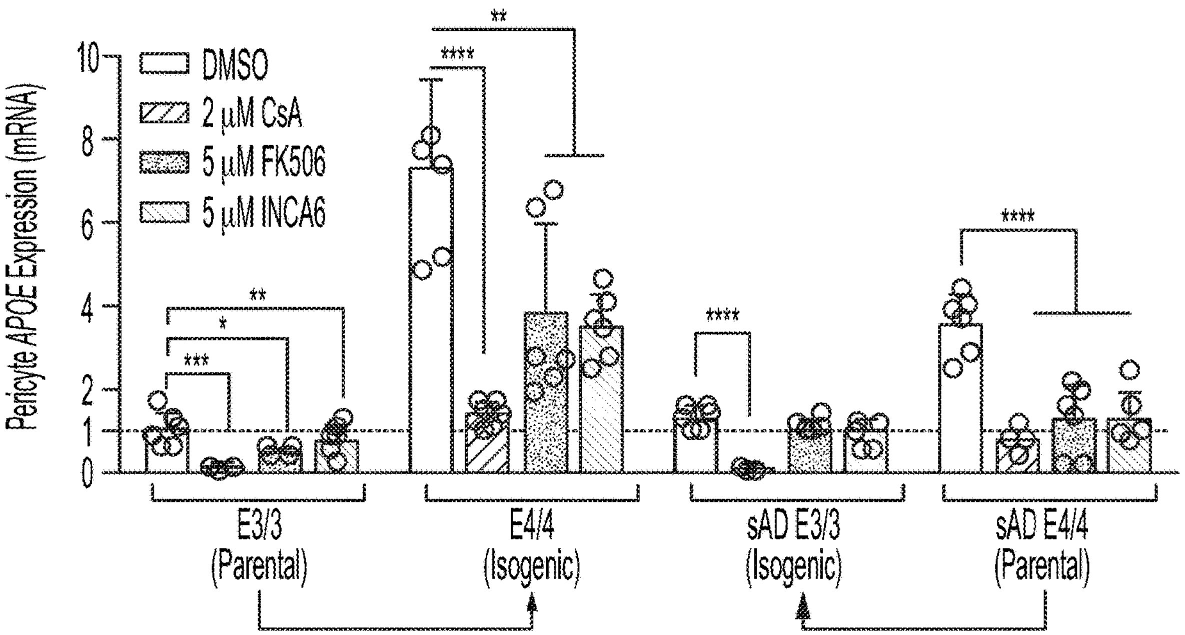
FIGS. 5A-5N. Inhibition of Calcineurin reduces APOE expression and ameliorates Aβ deposition 5A and 5B Expression of APOE in isogenic (a) and heterozygous (b) pericytes after two weeks treatment with DMSO, CsA, FK506 or INCA6. One-way ANOVA (p<0.0001) with Bonferroni's multiple comparison. 5C, Soluble APOE protein is significantly reduced following two-week treatment with calcineurin inhibitor CsA. APOE concentration in pericyte conditioned media was quantified using ELISA from three separated biological replicates. Multiple Student t-tests. Discovery determined using FDR method with Benjamini and Hochberg with Q=1%. 5D and 5E, Expression of NFATc1 (d) and APOE (e) is down-regulated in pericytes by CsA treatment. Bars are mean value from 3 biological replicates One-way ANOVA (NFATc1, p=0.0013; APOE, p<0.0001) with Bonferroni's multiple comparison 5F, Heat map depicting differentially expressed genes between isogenic APOE3/3 pericytes treated with DMSO and APOE4/4 pericytes treated with DMSO, or 2 μM CsA. Genes and organized by hierarchical clustering using Spearmann's Rank correlation with average linkage. Boxes outline genes clustering together. The total genes for each cluster are presented on the right side of the heatmap depicted values are mean normalized counts from 3 independent biological replicates 5G, Representative images of E4/4 pericytes treated with DMSO, CsA, or FK506 for two weeks and then exposed to 20 nM Aβ-FITC for 96 hours. 5H, Quantification of Aβ accumulation in iBBBs treated with DSMO, CsA, or FK506. iBBBs were pre-treated with chemicals for two weeks and then exposed to 20 nM Aβ for 96 hours. Significance determined via One-way ANOVA ($p<0.0001$) with Bonferroni's multiple comparison. (Scale bar=10 μm) 5I, Quantification of Aβ accumulation in APOE3/4 heterozygous iBBBs treated with DSMO, CsA, or FK506. iBBBs were pre-treated with chemicals for two weeks and then exposed to 20 nM Aβ for 96 hours. Significance determined via One-way ANOVA ($p<0.0001$) with Bonferroni's multiple comparison. 5J, Quantification of Aβ accumulation in iBBBs treated with conditioned media from APOE4/4 pericyte that were treated with calcineurin inhibitors for one at least week prior media harvesting. One-way ANOVA ($p<0.0001$) with Bonferroni's multiple comparisons. 5K, APOE protein concentration in the hippocampus of mice treated with either cyclosporine A or vehicle. APOE was measured by ELISA. Each dot represents mean APOE concentration from one mouse. Unpaired two-tailed t test ($p=0.0456$). 5L, Representative image and quantification of immunostaining for APOE in cortical pericytes from APOE4 KI×5×FAD mice treated with cyclosporine A or vehicle. Unpaired two-tailed t test ($p=0.0427$). 5M, Representative image of concurrent reduction of vascular APOE protein and amyloid following a three-week treatment with CsA. 5N, Representative images and quantification of vascular amyloid in the hippocampus following treatment of 6-month-old APOE4KI×5XFAD female mice with either vehicle or CsA for three weeks. Amyloid was detected and quantified with two independent anti-amyloid antibodies (6e10 and 12F4). Unpaired two-tailed t test (6e10, $p=0.0055$; 12F4, $p=0.0242$). (Scale Bars=25 μm).
Figure 5B:
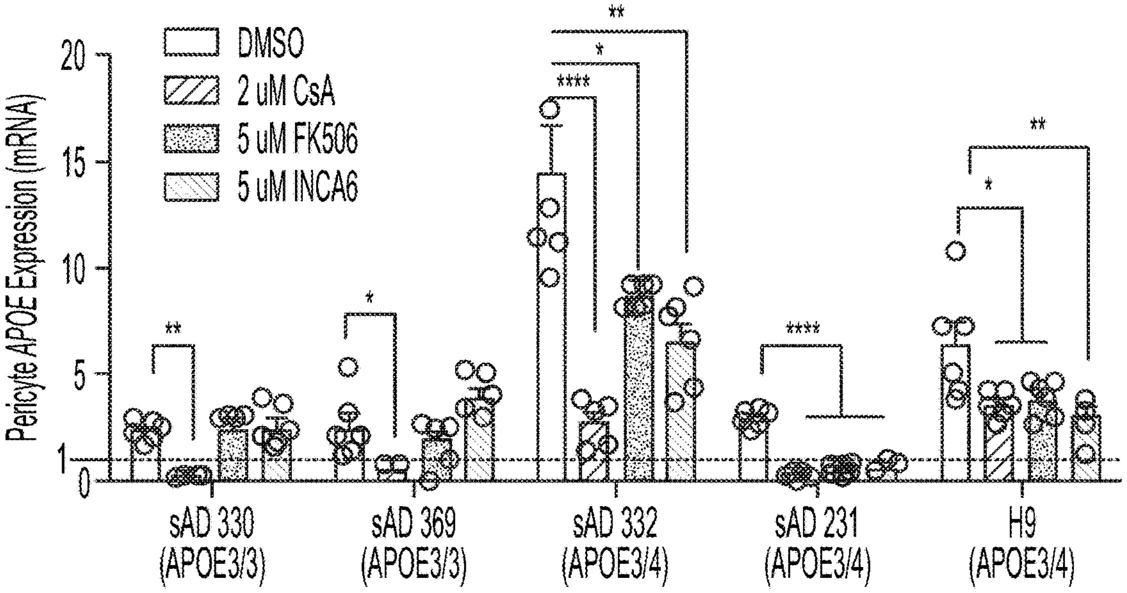
Figure 5C:
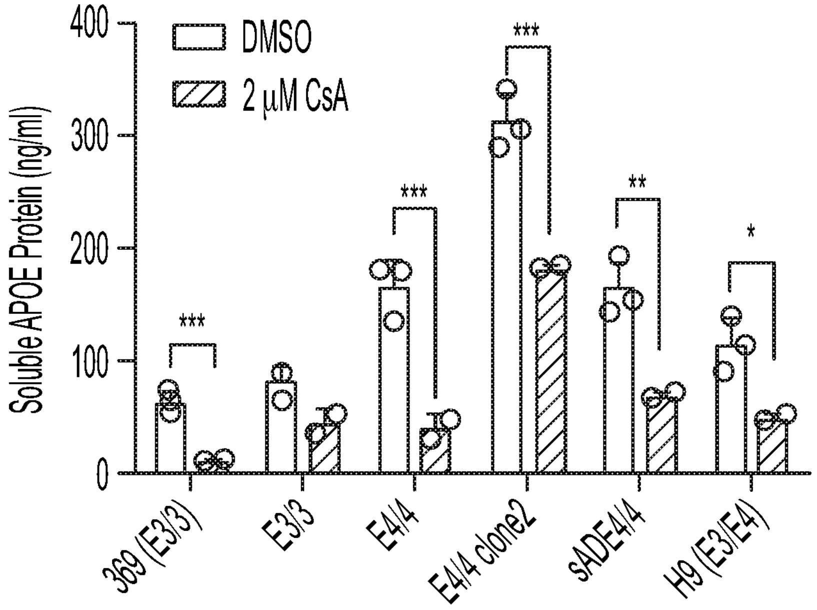
Figure 12A:
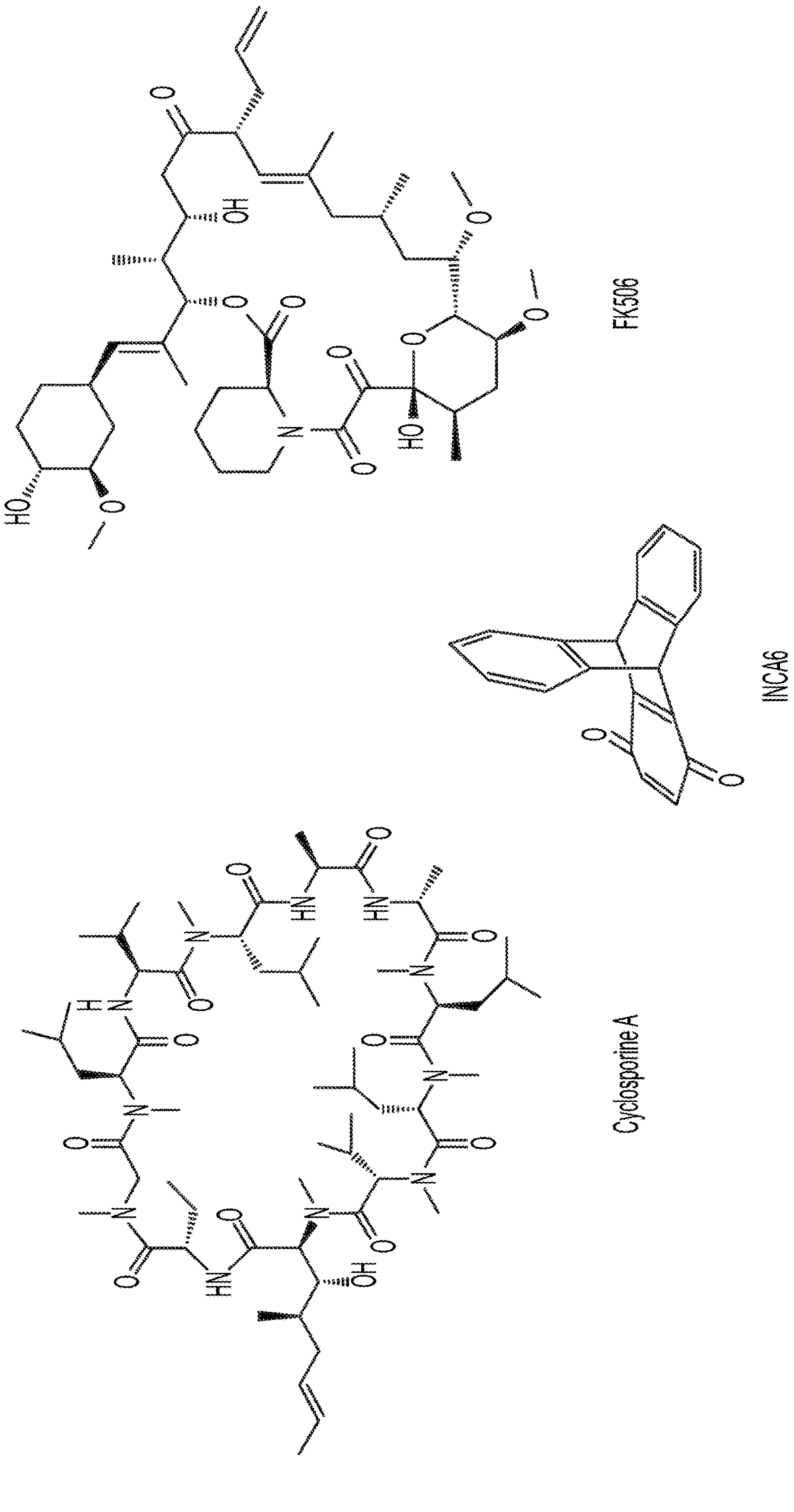
Figure 12B:
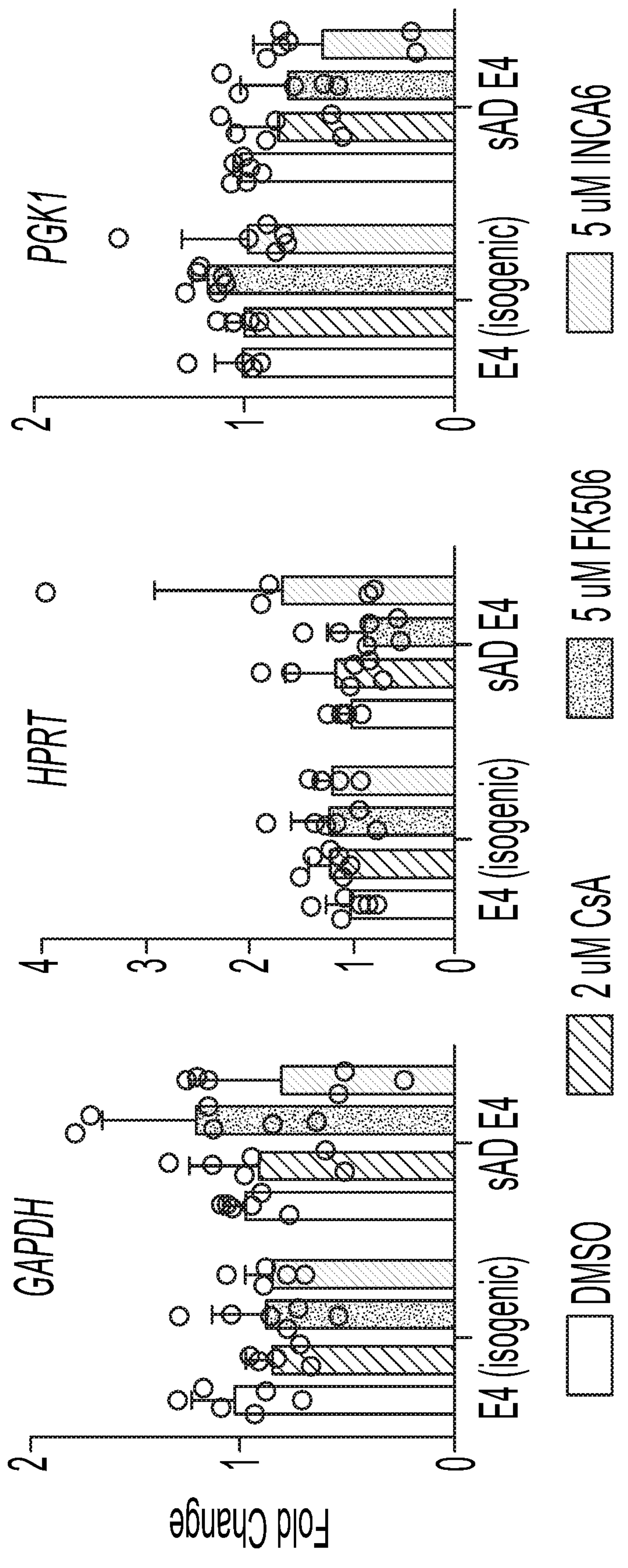
Figure 12D:
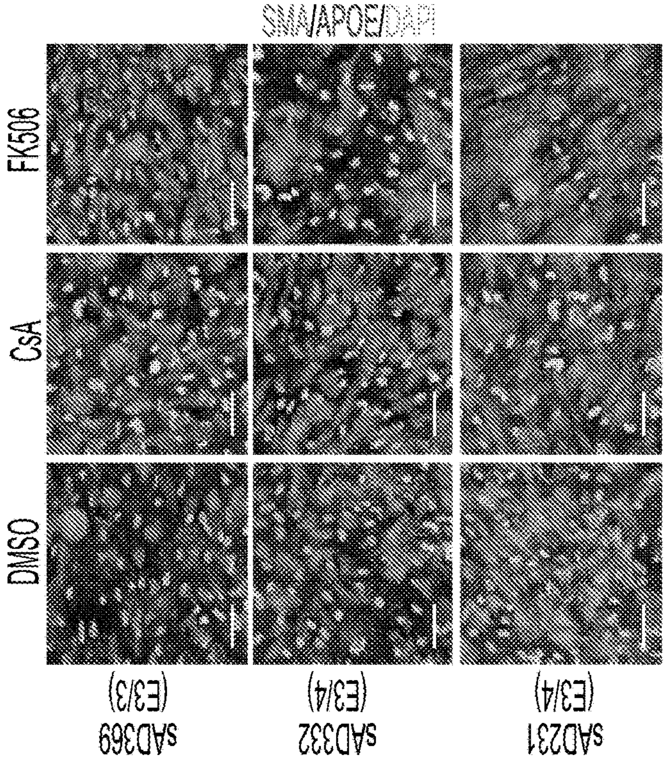
Figure 12C:
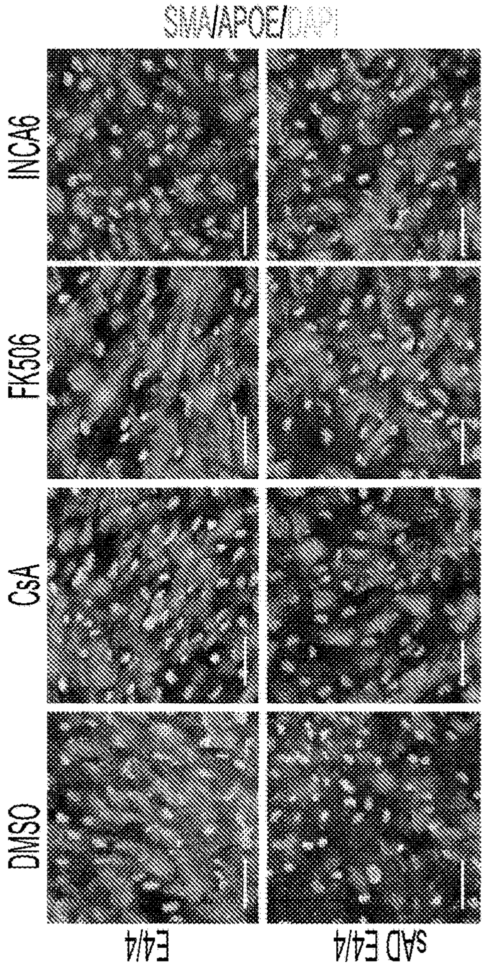

Example 5: Inhibition of Calcineurin (CaN) Reduces APOE Expression and Ameliorates Aβ Deposition To determine if dysregulation of the calcineurin pathway in E4/4 pericytes contributes to up-regulated APOE expression, we set out to inhibit calcineurin signaling using well-established CaN inhibitors cyclosporine A (CsA) (2 μM), FK506 (5 μM), and INCA6 (5 μM) (FIG. 12*a*). After two weeks of CaN inhibition independently with each of the three inhibitors, APOE expression was significantly reduced in APOE4/4 pericytes as measured by qRT-PCR (FIG. 5*a*). Calcineurin inhibition also tended to reduce APOE gene expression in APOE3/3 pericytes, however given the lower expression of APOE the trend was more modest (FIG. 5*a*). Inhibition of CaN did not significantly reduce constitutively expressed proteins such as PGK1, HPRT, and GAPDH, suggesting that APOE down-regulation is not a result of cellular death or global transcriptional repression (FIG. 12*b*). To examine whether inhibition of CaN also reduced the expression of APOE in E3/4 heterozygous pericytes, we treated pericytes derived from three E3/4 individuals and two additional E3/3 control individuals. Similar to homozygous E4/4 pericytes, E3/4 heterozygous pericytes exhibited a significant reduction in the expression of APOE when treated with each of the three CaN inhibitors (FIG. 5*b*). In addition to APOE gene expression, inhibition of CaN also reduced intracellular APOE protein measured by immunofluorescence in both E4/4 homozygous and E3/4 heterozygous lines (FIGS. 12*c* and 12*d*). Likewise, CsA also significantly reduced the concentration of soluble APOE protein present in the media of cultured pericytes when measured by ELISA (FIG. 5*c*). Together, these results establish that chemical inhibition of CaN in E4 pericytes leads to a reduction in both APOE gene expression and APOE protein.

Figure 5D:
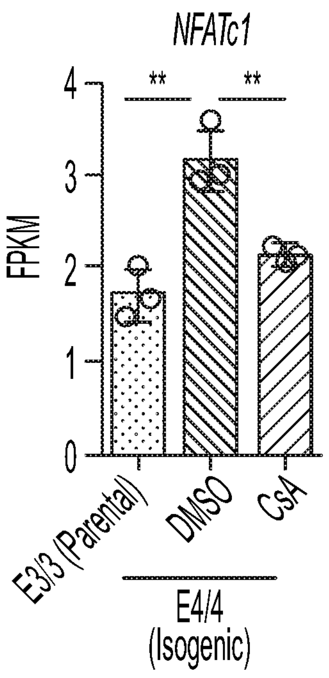
Figure 5E:
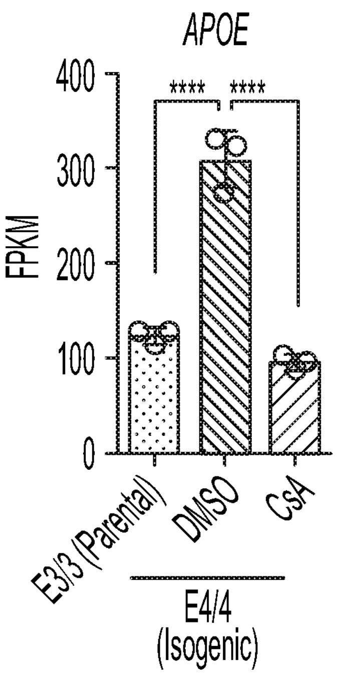
Figure 5F:
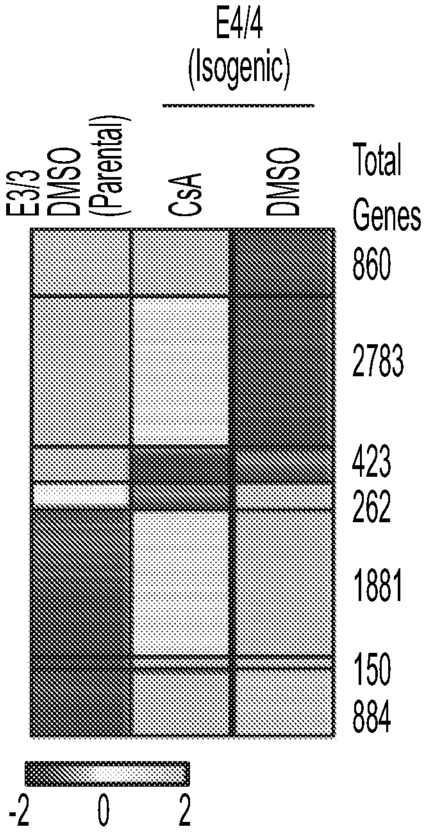

To capture an unbiased assessment of additional changes that occur when CaN is inhibited in E4 pericytes we performed global transcriptional profiling of E3/3 pericytes treated with DMSO and isogenic E4/4 pericytes treated with either DMSO or 2 μM CsA. In CsA treated pericytes the expression of NFATc1 was significantly down-regulated to a comparable level observed in E3/3 DMSO treated pericytes (FIG. 5*d*). As predicted, down-regulation of NFATc1 by CsA correlated with reduced expression of APOE in E4 pericytes in agreement with the qRT-PCR data presented in FIG. 4 *b*(FIG. 5*e*). E4/4 pericytes treated with DMSO exhibited more than 4,000 differentially expressed genes compared to E3/3 pericytes treated with DMSO (FIG. 5*f*). In contrast, E4/4 pericytes treated with CsA exhibited a transcriptional profile closer to E3/3 pericytes (FIG. 5*f*). CsA led to upregulation of 860 genes that exhibited similar expression levels to E3/3 DMSO-treated pericytes (FIG. 5*f*). Gene ontology (GO) analysis suggests that these genes are involved in RNA processing (GO:0006396, GO:0016071, and GO:0034660), and processes associated with peptide synthesis (GO:0043604 and GO:0043043) (FIG. 11*e*). 2,783 genes exhibited moderate up regulation in response to CsA reaching intermediate expression levels that were in between E3/3 and E4/4 pericytes. GO analysis categorized these genes to be involved in intracellular protein transport and localization (GO:0006886, GO:0015031, and GO:0034613), cellular catabolic processes and macromolecule localization (GO:0044248 and GO:0070727) (FIG. 12*e*). Interestingly, the genes down-regulated in E4/4 pericytes by CsA showed a more modest similarity to E3/3 pericytes (FIG. 5*f*). CsA-treatment led to down-regulation of 1881 genes to expression levels that were in between E3 and E4 pericytes (FIG. 5*f*). GO analysis of these genes suggests involvement in GTPase activity and neural tube closure (GO:0043087, GO:0051056, GO:0043547, GO:0007264, GO:0001843). Overall, treatment of E4 pericytes with CsA led to increased transcriptional similarity to E3/3 pericytes with Spearman's rank correlation analysis demonstrating that while DMSO treated E4/4 pericytes exhibited a global transcriptional profile similarity of 0.889 with E3 pericytes, CsA treatment increased that similarity to 0.937. This suggests that pharmacological inhibition of CaN in E4 pericytes broadly imparts transcriptional changes leading to increased similarity with E3 pericytes. In T cells CaN/NFAT is associated with inflammatory responses and up-regulation of inflammatory response genes including interleukins and tumor necrosis factors. While we observed elevated CaN/NFAT signaling in E4 pericytes we did not observe significant up-regulation of classical inflammatory genes suggesting that the CaN/NFAT response is likely cell-type specific.

Figure 5G:
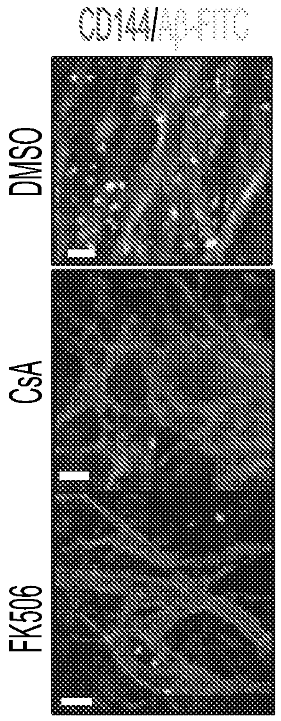
Figure 5H:
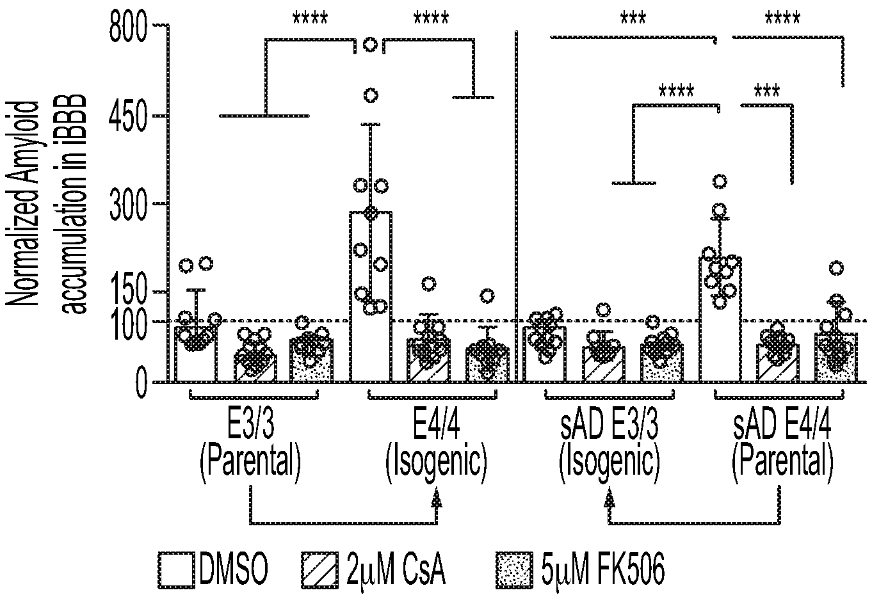
Figure 5I:
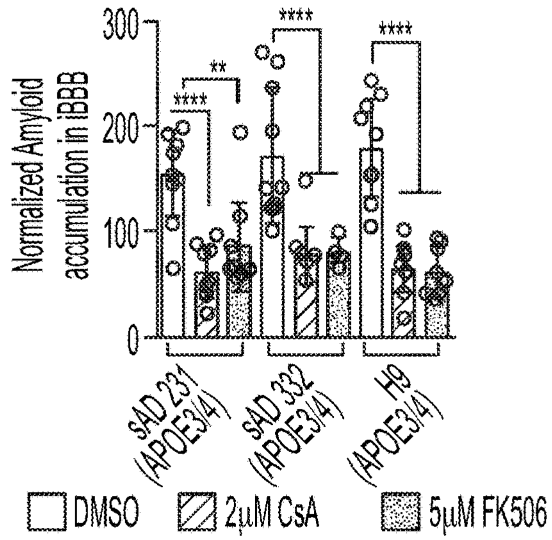

APOE is required for high levels of amyloid deposition in vivo and in our iBBB (FIGS. 4*h* and *i*; FIG. 10*g*). Therefore, a reduction in APOE protein could also reduce amyloid deposition. To test this hypothesis, we treated two isogenic pairs of iBBBs with CsA or FK506 for two weeks and subsequently added 20 nM of $A\beta_{1\text{-}40/42}$-FITC for 96 hours. In agreement with this hypothesis, both CsA and FK506 treatment led to significant reductions in amyloid accumulation in two-independent APOE4/4 iBBBs compared to their isogenic APOE3/3 controls (FIGS. 5*g* and *h*). We found the ability of CaN inhibition to reduce amyloid build-up also occurred to APOE3/4 heterozygous iBBBs (FIG. 5*i*).

Figure 5J:
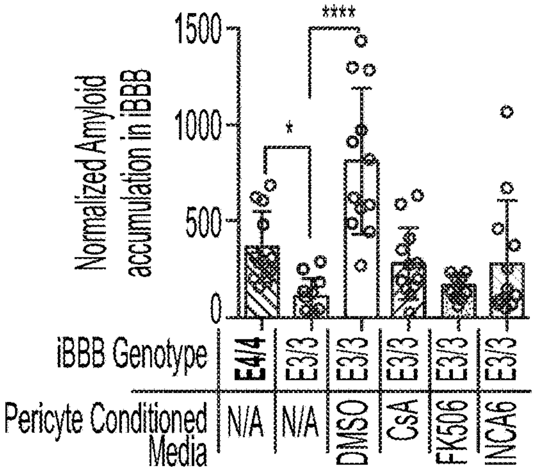
Figure 12F:
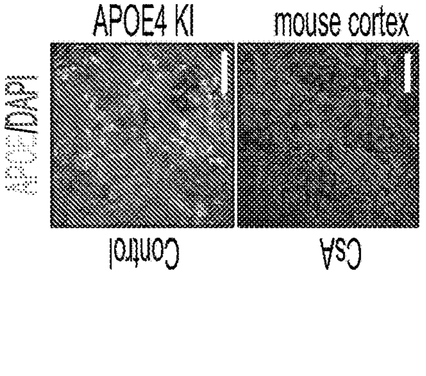
Figure 12G:
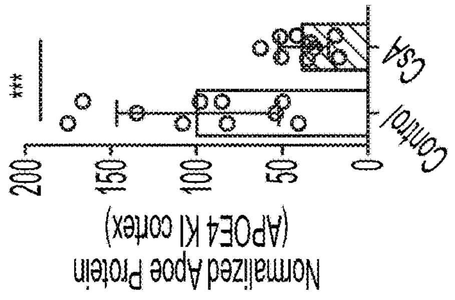
Figure 12H:
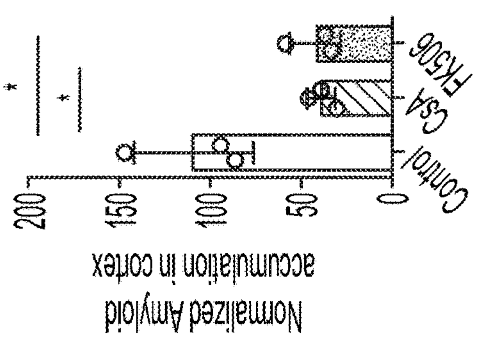

Previously, we observed that media conditioned by E4/4 pericytes was sufficient to increase amyloid accumulation of E3/3 iBBBs (FIG. 3*e*). The increased amyloid deposition due to E4/4 pericyte conditioned media is likely due to increased soluble APOE. Therefore, we hypothesized that treatment of E4/4 pericytes with CaN inhibitors would reduce soluble APOE and thereby lead to a reduction in iBBB amyloid accumulation. Indeed, we observed that whereas conditioned media from E4/4 pericytes treated with DMSO caused a significant increase in amyloid deposition in the E3/3 iBBB, media harvested from E4/4 pericytes treated with CsA, FK506, or INCA6 resulted in significantly reduced amyloid accumulation (FIG. 5*j*). To further extend this observation, we prepared cortical slice cultures from the ApoE4KI mice, and subsequently treated them with either DMSO, CsA or FK506 for 1 week. We then added 20 nM $A\beta_{1\text{-}40/42}$-FITC to the cultures for an additional 48 hours after which we quantified the accumulation of Aβ-FITC for each condition. We found that compared to the DMSO control both CsA and FK506 reduced APOE protein abundance and accumulation of Aβ FITC in APOE4KI cortical slice cultures (FIG. 12*f-h*).

Figure 13A:
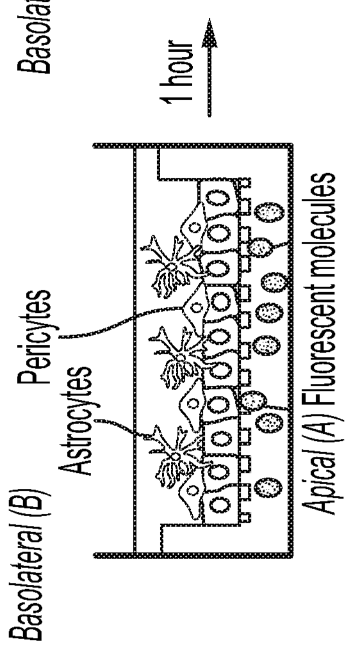
FIGS. 13A-13C show the genotype distinction between APOE4/4 cells (isogenic) and APOE3/3 (Parental) in permeability of a BBB membrane. 13A is a schematic showing the iBBB with fluorescent molecules positioned on the Apical surface. 13B is a schematic showing the iBBB with fluorescent molecules transitioning through the iBBB from the Apical surface to the Basolateral surface. 13C shows that the iBBB prepared with isogenic APOE4/4 cells allows greater permeability and accumulation of the fluorescent molecules than iBBB generated using parental APOE3/3 cells.
Figure 13B:
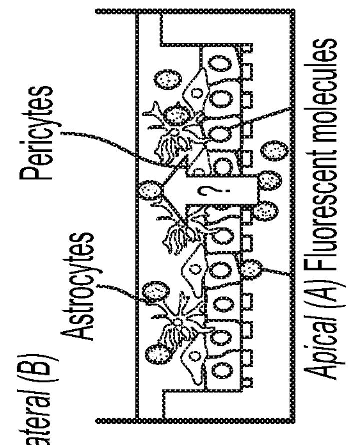
Figure 13C:
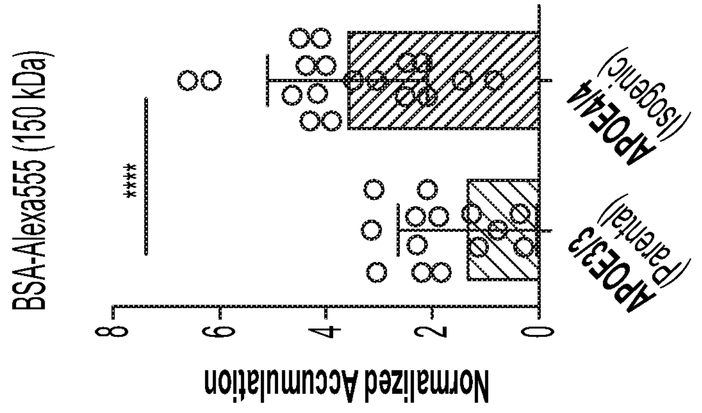

The genotype distinction between APOE4/4 cells (isogenic) and APOE3/3 (parental) was assessed in terms of permeability of an iBBB membrane. The results are shown in FIGS. 13-16. FIG. 13A presents a schematic showing the iBBB with fluorescent molecules positioned on the Apical surface, which are then allowed to transition through the iBBB from the Apical surface to the Basolateral surface (FIG. 13B). The results are shown in FIG. 13C, demonstrating that the iBBB prepared with isogenic APOE4/4 cells allows greater permeability and accumulation of the fluorescent molecules than iBBB generated using parental APOE3/3 cells.

Figure 14A:
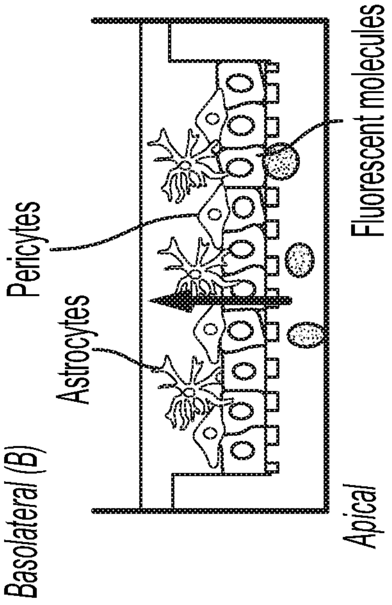
FIGS. 14A-14B show the genotype distinction between APOE4/4 cells (isogenic) and APOE3/3 (Parental) in permeability of a BBB membrane. 14A is a schematic showing the iBBB with fluorescent molecules positioned on the Apical surface. 14B is a graph showing that the iBBB prepared with isogenic APOE4/4 cells allows greater permeability and accumulation of multiple compounds than iBBB generated using parental APOE3/3 cells.
Figure 14B:
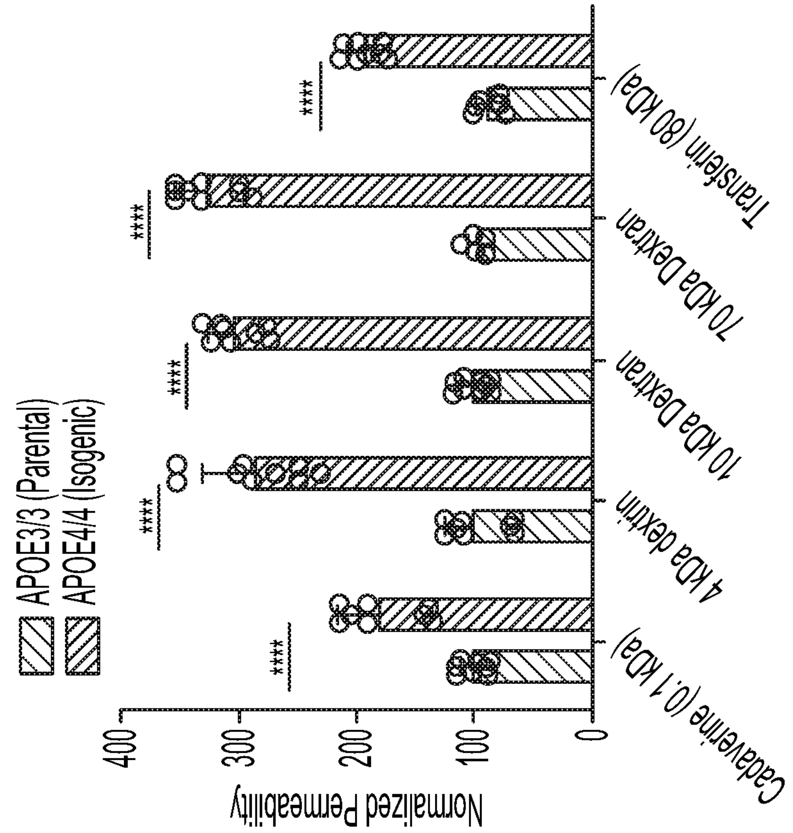
Figures 15A, 15B, 15C, 15D, 15E, 15F:
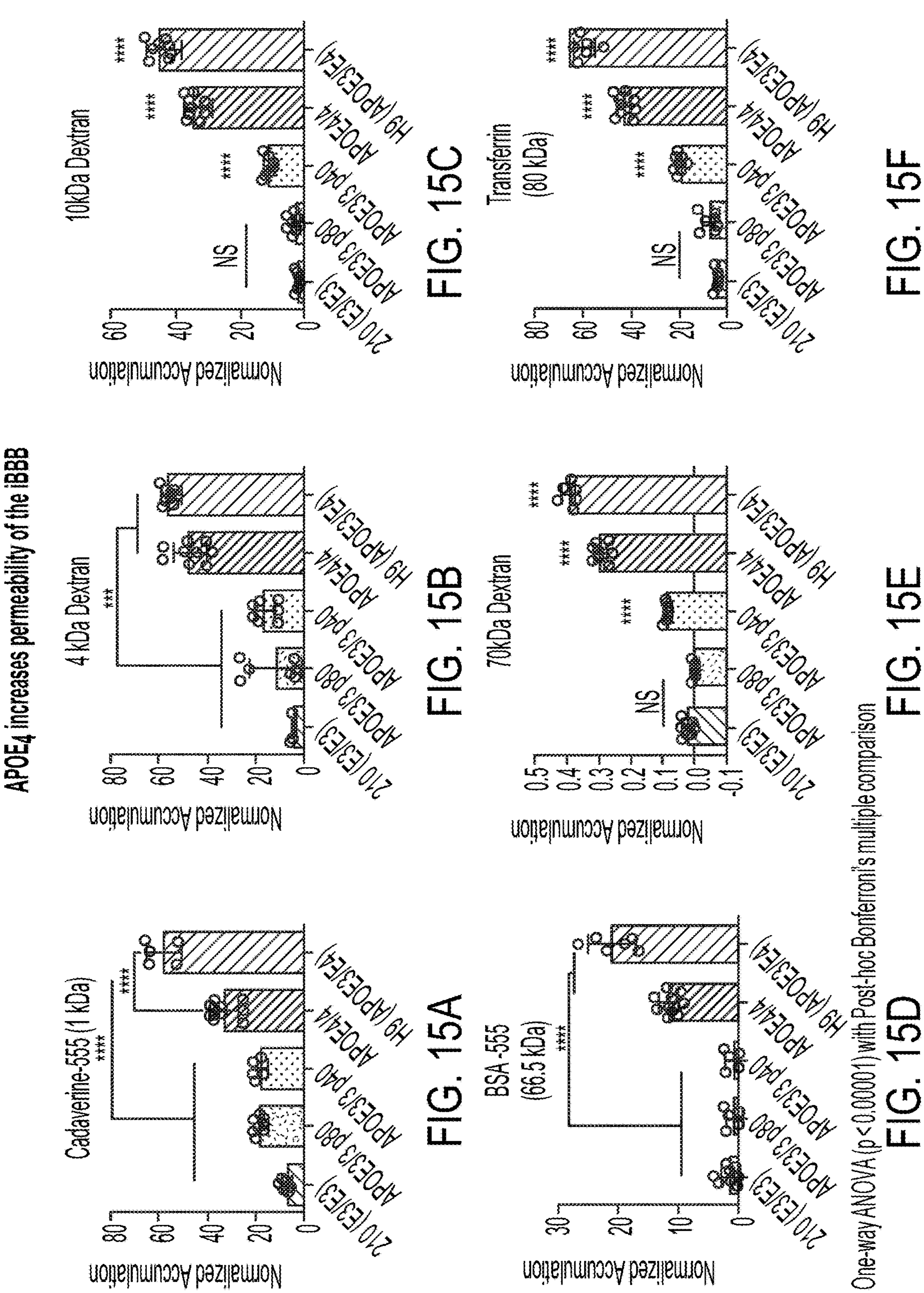
FIGS. 15A-15F shows that APOE4 increases the permability of iBBB membrane. 15A is a graph showing that the iBBB prepared with isogenic APOE4/4 cells allows greater permeability and accumulation of cadaverine molecules on the Basolateral surface of the iBBB than iBBB generated using parental APOE3/3 cells. 15B is a graph showing that the iBBB prepared with isogenic APOE4/4 cells allows greater permeability and accumulation of 4 kDa Dextran molecules on the Basolateral surface of the iBBB than iBBB generated using parental APOE3/3 cells. 15C is a graph showing that the iBBB prepared with isogenic APOE4/4 cells allows greater permeability and accumulation of 10 kDa Dextran molecules on the Basolateral surface of the iBBB than iBBB generated using parental APOE3/3 cells. 15D is a graph showing that the iBBB prepared with isogenic APOE4/4 cells allows greater permeability and accumulation of BSA molecules on the Basolateral surface of the iBBB than iBBB generated using parental APOE3/3 cells. 15E is a graph showing that the iBBB prepared with isogenic APOE4/4 cells allows greater permeability and accumulation of 70 kDa Dextran molecules on the Basolateral surface of the iBBB than iBBB generated using parental APOE3/3 cells. 15F is a graph showing that the iBBB prepared with isogenic APOE4/4 cells allows greater permeability and accumulation of transferrin molecules on the Basolateral surface of the iBBB than iBBB generated using parental APOE3/3 cells.
Figure 16:
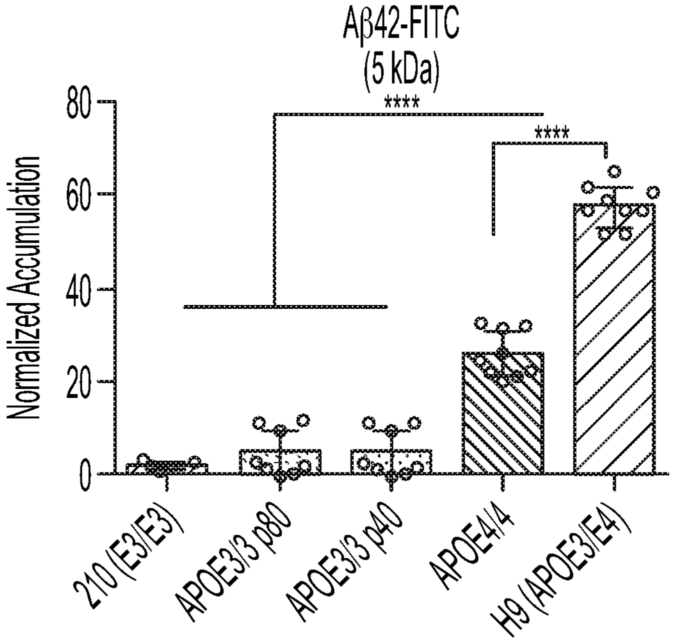
FIG. 16 is a graph showing that the iBBB prepared with isogenic APOE4/4 cells allows greater permeability and accumulation of A1342-FITC on the Basolateral surface of the iBBB than iBBB generated using parental APOE3/3 cells.

A study showing that the iBBB prepared with isogenic APOE4/4 cells allows greater permeability and accumulation of multiple compounds than iBBB generated using parental APOE3/3 cells (showed schematically as the iBBB with fluorescent molecules positioned on the Apical surface in FIG. 14A) was also performed. The data is shown in FIG. 14B in summary form. FIGS. 15A-15F are a series of graphs showing the full data set for each tested compound (cadaverine (15A), 4 kDa Dextran (15B), 10 kDa Dextran (15C), BSA (15D), 70 kDa Dextran (15E), and transferrin (15E). FIG. 16 is a graph showing that the iBBB prepared with isogenic APOE4/4 cells allows greater permeability and accumulation of Aβ42-FITC on the Basolateral surface of the iBBB than iBBB generated using parental APOE3/3 cells.

Figure 12I:
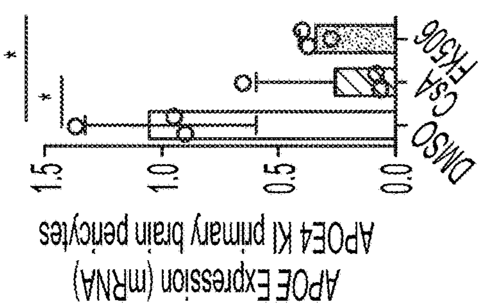

Taken together, our results demonstrate that dysregulation of CaN/NFAT signaling in APOE4 pericytes leads to increased amyloid accumulation through up-regulation of APOE expression in human pericytes, and that this phenotype is ameliorated through pharmacological inhibition of CaN signaling. To further examine this finding we first isolated brain microvasculature from APOE4KI mice and subsequently selected for pericytes by culturing in pericyte selection media for 3 weeks resulting in nearly homogenous pericyte cultures. We then treated these APOE4KI primary brain pericyte cultures for two weeks with DMSO, CsA or FK506. Similar to iPSC-derived human pericytes, primary mouse brain pericytes isolated from APOE4KI mice down-regulated APOE mRNA expression in response to CsA and FK506 (FIG. 12*i*).

Figure 5K:
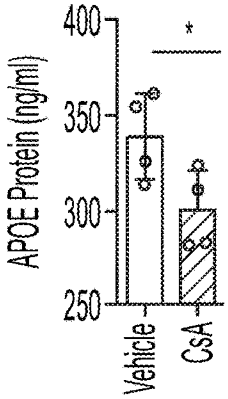
Figure 5L:
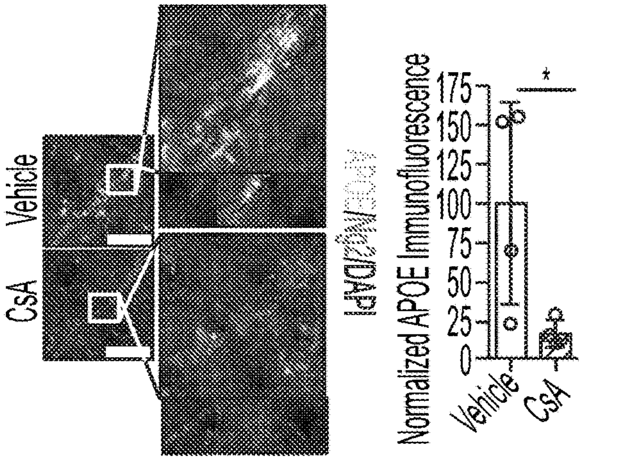
Figure 5M:
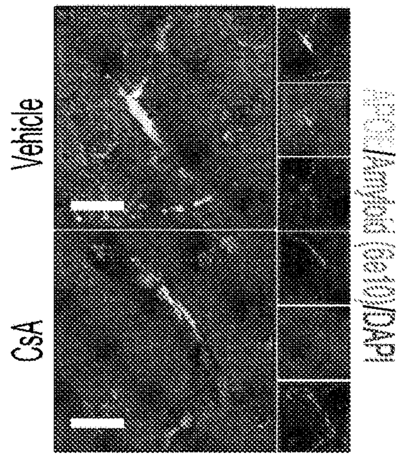
Figure 5N:
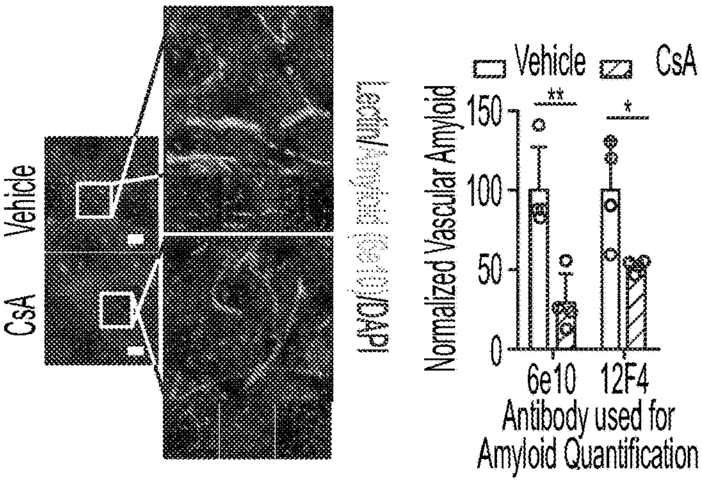
Figure 12J:
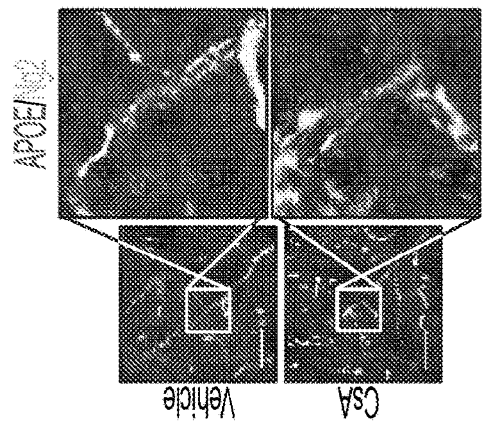
Figure 12K:
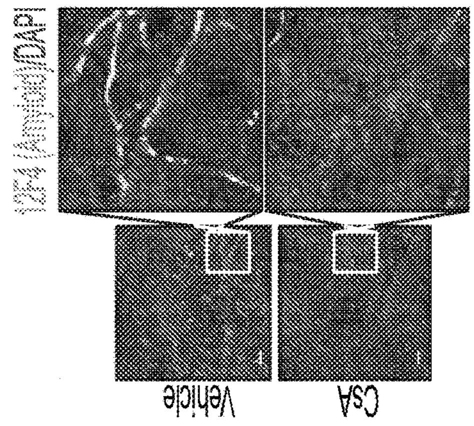

Next, to examine whether this biological insight can be applied in vivo to reduce disease pathology we employed 6-month-old APOE4 KI mice crossed to the 5XFAD AD mouse model (APO4KI×5XFAD) and treated them with CsA (10 mg/kg) for three weeks via intraperitoneal injection. CsA treatment led to a significant reduction of APOE concentration in the hippocampus measured by ELISA (FIG. 5*k*). Immunohistochemistry revealed that APOE protein expression was also reduced in and around cortical and hippocampal pericytes of APOE4KI×5XFAD mice treated with CsA compared to control mice (FIG. 5*l*; FIG. 12*j*). Co-staining for 6e10 and APOE showed that reduced APOE occurred simultaneously with lower levels of 6e10-positive vascular amyloid (FIG. 5*m*). Therefore, we quantified vascular amyloid with two separate antibodies (6e10 and 12F4) that recognize distinct peptide sequences of Aβ oligomers. We found that CsA treated mice had significantly reduced vascular amyloid by 70.6%+/−18.4 (6e10) and 47.8%+/−4.1 (12F4) in the hippocampus compared to vehicle treated mice (FIG. 5*n* and FIG. 12*k*). These results demonstrate that CaN/NFAT inhibition can reduce pericyte APOE levels and vascular amyloid in vivo.

Figure 17A:
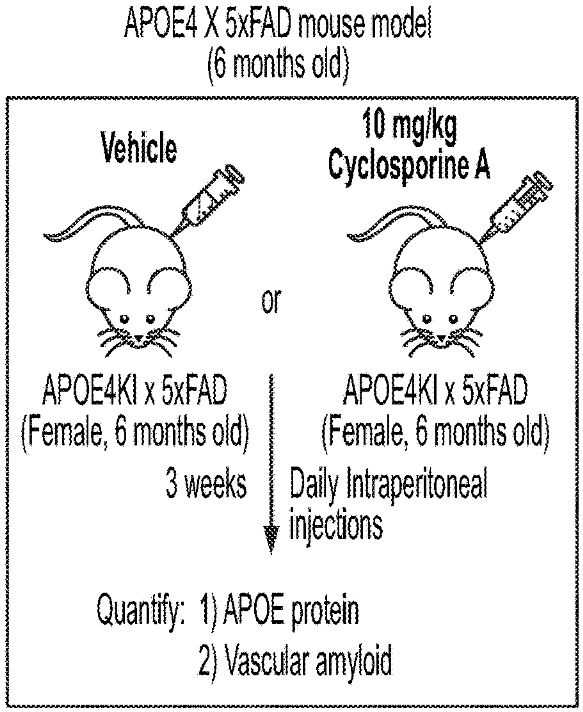
FIGS. 17A-17C show in vivo cyclosporine A reduces APOE in and around cortical pericytes. 17A is a schematic showing the experimental steps wherein APOE4K1×5XFAD mice are injected with vehicle control or 10 mg/kg cyclosporin A intraperitoneal, daily for 3 weeks. APOE protein and vascular amyloid are quantified. 17B is a graph showing the results generated by ELISA assay and demonstrating that cyclosporin A resulted in less production of APOE protein relative to vehicle. 17C is images and a graph showing the results of immunohistochemistry of the hippocampus and demonstrating that cyclosporin A resulted in less accumulation of APOE protein relative to vehicle.
Figure 17B:
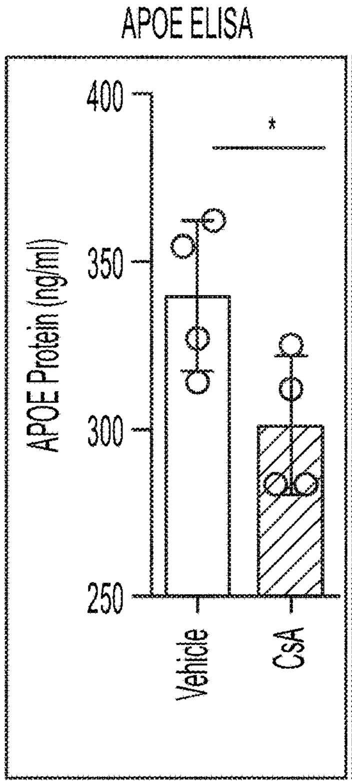
Figure 17C:
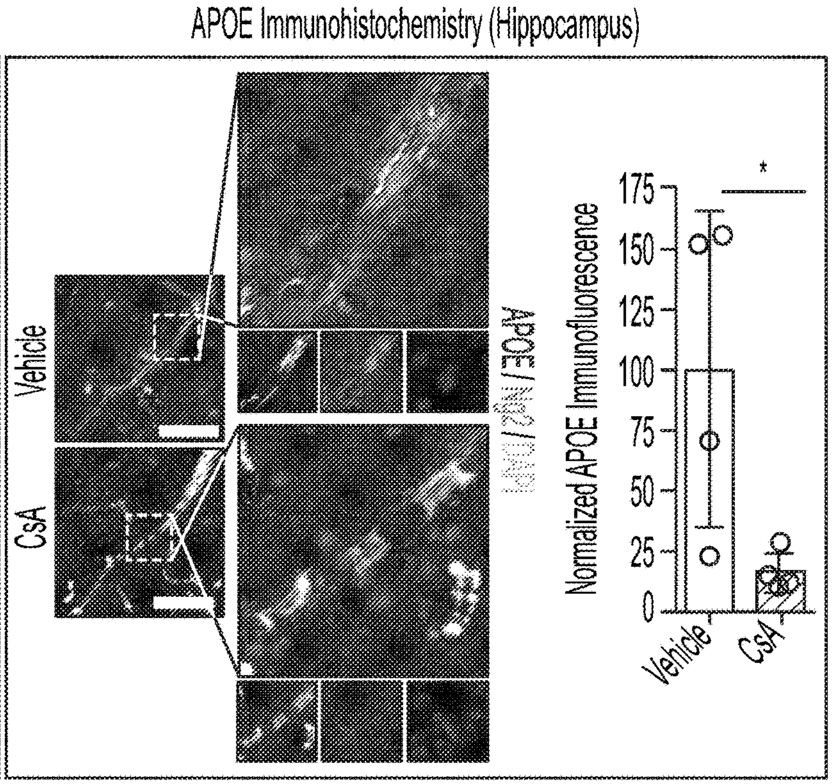

Cyclosporine A was demonstrated to reduce APOE and amyloid protein production/accumulation in vivo (FIGS. 17A-C, FIGS. 18A-B and FIGS. 19A-19C). APOE4K1×5×FAD mice were injected with vehicle control or 10 mg/kg cyclosporin A intraperitoneal, daily for 3 weeks and APOE protein and vascular amyloid were quantified (schematically presented in FIG. 17A). The data is shown in FIGS. 17B-C. A graph showing the results generated by ELISA assay and demonstrating that cyclosporin A resulted in less production of APOE protein relative to vehicle is shown in FIG. 17B. FIG. 17C is images and a graph showing the results of immunohistochemistry of the hippocampus and demonstrating that cyclosporin A resulted in less accumulation of APOE protein relative to vehicle in and around cortical pericytes.

Figure 18A:
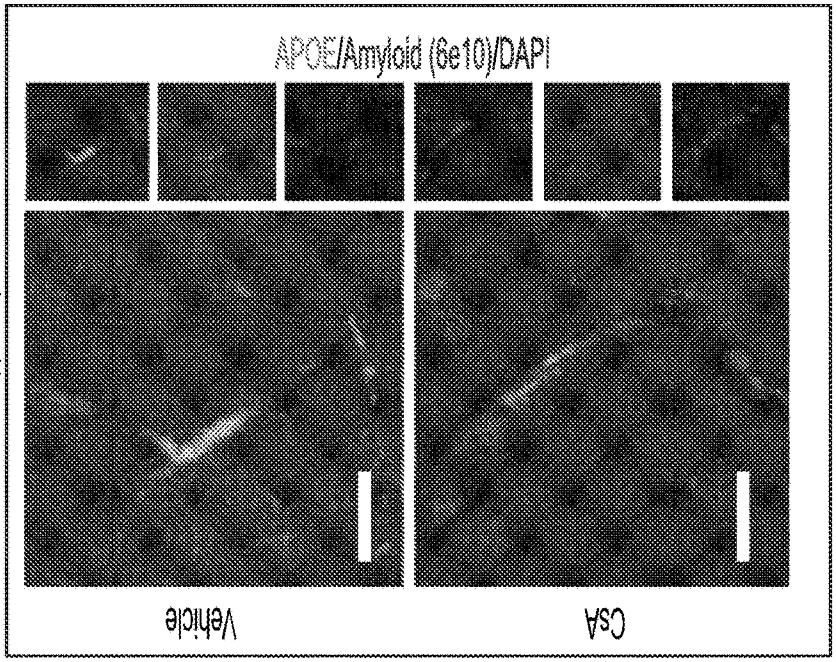
FIGS. 18A-18B show in vivo cyclosporine A reduces APOE and vascular amyloid in and around hippocampus vasculature. 18A is an image showing the results generated by immunohistochemistry of the hippocampus and demonstrating that cyclosporin A resulted in less production of APOE/amyloid protein relative to vehicle. 18B is images and a graph showing the results of immunohistochemistry of the hippocampus and demonstrating that cyclosporin A resulted in less accumulation of vascular amyloid protein relative to vehicle.
Figure 18B:
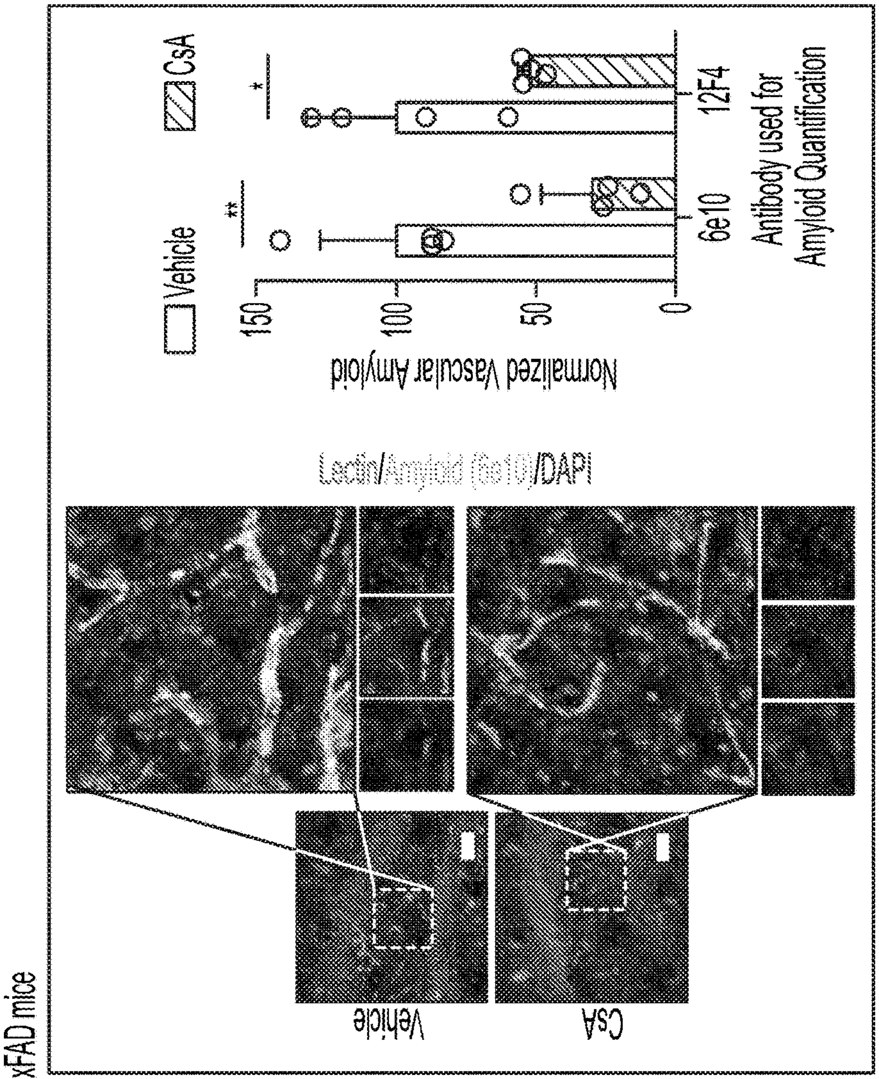
Figure 19A:
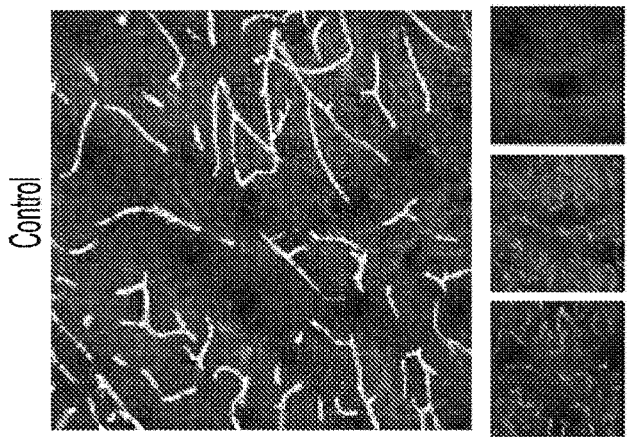
FIGS. 19A-19D show in vivo cyclosporine A and FK506 reduce APOE and vascular amyloid in and around hippocampus vasculature in vivo. 19A is an image showing the results generated by immunohistochemistry of the hippocampus and demonstrating control levels of vascular amyloid protein. 19B is an image showing the results generated by immunohistochemistry of the hippocampus and demonstrating that cyclosporin A (10 mg/ml) resulted in less production of amyloid protein relative to vehicle control. 19C is an image showing the results generated by immunohistochemistry of the hippocampus and demonstrating that FK506 (10 mg/ml) resulted in less production of amyloid protein relative to vehicle control. 19D is a graph depicting the results of the data generated in 19A-19C.
Figure 19B:
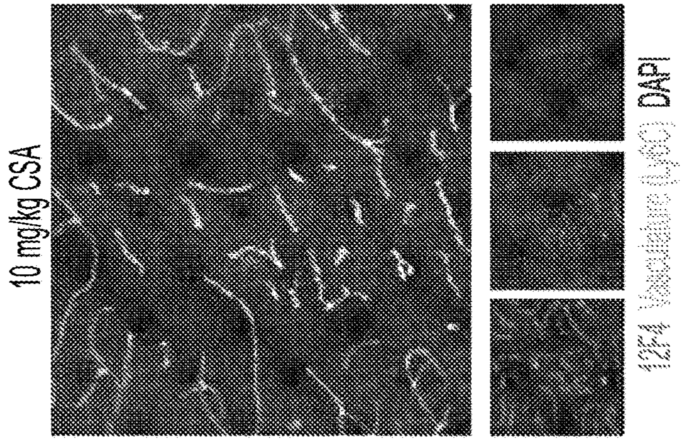
Figure 19C:
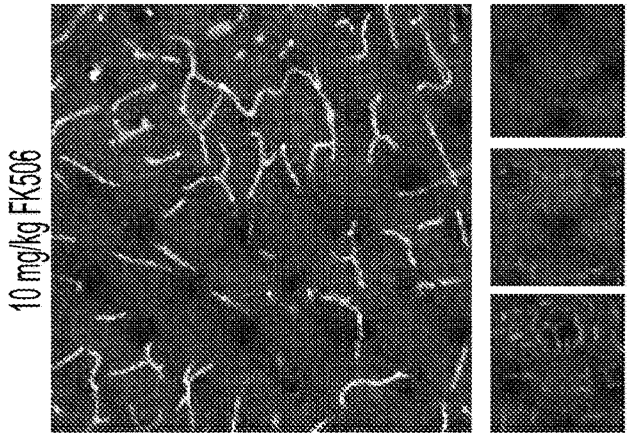
Figure 19D:
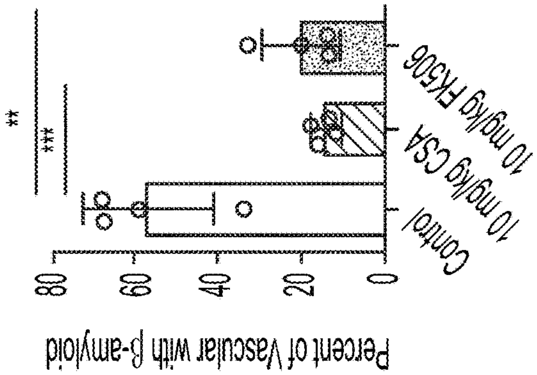

In vivo cyclosporine A reduces APOE and vascular amyloid in and around hippocampus vasculature. FIG. 18A is an image showing the results generated by immunohistochemistry of the hippocampus and demonstrating that cyclosporin A resulted in less production of APOE/amyloid protein relative to vehicle. FIG. 18B is images and a graph showing the results of immunohistochemistry of the hippocampus and demonstrating that cyclosporin A resulted in less accumulation of vascular amyloid protein relative to vehicle. In FIGS. 19A-19D it is shown that in vivo cyclosporine A and FK506 reduce APOE and vascular amyloid in and around hippocampus vasculature in vivo. In FIG. 19C an image showing the results generated by immunohistochemistry of the hippocampus and demonstrating that FK506 (10 mg/ml) resulted in less production of amyloid protein relative to vehicle control.

TABLE 1

Antibodies used in this study.

| Antibody | Host species | Vendor | Catalogue No. | Dilution |
|---|---|---|---|---|
| S-100B | Mouse | Sigma-Aldrich | S2532 | 1:500 |
| ZO-1 | Mouse | Thermo Fisher | MA3-39100 | 1:500 |
| VE-Cadherin/CD144 | Goat | R&D Systems | AF938 | 1:500 |
| SM22 | Rabbit | abcam | ab14106 | 1:500 |
| Aquaporin 4 | Rabbit | Thermo Fisher | PA5-53234 | 1:500 |
| 6E10 | Mouse | BioLegend | SIG-39320 | 1:500 |
| CD31/PECAM-1 | Sheep | R&D Systems | AF806 | 1:500 |
| GAPDH | Mouse | Santa Cruz | Sc-32233 | 1:500 |
| APOE | Rabbit | abcam | EP1374Y | 1:500 |
| SMA | Mouse | R&D Systems | MAB1420 | 1:500 |
| GLUT-1 | Rabbit | abcam | ab15309 | 1:500 |
| CLDN5 | Mouse | Thermo Fisher | 352588 | 1:500 |
| GFAP | Rabbit | Millipore Sigma | AB5804 | 1:500 |
| NFATc1 | Mouse | Thermo Fisher | MA3024 | 1:50 |
| Hoechst 33342 | | Thermo Fisher | H3570 | 1:2000 |
| NG2 | Mouse | BD Bioscience | 554275 | 1:100 |
| D54D2 | Rabbit | Cell Signaling | 8243S | 1:500 |
| 12F4 | Mouse | BioLegend | 805501 | 1:500 |
| Thioflavin T | | Sigma-Aldrich | T3516 | 10 μM |
| CD13 | Rabbit | Abcam | EPR4058 | 1:100 |
| Secondary Antibody | | | | |
| Donkey anti-mouse Alexa 488 | | Thermo Fisher | A-21202 | 1:1000 |
| Donkey anti-mouse Alexa 555 | | Thermo Fisher | A-31570 | 1:1000 |
| Donkey anti-goat Alexa Alexa 555 | | Thermo Fisher | A-21432 | 1:1000 |
| Donkey anti-Rabbit Alexa 488 | | Thermo Fisher | A-21206 | 1:1000 |

TABLE 2

Pluripotent cell lines used in study.

| | Line | | APOE genotype | Sex | Age at biopsy |
|---|---|---|---|---|---|
| 1 | 210 | N/A | APOE3/3 | F | 33 |
| 2 | sAD231 | N/A | APOE3/4 | M | 65 |
| 3 | sAD330 | N/A | APOE3/3 | M | 56 |
| 4 | sAD332 | N/A | APOE3/4 | F | 82 |
| 5 | sAD369 | N/A | APOE3/3 | M | 76 |
| 6 | sAD402 | N/A | APOE3/4 | F | 70 |
| 7 | H9 | N/A | APOE3/4 | F | N/A |
| 8 | AGO9173 (E3/E3) | Parental | APOE3/3 | F | 75 |
| 9 | E3/E3 clone 2 | Isogenic | APOE3/3 | F | 75 |
| 10 | E4/E4 | Isegenic | APOE4/4 | F | 75 |
| 11 | E4/E4 clone 2 | Isogenic | APOE4/4 | F | 75 |

TABLE 2-continued

| Pluripotent cell lines used in study. | | | | | |
|---|---|---|---|---|---|
| | Line | | APOE genotype | Sex | Age at biopsy |
| 12 | KO | Isogenic | KO | F | 75 |
| 13 | AG10788 (sADE3/3) | Isogenic | APOE3/3 | F | 70 |
| 14 | sADE4/4 | Parental | APOE4/4 | F | 70 |
| 15 | APP1.1 | N/A | | M | 46 |

OTHER EMBODIMENTS

The invention is further captured in one or more of the following paragraph embodiments.

Paragraph 1. An in vitro blood brain barrier (iBBB) comprising a 3 dimensional (3D) matrix comprising

- a human brain endothelial cell (BEC) vessel comprised of a large interconnected network of human pluripotent-derived positive endothelial cells encapsulated in a 3D matrix,
- human pluripotent-derived pericytes proximal to the BEC vessel on an apical surface, and
- human pluripotent-derived astrocytes dispersed throughout the 3D matrix, wherein a plurality of the astrocytes are proximal to the BEC vessel and have GFAP-positive projections into the perivascular space.

Paragraph 2. An in vitro blood brain barrier (iBBB) comprising a 3 dimensional (3D) matrix comprising

- a human brain endothelial cell (BEC) vessel comprised of a large interconnected network of endothelial cells encapsulated in a 3D matrix,
- pericytes proximal to the BEC vessel on an apical surface, wherein the pericytes have an E4/E4 genotype, and
- astrocytes proximal to the BEC vessel, wherein a plurality of the astrocytes have positive projections into the perivascular space.

Paragraph 3. The iBBB of any of the above Paragraphs, wherein the astrocytes express AQP4.

Paragraph 4. The iBBB of any of the above Paragraphs, wherein the 3D matrix comprises LAMA4.

Paragraph 5. The iBBB of any of the above Paragraphs, wherein the BEC express at least any one of JAMA, PgP, LRP1, and RAGE.

Paragraph 6. The iBBB of any of the above Paragraphs, wherein PgP and ABCG2 are expressed on the apical surface.

Paragraph 7. The iBBB of any of the above Paragraphs, wherein levels of PgP and ABCG2 expressed on the apical surface are 2-3 times greater than levels of PgP and ABCG2 expressed on BEC cultured alone or co-cultured with astrocytes.

Paragraph 8. The iBBB of any of the above Paragraphs, wherein the iBBB has a TEER that exceeds 5,500 Ohm× cm2, exhibits reduced molecular permeability and polarization of efflux pumps relative to BEC cultured alone or co-cultured with astrocytes.

Paragraph 9. The iBBB of any of the above Paragraphs, wherein the iBBB is not cultured with retinoic acid.

Paragraph 10. The iBBB of any of the above Paragraphs, wherein the human pluripotent are iPSC-derived CD144 cells.

Paragraph 11. The iBBB of any of the above Paragraphs, wherein the iBBB is generated using 5 parts endothelial cells to 1 part astrocytes to 1 part pericytes.

Paragraph 12. The iBBB of any of the above Paragraphs, wherein the iBBB is generated using about 1 million endothelial cells per ml, about 200,000 astrocytes per ml and about 200,000 pericytes per ml.

Paragraph 13. The iBBB of any of the above Paragraphs, wherein the iBBB is 5 to 50 microns in length.

Paragraph 14. The iBBB of any of the above Paragraphs, wherein the iBBB is 5 to 30 microns in length.

Paragraph 15. The iBBB of any of the above Paragraphs, wherein the iBBB is 10 to 20 microns in length.

Paragraph 16. The iBBB of any of the above Paragraphs, wherein the BEC vessel is a capillary size.

Paragraph 17. A method for identifying an effect of a compound on a blood brain barrier, comprising:

providing an iBBB of any of the above Paragraphs, contacting the BEC vessel of the iBBB with a compound, and detecting the effect of the compound on the iBBB relative to an iBBB which has not been contacted with the compound.

Paragraph 18. The method of any of the above Paragraphs, wherein the effect of the compound on the iBBB is measured as a change in expression of an extracellular matrix factor.

Paragraph 19. The method of any of the above Paragraphs, wherein the effect of the compound on the iBBB is measured as a change in expression of gene.

Paragraph 20. The method of any of the above Paragraphs, wherein the effect of the compound on the iBBB is measured as a change in expression of a soluble factor.

Paragraph 21. The method of any of the above Paragraphs, wherein the compound alters one or more functional properties of the iBBB.

Paragraph 22. The method of any of the above Paragraphs, wherein the functional properties of the iBBB are cell migration, molecular permeability or polarization of efflux pumps.

Paragraph 23. The method of any of the above Paragraphs, wherein the effect of the compound on the iBBB is measured as a change in amyloid deposits.

Paragraph 24. A method for identifying an inhibitor of amyloid-β peptide (Aβ) production and/or accumulation, comprising:

- contacting an Aβ producing cell with an APOE4 positive pericyte factor and at least one candidate inhibitor and detecting an amount of Aβ in the presence and absence of the candidate inhibitor, wherein a reduced quantity of Aβ associated with the cell in the presence of the candidate inhibitor relative an amount of Aβ associated with the cell in the absence of the candidate inhibitor indicates that the candidate inhibitor is an inhibitor of Aβ.

Paragraph 25. The method of any of the above Paragraphs, wherein the APOE4 positive pericyte factor is a soluble factor in APOE4 pericyte conditioned media.

Paragraph 26. The method of c any of the above Paragraphs, wherein the soluble factor is APOE protein.

Paragraph 27. The method of any of the above Paragraphs, wherein the APOE4 positive pericyte factor is APOE protein produced by pericytes.

Paragraph 28. The method of any of the above Paragraphs, wherein the Aβ producing cell expressed APOE3.

Paragraph 29. The method of any of the above Paragraphs, wherein the Aβ producing cell has an APOE3/3 genotype or an APOE3/4 genotype.

Paragraph 30. The method of any of the above Paragraphs, wherein the Aβ producing cell is an APOE4 positive pericyte.

Paragraph 31. The method of any of the above Paragraphs, wherein the pericyte has an APOE4/4 genotype.

Paragraph 32. The method of any of the above Paragraphs, wherein the pericyte has an APOE3/4 genotype.

Paragraph 33. The method of any of the above Paragraphs, wherein the APOE4 positive pericyte factor is a soluble factor produced by an APOE4 pericyte co-incubated with the Aβ producing cell.

Paragraph 34. The method of any of the above Paragraphs, wherein the Aβ producing cell is an astrocyte or a endothelial cell.

Paragraph 35. The method of any one of any of the above Paragraphs, further comprising providing an iBBB of any one of any of the above Paragraphs, contacting the BEC vessel of the iBBB with the inhibitor of Aβ, and detecting the effect of the inhibitor of Aβ on the production of Aβ by the iBBB relative to an iBBB which has not been contacted with the inhibitor of Aβ.

Paragraph 36. A method for inhibiting amyloid synthesis in a subject, comprising determining whether a subject has or is at risk of developing amyloid accumulation by identifying the subject as APOE4 positive, if the subject is APOE4 positive, administering to the subject an inhibitor of calcineurin/NFAT pathway in an effective amount to inhibit amyloid synthesis in the subject, wherein the inhibitor of calcineurin/NFAT pathway is not cyclosporin.

Paragraph 37. A method for inhibiting amyloid synthesis in a subject, comprising administering to the subject having or at risk of having CAA an inhibitor of calcineurin/NFAT pathway in an effective amount to inhibit amyloid synthesis in the subject, wherein the inhibitor of calcineurin/NFAT pathway is not cyclosporin.

Paragraph 38. A method for inhibiting amyloid synthesis in a subject, comprising administering to the subject an inhibitor of C/EBP pathway in an effective amount to inhibit amyloid synthesis in the subject.

Paragraph 39. The method of any of the above Paragraphs, wherein the subject has Alzheimer's disease.

Paragraph 40. The method of any of the above Paragraphs, wherein the subject has CAA.

Paragraph 41. The method of any of the above Paragraphs, wherein the subject has not been diagnosed with Alzheimer's disease.

Paragraph 42. The method of any of the above Paragraphs, wherein the subject does not have Alzheimer's disease.

Paragraph 43. The method of any of the above Paragraphs, wherein the inhibitor of calcineurin/NFAT pathway is a small molecule inhibitor.

Paragraph 44. The method of any of the above Paragraphs, wherein the inhibitor of calcineurin/NFAT pathway is FK506.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. An in vitro blood brain barrier (iBBB) comprising a 3-dimensional (3D) matrix comprising a human brain endothelial cell (BEC) vessel of about 5 to 10 microns in diameter and 5 to 50 microns in length comprised of a large interconnected network of human induced pluripotent-derived stem cell (iPSC) endothelial cells (iPSC-ECs) encapsulated in a 3D matrix, human induced pluripotent-derived stem cell (iPSC) pericytes (iPSC-PCs) proximal to the BEC vessel on an apical surface, and human induced pluripotent-derived stem cell (iPSC) astrocytes (iPSC-astrocytes) dispersed throughout the 3D matrix, wherein a plurality of the iPSC-astrocytes are proximal to the BEC vessel and have glial fibrillary acidic protein (GFAP)-positive projections into the perivascular space.

2. The iBBB of claim 1, wherein the iPSC-astrocytes express Aquaporin 4 (AQP4).

3. The iBBB of claim 1, wherein the 3D matrix comprises laminin α4 (LAMA4).

4. The iBBB of claim 1, wherein the BEC express at least any one of P-glycoprotein (PgP), Low-density lipoprotein receptor-related protein 1 (LRP1), and receptor for advanced glycation end products (RAGE).

5. The iBBB of claim 1, wherein PgP and ATP binding cassette subfamily G member 2 (ABCG2) are expressed on the apical surface of the BEC vessel.

6. The iBBB of claim 5, wherein levels of PgP and ABCG2 expressed on the apical surface of the BEC vessel are 2-3 times greater than levels of PgP and ABCG2 expressed on BEC cells cultured alone or co-cultured with astrocytes.

7. The iBBB of claim 1, wherein the iBBB has a TEER that exceeds 5,500 Ohm×cm2, exhibits reduced molecular permeability and polarization of efflux pumps relative to BEC cultured alone or co-cultured with astrocytes.

8. The iBBB of claim 1, wherein the iPSC-ECs are iPSC-derived CD144 cells.

9. The iBBB of claim 1, wherein the iBBB is generated using 5 parts iPSC-ECs to 1 part iPSC-astrocytes to 1 part iPSC-PCs.

10. The iBBB of claim 1, wherein the iBBB is generated using about 1 million iPSC-ECs per ml, about 200,000 iPSC-astrocytes per ml and about 200,000 iPSC-PCs per ml.

11. The iBBB of claim 1, wherein the iBBB is 5 to 30 microns in length.

12. The iBBB of claim 1, wherein the iBBB is 10 to 20 microns in length.

13. The iBBB of claim 1, wherein the BEC vessel is a capillary size.

14. The iBBB of claim 1, wherein the 3D matrix is contained in a glass bottom culture dish.

15. The iBBB of claim 1, wherein the 3D matrix is one or more of a Matrigel hydrogel, Myogel and Cartigel, or a combination of Matrigel, Myogel and Cartigel and one or more of a naturally derived biomaterial or biomaterials or hydrophilic polymers that are linear or branched wherein the polymers are synthetic.

* * * * *